(12) United States Patent
LaRosa et al.

(10) Patent No.: US 6,727,349 B1
(45) Date of Patent: Apr. 27, 2004

(54) RECOMBINANT ANTI-CCR2 ANTIBODIES AND METHODS OF USE THEREFOR

(75) Inventors: Gregory J. LaRosa, Newton, MA (US); Christopher Horvath, Taunton, MA (US); Walter Newman, Boston, MA (US); S. Tarran Jones, Radlett (GB); Siobhan H. O'Brien, Finchley (GB); Theresa O'Keefe, Waltham, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/497,625

(22) Filed: Feb. 3, 2000

Related U.S. Application Data

(63) Continuation-in-part of application No. 09/359,193, filed on Jul. 22, 1999, now Pat. No. 6,352,832, which is a continuation-in-part of application No. 09/121,781, filed on Jul. 23, 1998, now Pat. No. 6,312,689.

(51) Int. Cl.$^7$ ................................................ C07K 16/00
(52) U.S. Cl. ................................ 530/387.3; 424/130.1; 424/156.1; 530/387.1; 530/388.23
(58) Field of Search ......................... 530/387.1, 387.3, 530/388.1, 388.23, 300, 350; 424/130.1, 133.1, 135.1, 156.1

(56) References Cited

U.S. PATENT DOCUMENTS

| | | | | |
|---|---|---|---|---|
| 4,816,397 A | * | 3/1989 | Boss et al. | |
| 4,816,567 A | * | 3/1989 | Cabilly et al. | |
| 5,225,539 A | * | 7/1993 | Winter et al. | |
| 5,440,021 A | * | 8/1995 | Chuntharapai et al. | |
| 5,543,503 A | * | 8/1996 | Chuntharapai et al. | |
| 5,571,713 A | | 11/1996 | Lyle et al. | |
| 5,585,089 A | * | 12/1996 | Queen et al. | |
| 5,693,761 A | * | 12/1997 | Queen et al. | |
| 5,693,762 A | * | 12/1997 | Queen et al. | |
| 5,707,815 A | * | 1/1998 | Charo et al. | |
| 5,859,205 A | * | 1/1999 | Adair et al. | |
| 6,084,075 A | * | 7/2000 | Lind et al. | |

FOREIGN PATENT DOCUMENTS

| | | | |
|---|---|---|---|
| WO | WO 91/09967 | | 7/1991 |
| WO | WO 94/09128 | | 4/1994 |
| WO | WO 95/08576 | * | 3/1995 |
| WO | WO 95/19436 | | 7/1995 |
| WO | WO 97/31949 | | 9/1997 |
| WO | WO 98/44953 | | 10/1998 |
| WO | WO 99/15666 | * | 4/1999 |
| WO | WO 00/05265 | | 2/2000 |

OTHER PUBLICATIONS

Monteclaro, F.S.and Charo, I.F., "The Amino–terminal Domain of CCR2 Is Both Necessary and Sufficient for High Affinity Binding of Monocyte Chemoattractant Protein 1", *The Journal of Biological Chemistry* 272(37):23186–23190 (1997).

Qin, S., et al., "Expression of monocyte chemoattractant protein–1 and interleukin–8 receptors on subsets of T cells: correlation with transendothelial chemotactic potential," *Eur. J. Immunol.*, 26:640–647 (1996).

Yamagami, S., et al., "cDNA Cloning and Functional Expression of a Human Monocyte Chemoattractant Protein 1 Receptor," *Biochemical and Biophysical Research Communications*, 202(2):1156–1162 (1994).

Charo, I.F., et al., "Molecular cloning and functional expression of two monocyte chemoattractant protein 1 receptors reveals alternative splicing of the carboxyl–terminal tails," *Proc. Natl. Acad. Sci., USA.*, 91:2752–2756 (1994).

Aragay, A.M., et al., "Monocyte chemoattractant protein–1–induced CCR2B receptor desensitization mediated by the G protein–coupled receptor kinase 2," *Proc. Natl. Acad. Sci., USA*, 95:2985–2990 (1998).

Frade, J.M.R., et al., "Characterization of the CCR2 Chemokine Receptor: Functional CCR2 Receptor Expression in B Cells," *J. Immunol.*, 159(11):5576–5584 (1997).

Frade, J.M.R., et al., "The Amino–Terminal Domain of the CCR2 Chemokine Receptor Acts as Coreceptor for HIV–1 Infection," *J. CLin. Invest.*, 100(3):497–502 (1997).

Wong, L.–M., et al., "Organization and Differential Expression of the Human Monocyte Chemoattractant Protein 1 Receptor Gene," *The Journal Biological Chemistry*, 272(2):1038–1045 (1997).

Kurihara, T. and Bravo, R., "Cloning and Functional Expression of mCCR2, a Murine Receptor for the C–C Chemokines JE and FIC," *The Journal of Biological Chemistry*, 271(20):11603–11606 (1996).

Grimm, M.C., et al., "Enhanced expression and production of monocyte chemoattractant protein–1 in inflammatory bowel disease mucosa," *Journal of Leukocyte Biology* 59:804–812 (1996).

Izikson, L., et al., "Resistance to Experimental Autoimmune Encephalomyelitis in Mice Lacking the CC Chemokine Receptor (CCR)2," *J. Exp. Med.*, 192(7):1075–1080 (2000).

Fife, B.T., et al., "CC Chemokine Receptor 2 Is Critical for Induction of Experimental Autoimmune Encephalomyelitis," *J. Exp. Med.*, 192(6):899–905 (2000).

Sanz, I., et al., "Evidence That Autoantibodies Can Be Unmutated Copies of Germline Genes," *The Journal of Immunology* 142(3):883–887 (1989).

(List continued on next page.)

Primary Examiner—Larry R. Helms
(74) *Attorney, Agent, or Firm*—Hamilton, Brook, Smith & Reynolds, P.C.

(57) ABSTRACT

The present invention relates to a humanized antibody or functional fragment thereof which binds to a mammalian (e.g., human) CC-chemokine receptor 2 (CCR2) or a portion of the receptor and blocks binding of a ligand to the receptor. The invention further relates to a method of inhibiting the interaction of a cell bearing mammalian CCR2 with a ligand thereof, and to use of the antibodies and fragments in therapeutic, prophylactic and diagnostic methods.

62 Claims, 39 Drawing Sheets

OTHER PUBLICATIONS

Chastangner, P., et al., "Cloning of a gene encoding a lupus–associated human autoantibody $V_k$ region using the polymerase chain reaction an degenerate primers," *Gene* 101:305–306 (1991).

Chothia, C., et al., "Conformations of immunoglobulin hypervariable regions," *Nature* 342:877–883 (1989).

Huston, James S., et al., "Engineered antibodies take center stage", *Human Antibodies*, 10:127–142 (2001).

Reichert, Janice M., "Monoclonal antibodies in the clinic", *Nature Biotechnology*, 19: 819–822 (2001).

Welt, et al., "Targeting CCR–2 or CD18 Inhibits Experimental in–Stent Restenosis in Primates. Inhibitory Potential Depends on Type of Injury and Leukocytes Targeted", *Circulation–Journal of the American Heart Association* (Abstracts from Scientific Sessions 2000), 102(18): II–247, Abstract 1206 (2000).

Paul, Fundamental Immunology, Raven Press NY, Chapter 8, p. 242, 1993.

Rudikoff et al., Proc. Natl. Acad. Sci. USA 79:1979, 1982.

Förster, R., et al., "A general method for screening mAbs specific for G–protein coupled receptors as exemplified by using epitope tagged BLR1–transfected 293 cells and solid–phase cell ELISA", *Biochemical and Biophysical Research Communications*, 196(3):1496–1503 (1993).*

Boring, L., et al., "Decreased lesion formation in CCR2–/–mice reveals a role for chemokines in the initiation of atherosclerosis," *Nature*, 394(27):894–897 (1998).*

Ylä–Herttuala, S., et al., "Expression of monocyte chemoattractant protein 1 in macrophage–rich areas of human and rabbit atherosclerotic lesions," *Proc. Natl. Acad. Sci.*, USA, 88:5252–5256 (1991).*

Taubman, M.B., et al., "JE mRNA Accumulates Rapidly in Aortic Injury and in Platelet–Derived Growth Factor–Stimulated Vascular Smooth Muscle Cells," *Circulation Research* 70(2):314–325 (1992).

Feng, A., et al., "Red Wine Inhibits Monocyte Chemotactic Protein–1 Expression and Modestly Reduces Neointimal Hyperplasia After Balloon Injury in Cholesterol–Fed Rabbits," *Circulation* 100:2254–2259 (1999).

Lukacs, N.W., et al., "Production of Monocyte Chemoattractant Protein–1 and Macrophage Inflammatory Protein–1α by Inflammatory Granuloma Fibroblasts," *American Journal of Pathology*, 144(4):711–718 (1994).

Koch, A.E., et al., "Enhanced Production of Monocyte Chemoattractant Protein–1 in Rheumatoid Arthritis," *The Jour. of Clin. Invest.*, 90:772–779 (1992).

Harigai, M., et al., "Monocyte Chemoattractant Protein–1 (MCP–1) in Inflammatory Joint Diseases and Its Involvement in the Cytokine Network of Rheumatoid Synovium," *Clin. Immun. and Immunopathology*, 69(1):83–91 (1993).

Villiger, P.M., et al., "Production of Monocyte Chemoattractant Protein–1 by Inflamed Synovial Tissue and Cultured Synoviocytes," *J. Immunol.* 149(2):722–727 (1992).

Reinecker, H.C., et al., "Monocyte–Chemoattractant Protein 1 Gene Expression in Intestinal Epithelial Cells and Inflammatory Bowel Disease Mucosa," *Gastroenterology*, 108(1):40–50 (1995).

Nelken, N.A., et al., "Monocyte Chemoattractant Protein–1 in Human Atheromatous Plaques," *J. Clin. Invest.*, 88:1121–1127 (1991).

Grewal, I.S., et al., "Transgenic Monocyte Chemoattractant Protein–1 (MCP–1) in Pancreatic Islets Produces Monocyte–Rich Insulitis Without Diabetes," *J. Immunol.*, 159:401–408 (1997).

Yu, X., et al., "Elevated expression of monocyte chemoattractant protein 1 by vascular smooth muscle cells in hypercholesterolemic primates," *Proc. Natl. Acad. Sci.*, USA, 89:6953–6957 (1992).

Berman, J.W., et al., "Localization of Monocyte Chemoattractant Peptide–1 Expression in the Central Nervous System in Experimental Autoimmune Encephalomyelitis and Trauma in the Rat," *J. Immunol.*, 156:3017–3023 (1996).

Lukacs, N.W., et al., "The Production of Chemotactic Cytokines an Allogenic Response," *Amer. Jour. of Pathology*, 143(4):1179–1188 (1993).

Christensen, P.J., et al., "Characterization of the Production of Monocyte Chemoattractant Protein–1 and IL–8 in an Allogeneic Immune Response," *The Journal of Immunology*, 151(3):1205–1213 (1993).

Rand, M.L., et al., "Inhibition of T Cell Recruitment and Cutaneous Delayed–Type Hypersensitivity–Induced Inflammattion with Antibodies to Monocyte Chemoattractant Protein–1," *Amer. Jour. of Pathology*, 148(3):855–864 (1996).

Jones, M.L., and Warren, J.S., "Monocyte Chemoattractant Protein 1 in an Rat Model of Pulmonary Granulomatosis," *Laboratory Investigation*, 66(4):498–503 (1992).

Lloyd, C.M., et al., "Role of MCP–1 and RANTES in inflammation and progression to fibrosis during murine crescentic nephritis," *Journal of Leukocyte Biology*, 62:676–680 (1997).

Flory, C.M., et al., "Pulmonary Granuloma Formation in the Rat is Partially Dependent on Monocyte Chemoattractant Protein 1," *Laboratory Invest.*, 69(4):396–404 (1993).

Jones, M.L., et al., "Potential Role of Monocyte Chemoattractant Protein 1/JE In Monocyte/Macrophage–Dependent IgA Immune Complex Alveolitis in the Rat," *J. Immunol.*, 149(6):2147–2154 (1992).

Gu, L., et al., "Absence of Monocyte Chemoattractant Protein–1 Reduces Atherosclerosis in Low Density Lipoprotein Receptor–Deficient Mice," *Molecular Cell*, 2(2):275–281 (1998).

Tesch, G.H., et al., "Monocyte chemoattractant protein–1 promotes macrophage–mediated tubular injury, but not glomerular injury, in nephrotoxic serum nephritis," *J. Clin. Invest.*, 103(1):73–80 (1999).

Lu, B., et al., "Abnormalities in Monocyte Recruitment and Cytokine Expression in Monocyte Chemoattractant Protein 1–deficient Mice," *J. Exp. Med.*, 187(4):601–608 (1998).

Rutledge, B.J., et al., "High Level Monocyte Chemoattractant Protein–1 Expression in Transgenic Mice Increases Their Susceptibility to Intracellular Pathogens," *J. Immunol.*, 155:4838–4843 (1995).

Gunn, M.D., et al., "Monocyte Chemoattractant Protein–1 Is Sufficient for teh Chemotaxis of Monocytes and Lymphocytes in Transgenic Mice but Requires and Additional Stimulus for Inflammatory Activation," *J. Immunol., 158:376–383* (1997).

Chensue, S.W., et al., "Role of Monocyte Chemoattractant Protein–1 (MCP–1) in Th1 (Mycobacterial) and Th2 (Schistosomal) Antigen–Induced Granuloma Formation," *J. Immunol.*, 157:4602–4608 (1996).

Lukacs, N.W., et al., "Differential Recruitment of Leukocyte Populations and Alteration of Airway Hyperreactivity by C–C Family Chemokines in Allergic Airway Inflammation," *J. Immunol.*, 158:4398–4404 (1997).

Tang, W.W., et al., "Chemokine Expression in Experimental Tubulointerstitial Nephritis," *J. Immunol.*, 159:870–876 (1997).

Fujinaka, H., et al., "Suppression of Anti–Glomerular Basement Membrane Nephritis by Administration of Anti–Monocyte Chemoattractant Protein–1 Antibody in WKY Rats," *Jour. of the Amer. Soc. of Nephrology*, 8:1174–1178 (1997).

Lloyd, C.M., et al., "RANTES and Monocyte Chemoattractant Protein–1 (MCP–1) Play an Important Role in the Inflammatory Phase of Crescentic Nephritis, but Only MCP–1 Is Involved in Crescent Formation and Interstitial Fibrosis," *J. of Exp. Med.*, 185(7):1371–1380 (1997).

Furukawa, Y., et al., "Anti–Monocyte Chemoattractant Protein–1/Monocyte Chemotactic and Activating Factor Antibody Inhibits Neointimal Hyperplasia in Injured Rat Carotid Arteries," *Circulation Research*, 84:306–314 (1999).

Zisman, D.A., et al., "MCP–1 Protects Mice in Lethal Endotoxemia," *J. Clin. Invest.*, 99(12):2832–2836 (1997).

Schimmer, R.C., et al., "Streptococcal Cell Wall–Induced Arthritis: Requirements for IL–4, IL–10, IFN–γ, and Monocyte Chemoattractant Protein–1," *J. Immunol.*, 160:1466–1471 (1998).

Ogata, H., et al., "The Role of Monocyte Chemoattractant Protein–1 (MCP–1) in the Pathogenesis of Collagen–Induced Arthritis in Rats," *J. Pathol.*, 182:106–114 (1997).

Huffnagle, G.B., et al., "The Role of Monocyte Chemotactic Protein–1 (MCP–1) in the Recruitment of Monocytes and $CD4^+$ T Cells During a Pulmonary *Cryptococcus Neoformans* Infection," *J. Immunol.*, 155:4790–4797 (1995).

Gong, J., et al., "AN Antagonist of Monocyte Chemoattractant Protein 1 (MCP–1) Inhibits Arthritis in the MRL–1pr Mouse Model," *J. Exp. Med., 186(1):131–137* (1997).

Boring, L., et al., "Impaired Monocyte Migration and Reduced Type 1 (Th1) Cytokine Responses in C–C Chemokine Receptor 2 Knockout Mice," *J. Clin. Invest., 100(10):2552–2561* (1997).

Kuziel, W.A., et al., "Severe reduction in leukocyte adhesion and monocyte extravasation in mice deficient in CC chemokine receptor 2," *Proc. Natl. Acad. of Sci.*, USA 94(22):12053–12058 (1997).

Kurihara, T., et al., "Defects in Macrophage Recruitment and Host Defense in Mice Lacking the CCR2 Chemokine Receptor," *J. Exp. Med.*, 186(10):1757–1762 (1997).

Jiang, Y., et al., "Chemokine receptor expression in cultured glia and rat experimental allergic encephalomyelitis," *J. Neuroimmunology*, 86:1–12 (1998).

Chuntharapai, et al., "Generation of Monoclonal Antibodies to Chemokine Receptors", *Methods in Enzymology* 288: 15–27 (1997).

* cited by examiner

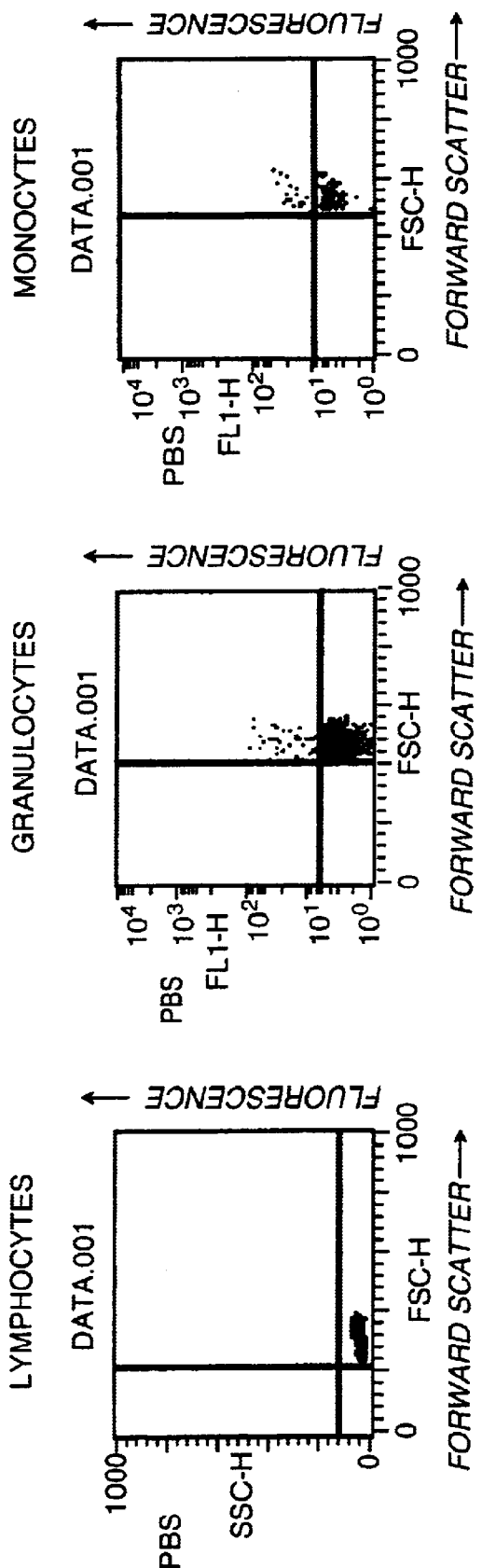

1     DVVMTQTPLT LSVTVGHPAS ISCKSSQSLL DSDGKTFLNW LLQRPGQSPK

51    RLIYLVSKLD SGVPDRFTGS GSGTDFTLKI SRVEAEDLGV YYCWQGTHFP

101   YTFGGGTKLE IK

Figure 7

1    EVQLVESGGG LVQPKGSLKL SCAASGFSFN AYAMNWVRQA PGKGLEWVAR

51   IRTKNNNYAT YYADSVKDRY TISRDDSESM LFLQMNNLKT EDTAMYYCVT

101  FYGNGVWGTG TTVTVSS

Figure 8

Chothia Canonical Classes

L1 (16 amino acids) = Class 4
Key residues: 2(V), 25(SA), 29(L), 33(L), 71(F)

L2 (7 amino acids) = Class 1
Key residues: 48(IV), 51(AT), 52(ST), 64(G)

L3 (9 amino acids) = Class 1
Key residues: 90(QNH), 95(P)

Martin Canonical Classes

L1 (16 amino acids) = Class 4/16A
Key residues: 2(V), 4(ML), 23(C), 25(SSP), 26(SN), 27(Q), 29(LI), 30A(HL), 30B(S), 30C(NDS), 30D(G), 32(YS), 33(LF), 34(HEN), 35(W), 51(V), 71(F), 88(C), 90(Q), 92(TS), 93(H)

L2 (7 amino acids) = Class 1/7A
Key residues: 23(C)

L3 (9 amino acids) = Class 1/9A
Key residues: 2(IVL), 3(VQLE), 4(ML), 28(SNDTE), 30(DYLVISNFGHT), 31(SNTKG), 32(FYNAHSR), 33(MLVIF), 88(C), 89(QSGFL), 90(QNH), 91(NFGSRDHTYV), 92(NYWTSRQHAD), 93(ENGHTSRAQHAD), 94(DYTVLHNNIWPS), 95(P), 96(PLYRIWF), 97(T), 98(F)

Figure 9

Chothia Canonical Classes

H1 (5 amino acids) = Class 1
Key residues: 24(AVG), 26(G), 27(FY)

H2 (19 amino acids) = Class 4
Key residues: 54(S), 55(Y), 71(R)

Martin Canonical Classes

H1 (5 amino acids) = Class 1/10A
Key residues: 2(VIG), 4(LG), 20(LIMV), 22(C),
24(TAGVS), 26(G), 29(IFLS),
32(IHYFTNCED), 33(AWGTLV),
34(IVMW), 35(HENQSYT), 36(W),
48(IMLV), 51(LIVTSN),
69(ILFMV), 78(ALVYF), 80(LM),
90(YF), 92(C), 94(RKGSNH),
102(YHVISDG).

H2 (19 amino acids) = Class ?/12B
Key residues: 47(W), 50(RQ), 51(I), 59(Y), 69(I),
71( R), 78(LV)

Figure 10

```
CDRs                  ======L1========          ==L2===                              ======L3======

Kabat       1111111111222222222233333333334444444444555555555566666666667777777777888888888899999999990000000000
Numbers     1234567890123456789012345678901234567ABCDEF8901234567890123456789012345678901234567890123456789012345ABCDEF67890123456A7

1D9 Vκ      DVVMTQTPLTLSVTVGHPASISCKSSQSLLDS-DGKTFLNWLLQRPGQSPKRLIYLVSKLDSGVPDRFTGSGSGTDFTLKISRVEAEDLGVYYCWQGTHFP------YTFGGGTKLEI-K
HF-21/28 Vκ ......S...S.P..L.Q......VH...N.Y...FQ.........K..NR......S..................V.....M....W.     F...Q..R....

1D9RK_A Vκ  DVVMTQSPLSLPVTLGQPASISCKSSQSLLDS-DGKTFLNWFQQRPGQSPRRLIYLVSKLDSGVPDRFSGSGSGTDFTLKISRVEAEDVGVYYCWQGTHFP------YTFGQGTRLEI-K
1D9RK_B Vκ  DVVMTQSPLSLPVTLGQPASISCKSSQSLLDS-DGKTFLNWLLQRPGQSPRRLIYLVSKLDSGVPDRFSGSGSGTDFTLKISRVEAEDVGVYYCWQGTHFP------YTFGQGTRLEI-K
1D9RK_C Vκ  DVVMTQSPLSLPVTLGQPASISCKSSQSLLDS-DGKTFLNWLLQRPGQSPRRLIYLVSKLDSGVPDRFSGSGSGTDFTLKISRVEAEDVGVYYCWQGTHFP------YTFGQGTRLEI-K
1D9RK_D Vκ  DVVMTQSPLSLPVTLGHPASISCKSSQSLLDS-DGKTFLNWLLQRPGQSPRRLIYLVSKLDSGVPDRFSGSGSGTDFTLKISRVEAEDVGVYYCWQGTHFP------YTFGGGTRLEI-K
```

Key

| | |
|---|---|
| 1D9 Vκ | Mouse 1D9 Vκ region |
| HF-21/28 Vκ | Chosen human framework acceptor Vκ region sequence with mismatches to the 1D9 Vκ region highlighted. |
| 1D9RK_A Vκ | CDR grafted 1D9 Vκ region, with no back mutations but with the added human lysine residue at position 107 (i.e. 107K). |
| 1D9RK_B Vκ | CDR grafted 1D9 Vκ region, with back mutations at F36L and Q37L, and the additional 107K insertion. |
| 1D9RK_C Vκ | CDR grafted 1D9 Vκ region, with back mutations at F36L, Q37L and Q100G, and the additional 107K insertion. |
| 1D9RK_D Vκ | CDR grafted 1D9 Vκ region, with back mutations at F36L, Q37L, Q100G and Q17H, and the additional 107K insertion. |

Figure 11

```
CDRs                                                             ----=H1===                                  =========H2=======                                                                              ======H3========
          1         2         3          4         5         6         7         8         9         1                                        1
Kabat                                                                                                      0                                    0                                               1
Numbers  1234567890123456789012345678901234 5AB6789012345678901 2ABC345678901234567890123456789012345 67890123456789 0ABC-1JK1234567890123

1D9      EVQLVESGGGLVQPKGSLKLSCAASGFSFNAYAMN---WVRQAPGKGLEWVARIRTKNNNYATYYADSVKDRYTISRDDSESMLFLQMNNLKTEDTAMYYCVTFYGN------GVWGTGTTVTVSS
4B4'CL Vн .............K.G...R.......T.SNAW.S .................G..KS.TDGGT.D..AP..G.F......KNT.Y...S......V...T.DSLPPH R...Q..L......
1D9RHA Vн EVQLVESGGGLVKPGGSLRLSCAASGFSFNAYAMN---WVRQAPGKGLEWVGRIRTKNNNYATYADSVKDRFTISRDDSKNTLYLQMNSLKTEDTAVYYCTTFYGN------GVWGQGTLVTVSS
1D9RHB Vн EVQLVESGGGLVKPGGSLRLSCAASGFSFNAYAMN---WVRQAPGKGLEWVGRIRTKNNNYATYADSVKDRFTISRDDSKNTLYLQMNSLKTEDTAVYYCTTFYGN------GVWGQGTLVTVSS
1D9RHC Vн EVQLVESGGGLVKPGGSLRLSCAASGFSFNAYAMN---WVRQAPGKGLEWVARIRTKNNNYATYADSVKDRYTISRDDSKNTLYLQMNSLKTEDTAVYYCTTFYGN------GVWGQGTLVTVSS
1D9RHD Vн EVQLVESGGGLVKPGGSLRLSCAASGFSFNAYAMN---WVRQAPGKGLEWVARIRTKNNNYATYADSVKDRYTISRDDSKNTLYLQMNSLKTEDTAVYYCVTFYGN------GVWGQGTLVTVSS
```

Key

1D9 $V_H$          Mouse 1D9 $V_H$ region.
4B4'CL $V_H$       Chosen human framework acceptor $V_H$ region sequence with mismatches to the 1D9 $V_H$ region highlighted.
1D9RH$_A$ $V_H$    CDR grafted 1D9 $V_H$ region, with no back mutations.
1D9RH$_B$ $V_H$    CDR grafted 1D9 $V_H$ region, with back mutations at T28S and S30N.
1D9RH$_C$ $V_H$    CDR grafted 1D9 $V_H$ region, with back mutations at T28S, S30N, G49A and F67Y.
1D9RH$_D$ $V_H$    CDR grafted 1D9 $V_H$ region, with back mutations at T28S, S30N, G49A, F67Y and T93V.

Figure 12

Amino Acid Sequence

| Sequence Name | Identical Residues | Amino Acid Sequence |
|---|---|---|
| 1D9 V$_\kappa$ | 114 | DVVMTQTPLTLSVTVGHPASISCKSSQSLLDS-DGKTFLNWLLQRPGQSPKRLIYLVSKLDSGVPDRFTGSGSGTDFTLKISRVEAEDLGVYYCWQGTHFP |
| 70/3 | 97 | ...........I.Q...................................Y..................................................... |
| 70/1 | 94 | ...........I.Q.........................Y...N...Y....................................................V... |
| 70/2 | 82 | ....XLHS...I.Q.........................Y...N...Y........V.P..................Y.............XP.........X.M.D... |
| V-1B | 76 | ...S.P.SL.DQ........R......VH..N.N.Y.Y.Y..K........L...R..NRF..........S....................F.F.....V. |
| V-1C | 75 | ...S.P.SL.DQ........R......IVH.N.N.Y.E.Y..K........L...K..NRL..........S....................F.S.V. |
| V-1A/K5.1/K5.1 | 75 | ...S.P.SL.DQ........R......VH..N.N.Y.H.Y..K........L...K..NRF..........S....................F.S.S.V. |
| V-1C/V1A5/K1A5 | 74 | .L..S.P.SL.DQ........R......IVH.N.N.Y.E.Y..K........L...K..NRF..........S....................F.S.V. |
| K1B.1 | 73 | .A.....S.P.SL.DQ........R......EN..N.N.Y..Y..K......QL..R..NRF..L.....S....................F.L.V.V. |
| 1F | 71 | .LL....F.P.SL.DQ........S......VH..N.NYY.E.H..KS..LQL..E...RH..........S...............P.........F....L. |
| 24A | 68 | .I....AAFSNP..L.TS........R..K...H...S.N.Y.Y.F..K....QL..YI.N.A.........S.......................R...........V....M.LEY. |
| 167/24 | 67 | .I.I.DE.SNP..S.ESV......R..K...YK.....Y...F.......QL....M.TRA...S......S........................E...K..V....Q.LVEY. |
| 24B | 66 | .I....AAFSNP..L.TS........R..K...H...N.I.Y.Y.Y..K....QL..QM.N.A.........SS......................R...............V....A.NLEL. |

Figure 13

Amino Acid Sequence

| Sequence Name | Identical Residues | Amino Acid Sequence |
|---|---|---|
| 1D9 V_H | 117 | EVQLVESGGGLVQPKGSLKLSCAASGFSFNAYAMN--WVRQAPGKGLEWVARIRTKNNYATYYADSVKDRYTISRDDSESMLFLQMNNLKTEDTAMYYCVTF |
| MRL-RF24BG | 86 | ...VWWRM.................................S.SS.................Q..Y............I- |
| V(H)22.1 | 70 | ..K.E.......G..M....V......T.SN.W.S........S.E.........Q.L.SD....H.E....G.F.......K.SVY.......RA...GI..TG- |
| V11/pBV19B4 | 66 | ..K.........G..R....T...T.TD.Y.S........P..A...LGF.N.A.G.T.E.SA....G.F....N.Q.I.Y....T.RA..S.T...AR- |
| Vh7183(Vh69.1) | 66 | ..K.........K.G.........T.SS.T.S........S.E.R.....T.SS--GGSY...P.......G.F....NAKNT.Y...SS..S........TR- |
| VH10-19 | 65 | D.K.........K.G.........T.SS...S........T.E.R.....T.SS--GGSY...P.......G.F....NAKNT.Y...SS..S........TR- |
| VHE4-psi | 65 | .L..........G..R........T.SS...S........T.E.R.....A.S.--DGSFI.XP.T.....G.F....NAKNT.Y...SS.RY........LR- |
| V(H)50.1 | 65 | ..K.........G......T.....T.SD.Y.Y........T.E.R.....Y.SN--GGGS......P.T..G.F....NAKNT.Y...SR..S........AR- |
| V3 | 65 | ..K........GA..R....S....T.TD.Y..........HRP..P....L.L..N.A.G.I.E.SA.M.G.F....N.Q.I.Y....T.S..S.T....ARD |
| V1/pBV132 | 64 | ..K.........G..R....T....T.SDFY.E........P...R....I.AS.N.A.D.T.E.SA....G.FIV...T.Q.I.Y....A.RA....I...AR- |
| VH283 | 64 | ..M.........K.G..........T.SS.T.S........T.E.R.....T.SS--GGGN...P.......G.F....NAKNN.Y...SS.RS.....L..AR- |
| V(H)37.1 | 63 | ..K.........K.G.....T....T.SS.G.S........T.E.R.....T.SG--GGSY...P.......G.F....NAKNN.Y...SS.RS.....L..AR- |
| V13 | 61 | ..K.M.......GA..R....E...T.TD.Y.S........L.R.SP.L.L..N.A.G.T.E.SA....G.F.......T.RA.AS.T...AKD |
| V-H_441/V441 | 59 | ..K.L.......G...........D.SR.W.S.........IGE.NP--DSSTIN.TP.L..KFI..NAKNT.Y...SKVRS....L..AR- |
| 68-5N | 59 | -----.......G............T.SS.G.S........T.D.R..L..T.NS--.GGS...P.......G.F....NAKNT.Y...SS..S........AR- |
| 76-1BG/VH7183.9 | 58 | -----.......K.G..........T.SS...S........T.E.R.....T.SS--GGSY...P.......G.F....NAKNT.Y...SS.RS........AR- |
| 61-1P | 58 | -----.......G..R.........T.SSFG.H........E.........Y.SS--GSSTI....T...G.F....NPKNT......TS.RS........AR- |
| 57-1M/VH7183.12 | 58 | -----.......K.G..........T.SS...S........T.E.R.....S.S---SGGS......P.....G.F....NARNI.Y...SS.RS........AR- |
| V(H)55 | 56 | ..K.L......G..N..........D.SR.W.S.........A......Q.IGE.NP--GSSTIN.TP.L..KFI..NAKNT.Y...SKVRS....L..AR- |
| VH7183.13 | 55 | -----.......K.G..........T.SS.T.S........T.E.R.....Y.SN--GGGS......P.T..G.F....NAKNT.Y...SS..S........AR- |

Figure 14

Amino Acid Sequence

| Name | ID | Sequence |
|------|-----|----------|
| | | SCSCCCscsCccccccscccCCscssscscs sccccccCCcccscccCCCCCCCCCsCCCCCCCCcscsCCCCCCCCsCCCCCCCCCscccccCCcccccsc ccCccccscs s |
| | | 1 2 3 4 5 6 7 8 9 1 |
| | | 0 |
| | | 1234567890123456789012345678ABCDEF890123456789012345678901234567890123456789012345ABCDEF67890123456A7 |
| | | v v ======L1========vv vvvv=L2=== v vv v ====L3=======v |
| 1D9 V$_K$ | 100.0 | DVVMTQTPLTLSVTVGHPASISCKSSQSLLDS-DGKTFLNWLLQRPGQSPKRLIYLVSKLDSGVPDRFTGSGSGTDFTLKISRVEAEDLGVYYCWQGTHFP------YTFGGGTKLEI-K |
| 036521 | 90.4 | .IQL..S.......I.Q................Y.............R...K..NR........D.........— FPQ..... |
| IL66 | 78.8 | ...L...S.P..L.Q......R.D...VY......Y..YQ........R...K..NR............V........M....W. G...Q...V. |
| RPM16410 | 78.8 | .....S..S.P..L.Q......R......VY...N.Y..FQ........R...K..NR............V........M...WS W...Q...V. |
| ZM1-1 | 78.8 | ...V...S..S.P..L.Q......R..L..V....N.Y..F.........R...QL.SR...........V........M....W. I....Q..R. |
| VLClone 54 | 78.1 | ....I...S..S.P..L.Q......R..G.VY...D.Y..FQ........R...K..NR..........S.G........M....W. ....Q..... |
| HF-21/28 | 79.3 | .......S..S.P..L.Q......R......VH...N.Y..FQ........R...K..NR............S......V........M....W. F....Q..R. |
| SpA2-08 | 77.9 | AEEL...S..S.P..L.Q......R......L....D.Y..YQ........R...K..NR..........S........V........M.A..W. .....Q..... – |
| IL30 | 77.9 | ...L...S..S......L.Q......R.T.I.VF..N.Y..FQ.T.H..R...R..NR..........S........V........M....W. .....Q..... |
| HUNVK | 77.9 | .......S..S.P..L.Q......R......VH...N.Y..FQ........R...R..NR..........S........V.I......M.A..W. L....Q..R. T |
| O-81 | 75.7 | .......S..S.P..L.Q......R......VH...N.Y..FQ........R...R..NR..........S........V.L......M.H..WSP I....Q..R. |
| ToP309 | 74.8 | .I.....S.....P.Q........H....Y.Y.Y..K...P.QL..E..NRF.........S........V........M.SVQL.R F...P...VD. |
| ToP218 | 74.8 | .I.....S.....P.Q........H....Y.Y.Y..K...P.QL..E..NRF.........S........V........M.SIQL.R F...P...VD. |
| SpA3-02 | 76.1 | AEEL...S..S.P..L.Q......R......VY...N.Y..FQ........R...K..NR.........S........V........M....W. K....Q..V. |
| IL37 | 75.2 | .......S..S.P..L.QS.....T......VYT..IY..FQ........R...FK.NR.........S........VAI.......M....W. G...Q...V. |
| CUM | 73.9 | .I.....S.P..P.E..........R.....G..N.Y..Y.KA..QL.TL.YRA..........S...Q............V......M.RLEI. ....Q..... R |
| VLClone 51 | 74.6 | .......S.P..L.Q......R..RG.VH...N.Y..FQ........R...K..NR............A........V........M.SI.W. W...Q...V. |
| IL20 | 75.2 | .I.L...S..S.P..L.Q......R...N.VY...N.Y...FQ........R...K..NR..........S.S.......V.I......M...RW. ....E..... |

Figure 15

| Name | ID | Surface | Core | Kabat CDR | FR | FR Surface | Core FR | FR Near CDR | Vernier | $V_K$ | J Chain | Closest Human Germline Gene | L1 Len | L2 Len | L3 Len | L1 Class | L2 Class | L3 Class |
|---|---|---|---|---|---|---|---|---|---|---|---|---|---|---|---|---|---|---|
| 1D9 $V_K$ | 100.0 | 30 | 82 | 32 | 82 | 22 | 60 | 33 | 14 | 100 | 14 | | 16 | 7 | 9 | 4 | 1 | 1 |
| 036521 | 90.4 | 27 | 76 | 28 | 75 | 19 | 56 | 31 | 13 | 90 | 13 | DPK19-A1+ | Same | Same | Same | Same | Same | Same |
| II.66 | 78.8 | 25 | 67 | 22 | 69 | 18 | 52 | 30 | 13 | 80 | 12 | DPK18-A17+ | Same | Same | Same | Same | Same | Same |
| RPMI6410 | 78.8 | 25 | 67 | 22 | 69 | 18 | 52 | 30 | 13 | 79 | 12 | DPK18-A17+ | Same | Same | Same | ? | Same | ? |
| ZM1-1 | 78.8 | 25 | 66 | 21 | 68 | 18 | 52 | 30 | 13 | 79 | 12 | DPK18-A17+ | Same | Same | Same | Same | Same | Same |
| VL clone 54 | 78.1 | 25 | 66 | 21 | 68 | 18 | 52 | 30 | 13 | 79 | 12 | DPK18-A17+ | Same | Same | Same | Same | Same | Same |
| HF-21/28 | 79.3 | 24 | 66 | 21 | 68 | 18 | 52 | 30 | 13 | 78 | 12 | DPK18-A17+ | Same | Same | Same | Same | Same | Same |
| SpA2-08 | 77.9 | 24 | 65 | 21 | 68 | 18 | 51 | 30 | 13 | 77 | 12 | DPK18-A17+ | Same | Same | Same | ? | Same | Same |
| II.30 | 77.9 | 24 | 65 | 21 | 68 | 18 | 51 | 30 | 12 | 77 | 12 | DPK18-A17+ | Same | Same | Same | Same | Same | Same |
| HUNVK | 77.9 | 24 | 65 | 21 | 68 | 18 | 51 | 30 | 12 | 77 | 12 | DPK18-A17+ | Same | Same | Same | Same | Same | Same |
| O-81 | 75.7 | 24 | 65 | 21 | 68 | 18 | 51 | 30 | 12 | 77 | 12 | DPK18-A17+ | Same | Same | 10 | Same | Same | ? |
| ToP309 | 74.8 | 24 | 64 | 20 | 68 | 18 | 51 | 29 | 12 | 76 | 12 | DPK12-A2+ | Same | Same | 10 | ? | Same | ? |
| ToP218 | 74.8 | 24 | 64 | 20 | 68 | 18 | 51 | 29 | 12 | 76 | 12 | DPK12-A2+ | Same | Same | 10 | ? | Same | ? |
| SpA3-02 | 76.1 | 24 | 63 | 20 | 68 | 18 | 51 | 29 | 12 | 76 | 12 | DPK18-A17+ | Same | Same | Same | ? | Same | Same |
| II.37 | 75.2 | 24 | 63 | 20 | 68 | 18 | 51 | 29 | 12 | 76 | 12 | DPK18-A17+ | Same | Same | Same | Same | Same | Same |
| CUM | 73.9 | 24 | 63 | 20 | 68 | 18 | 50 | 29 | 12 | 75 | 12 | DPK36-Chr22 | 4 | 17 | Same | Same | 3 | Same | Same |
| VL clone 51 | 74.6 | 24 | 62 | 20 | 67 | 18 | 50 | 29 | 12 | 75 | 12 | DPK18-A17+ | Same | Same | Same | ? | Same | Same |
| II.20 | 75.2 | 23 | 62 | 20 | 67 | 18 | 50 | 29 | 12 | 75 | 12 | DPK18-A17+ | Same | Same | Same | ? | Same | Same |

| Name | ID | All | Surface | Core | Kabat CDR | FR | FR Surface | Core FR | FR Near CDR | Vernier | $V_H$ | J Chain | Closest Human Germline Gene | H1 Size | H2 Size | H3 Size | H1 Class | H2 Class |
|---|---|---|---|---|---|---|---|---|---|---|---|---|---|---|---|---|---|---|
| 1D9 $V_H$ | 100.0 | 117 | 29 | 84 | 30 | 87 | 21 | 65 | 30 | 16 | 100 | 17 | | 5 | | 6 | 1 | 4 |
| 030094 | 67.7 | 86 | 19 | 67 | 15 | 72 | 17 | 57 | 26 | 12 | 75 | 13 | DP-29-122+ | Same | Same | 16 | Same | Same |
| N51P8 | 68.3 | 86 | 18 | 66 | 15 | 72 | 16 | 57 | 25 | 12 | 75 | 13 | DP-29-122+ | Same | Same | 15 | ? | Same |
| IW2-91 | 67.5 | 85 | 18 | 65 | 15 | 72 | 16 | 56 | 25 | 12 | 75 | 12 | DP-29-122+ | Same | Same | 15 | Same | Same |
| H2-46 | 66.7 | 84 | 18 | 65 | 15 | 72 | 16 | 56 | 25 | 12 | 75 | 12 | DP-29-122+ | Same | Same | 15 | Same | Same |
| 039158 | 72.2 | 83 | 17 | 64 | 15 | 71 | 15 | 56 | 25 | 12 | 74 | 12 | DP-29-122+ | | | | | |
| 038064 | 65.6 | 82 | 17 | 64 | 14 | 71 | 15 | 56 | 25 | 11 | 74 | 12 | VH26Rabbitts+ | | | | | |
| 038062 | 64.6 | 82 | 17 | 63 | 14 | 71 | 15 | 56 | 25 | 11 | 73 | 12 | VH26Rabbitts+ | | | | | |
| 32.B9 | 64.6 | 82 | 17 | 63 | 14 | 71 | 15 | 56 | 25 | 11 | 72 | 12 | VH26Rabbitts+ | Same | 17 | 19 | Same | 3 |
| 038062 | 64.6 | 82 | 17 | 63 | 14 | 70 | 15 | 56 | 25 | 11 | 72 | 12 | VH26Rabbitts+ | | | | | |
| 034514 | 69.8 | 81 | 17 | 63 | 14 | 70 | 15 | 55 | 25 | 11 | 72 | 12 | VH26Rabbitts+ | | | | | |
| 038066 | 65.3 | 81 | 16 | 63 | 14 | 70 | 15 | 55 | 25 | 11 | 71 | 12 | VH26Rabbitts+ | | | | | |
| 035365 | 65.9 | 81 | 16 | 63 | 14 | 70 | 15 | 55 | 25 | 11 | 71 | 12 | VH26Rabbitts+ | | | | | |

Figure 18A

| Name | ID | All | Surface | Core | Kabat CDR | FR | FR Surface | Core FR | FR Near CDR | Vernier | $V_H$ | J Chain | Closest Human Germline Gene | H1 Size | H2 Size | H3 Size | H1 Class | H2 Class |
|---|---|---|---|---|---|---|---|---|---|---|---|---|---|---|---|---|---|---|
| Hb-5 | 69.2 | 81 | | | | | | | | | | | | | | | | |
| 4G12 | 64.8 | 81 | 16 | 63 | 14 | 69 | 15 | 55 | 25 | 11 | 71 | 12 | VH26Rabbitts+ | Same | 17 | 16 | Same | 3 |
| VH clone 39 | 66.7 | 80 | 16 | 63 | 14 | 69 | 14 | 55 | 25 | 11 | 71 | 12 | VH26Rabbitts+ | Same | 17 | 11 | Same | 3 |
| 040094 | 62.5 | 80 | 16 | 63 | 14 | 69 | 14 | 55 | 25 | 11 | 71 | 12 | LSG3.1 | | | | | |
| VH clone 18 | 63.0 | 80 | 16 | 63 | 13 | 69 | 14 | 55 | 25 | 11 | 71 | 12 | VH26Rabbitts+ | Same | 17 | 18 | Same | 3 |
| UB1-24 | 67.2 | 80 | 16 | 63 | 13 | 69 | 14 | 55 | 25 | 11 | 71 | 12 | DP-31-V39P+ | Same | 17 | 10 | Same | 3 |
| 029764 | 64.5 | 80 | 16 | 63 | 13 | 69 | 14 | 55 | 25 | 11 | 71 | 12 | VH26Rabbitts+ | Same | 17 | 15 | Same | 3 |
| IW2-105 | 64.5 | 80 | 16 | 63 | 13 | 69 | 14 | 55 | 25 | 11 | 71 | 12 | LSG3.1 | Same | Same | 13 | Same | ? |
| UB1-17 | 65.0 | 80 | 16 | 63 | 13 | 69 | 14 | 55 | 25 | 11 | 71 | 11 | LSG3.1 | Same | Same | 12 | Same | ? |
| VH clone 41 | 66.1 | 80 | 16 | 62 | 13 | 69 | 14 | 55 | 25 | 11 | 71 | 11 | VH26Rabbitts+ | Same | 17 | 12 | Same | 3 |
| 4B4*CL | 67.2 | 80 | 16 | 62 | 13 | 68 | 14 | 55 | 25 | 11 | 71 | 11 | LSG3.1 | Same | Same | 8 | Same | ? |
| M26 | 65.0 | 80 | 16 | 62 | 13 | 68 | 14 | 55 | 25 | 11 | 71 | 11 | LSG3.1 | Same | Same | 12 | Same | ? |

Figure 18B

| Kabat | # | FR or CDR | Mouse 1D9 $V_\kappa$ | Mouse κ-II | Human κ-II | Human Acceptor HF-21/28 (005056) | Surface or Core | 1D9 $RK_A$ | 1D9 $RK_B$ | Comment |
|---|---|---|---|---|---|---|---|---|---|---|
| 1 | 1 | FR1 | D | D* | D | | S | D | D | |
| 2 | 2 | | V | V | I* | | C | V | V | |
| 3 | 3 | | V | V | V* | | S | V | V | |
| 4 | 4 | | M | M | M | | C | M | M | |
| 5 | 5 | | T | T* | T | | C | T | T | |
| 6 | 6 | | Q | Q* | Q | | C | Q | Q | |
| 7 | 7 | | T | T | S | S | S | S | S | |
| 8 | 8 | | P | P | P | | c | P | P | |
| 9 | 9 | | L | L | L | | s | L | L | |
| 10 | 10 | | T | S | S | S | C | S | S | |
| 11 | 11 | | L | L | L* | | c | L | L | |
| 12 | 12 | | S | P | P | P | c | P | P | |
| 13 | 13 | | V | V* | V* | | c | V | V | |
| 14 | 14 | | T | S | T | | c | T | T | |
| 15 | 15 | | V | L | P | L | s | L | L | |
| 16 | 16 | | G | G | G | | c | G | G | |
| 17 | 17 | | H | D | E | Q | c | Q | Q | |
| 18 | 18 | | P | Q | P | | s | P | P | |
| 19 | 19 | | A | A | A | | c | A | A | |
| 20 | 20 | | S | S* | S | | c | S | S | |
| 21 | 21 | | I | I* | I | | c | I | I | |
| 22 | 22 | | S | S* | S* | | C | S | S | |
| 23 | 23 | FR1 | C | C | C | | C | C | C | |
| 24 | 24 | CDR1 | K | R | R | R | s | K | K | |
| 25 | 25 | | S | S* | S* | | c | S | S | |
| 26 | 26 | | S | S* | S | | s | S | S | |
| 27 | 27 | | Q | Q | Q | | s | Q | Q | |
| 27A | 28 | | S | S | S | | s | S | S | |
| 27B | 29 | | L | L | L | | c | L | L | |
| 27C | 30 | | L | V | L | V | s | L | L | |
| 27D | 31 | | D | H | H | H | c | D | D | |
| 27E | 32 | | S | S | S | | s | S | S | |
| 27F | | | - | | x | | | - | - | |
| 28 | 33 | | D | N | D | | s | D | D | |
| 29 | 34 | | G | G* | G | | c | G | G | |
| 30 | 35 | | K | N | N | N | c | K | K | |
| 31 | 36 | | T | T | N | | c | T | T | |
| 32 | 37 | | F | Y* | Y | Y | c | F | F | |
| 33 | 38 | | L | L* | L | | c | L | L | |
| 34 | 39 | CDR1 | N | E | N | | c | N | N | |
| 35 | 40 | FR2 | W | W | W | | C | W | W | |
| 36 | 41 | | L | Y | Y | F | C | F | L | Δ1 |

Figure 19A

| Kabat | # | FR or CDR | Mouse 1D9 $V_\kappa$ | Mouse κ-II | Human κ-II | Human Acceptor HF-21/28 (005056) | Surface or Core | 1D9 $RK_A$ | 1D9 $RK_B$ | Comment |
|---|---|---|---|---|---|---|---|---|---|---|
| 37 | 42 | | L | L | L | Q | c | Q | L | Δ2 |
| 38 | 43 | | Q | Q* | Q | | c | Q | Q | |
| 39 | 44 | | R | K | K | | c | R | R | |
| 40 | 45 | | P | P* | P | | s | P | P | |
| 41 | 46 | | G | G* | G | | s | G | G | |
| 42 | 47 | | Q | Q | Q | | c | Q | Q | |
| 43 | 48 | | S | S* | S | | c | S | S | |
| 44 | 49 | | P | P* | P | | C | P | P | |
| 45 | 50 | | K | K | Q | R | c | R | R | |
| 46 | 51 | | R | L | L | | C | R | R | |
| 47 | 52 | | L | L* | L | | C | L | L | |
| 48 | 53 | | I | I* | I | | C | I | I | |
| 49 | 54 | FR2 | Y | Y | Y | | C | Y | Y | |
| 50 | 55 | CDR2 | L | K | L | | c | L | L | |
| 51 | 56 | | V | V | V | K | c | V | V | |
| 52 | 57 | | S | S | S | | c | S | S | |
| 53 | 58 | | K | N | N | | c | K | K | |
| 54 | 59 | | L | R | R | N | c | L | L | |
| 55 | 60 | | D | F | A | R | c | D | D | |
| 56 | 61 | CDR2 | S | S* | S | | s | S | S | |
| 57 | 62 | FR3 | G | G | G | | S | G | G | |
| 58 | 63 | | V | V | V | | C | V | V | |
| 59 | 64 | | P | P | P | | C | P | P | |
| 60 | 65 | | D | D* | D | | S | D | D | |
| 61 | 66 | | R | R | R | | C | R | R | |
| 62 | 67 | | F | F* | F | | C | F | F | |
| 63 | 68 | | T | S | S | S | C | S | S | |
| 64 | 69 | | G | G* | G | | C | G | G | |
| 65 | 70 | | S | S* | S | | C | S | S | |
| 66 | 71 | | G | G* | G | | C | G | G | |
| 67 | 72 | | S | S* | S | | s | S | S | |
| 68 | 73 | | G | G* | G | | C | G | G | |
| 69 | 74 | | T | T* | T | | C | T | T | |
| 70 | 75 | | D | D* | D | | C | D | D | |
| 71 | 76 | | F | F* | F | | C | F | F | |
| 72 | 77 | | T | T* | T | | c | T | T | |
| 73 | 78 | | L | L | L | | c | L | L | |
| 74 | 79 | | K | K | K | | c | K | K | |
| 75 | 80 | | I | I | I | | c | I | I | |
| 76 | 81 | | S | S | S | | c | S | S | |
| 77 | 82 | | R | R* | R | | s | R | R | |
| 78 | 83 | | V | V | V | | c | V | V | |
| 79 | 84 | | E | E | E | | s | E | E | |
| 80 | 85 | | A | A* | A | | c | A | A | |
| 81 | 86 | | E | E* | E | | s | E | E | |
| 82 | 87 | | D | D* | D | | c | D | D | |
| 83 | 88 | | L | L | V | V | c | V | V | |
| 84 | 89 | | G | G* | G | | c | G | G | |
| 85 | 90 | | V | V | V | | c | V | V | |
| 86 | 91 | | Y | Y* | Y | | c | Y | Y | |
| 87 | 92 | | Y | Y | Y | | C | Y | Y | |
| 88 | 93 | FR3 | C | C | C | | C | C | C | |

Figure 19B

| Kabat | # | FR or CDR | Mouse 1D9 $V_\kappa$ | Mouse κ-II | Human κ-II | Human Acceptor HF-21/28 (005056) | Surface or Core | 1D9 RK$_A$ | 1D9 RK$_B$ | Comment |
|---|---|---|---|---|---|---|---|---|---|---|
| 89 | 94 | CDR3 | W | F | M | | c | W | W | |
| 90 | 95 | | Q | Q* | Q | M | c | Q | Q | |
| 91 | 96 | | G | G | A | | c | G | G | |
| 92 | 97 | | T | T | L | | c | T | T | |
| 93 | 98 | | H | H | Q | | c | H | H | |
| 94 | 99 | | F | V | x | | s | F | F | |
| 95 | 100 | | P | P* | P | W | c | P | P | |
| 95A | | | - | P | R | | | - | - | |
| 95B | | | - | - | - | | | - | - | |
| 95C | | | - | - | - | | | - | - | |
| 95D | | | - | - | - | | | - | - | |
| 95E | | | - | - | - | | | - | - | |
| 95F | | | - | - | - | | | - | - | |
| 96 | 101 | | Y | Y | x | - | c | Y | Y | |
| 97 | 102 | CDR3 | T | T* | T | F | c | T | T | |
| 98 | 103 | FR4 | F | F* | F | | C | F | F | |
| 99 | 104 | | G | G | G | | c | G | G | |
| 100 | 105 | | G | G | Q | Q | c | Q | G | |
| 101 | 100 | | G | G | G | | c | G | G | |
| 102 | 106 | | T | T | T | | c | T | T | |
| 103 | 107 | | K | K* | K | R | s | R | R | |
| 104 | 108 | | L | L | V | | c | L | L | |
| 105 | 109 | | E | E | E | | s | E | E | |
| 106 | 110 | | I | I | I | | s | I | I | |
| 106A | | | - | - | - | | | - | - | |
| 107 | 111 | FR4 | K | K* | K | - | s | K | K | |

Figure 19C

| Kabat | # | FR or CDR | Mouse 1D9 $V_H$ | Mouse IIIc | Human III | Human Acceptor 4B4'CL (000490) | Surface Or Core | 1D9 $RH_A$ | 1D9 $RH_B$ | Comment |
|---|---|---|---|---|---|---|---|---|---|---|
| 1 | 1 | FR1 | E | E* | E |  | s | E | E |  |
| 2 | 2 |  | V | V | V |  | c | V | V |  |
| 3 | 3 |  | Q | K* | Q |  | s | Q | Q |  |
| 4 | 4 |  | L | L* | L* |  | C | L | L |  |
| 5 | 5 |  | V | E | V |  | s | V | V |  |
| 6 | 6 |  | E | E | E |  | c | E | E |  |
| 7 | 7 |  | S | S | S* |  | c | S | S |  |
| 8 | 8 |  | G | G | G* |  | c | G | G |  |
| 9 | 9 |  | G | G | G* |  | c | G | G |  |
| 10 | 10 |  | G | G* | G |  | c | G | G |  |
| 11 | 11 |  | L | L | L |  | S | L | L |  |
| 12 | 12 |  | V | V* | V |  | c | V | V |  |
| 13 | 13 |  | Q | Q | Q | K | s | K | K |  |
| 14 | 14 |  | P | P | P* |  | c | P | P |  |
| 15 | 15 |  | K | G | G* | G | s | G | G |  |
| 16 | 16 |  | G | G | G |  | s | G | G |  |
| 17 | 17 |  | S | S | S* |  | c | S | S |  |
| 18 | 18 |  | L | M* | L* |  | c | L | L |  |
| 19 | 19 |  | K | K* | R | R | c | R | R |  |
| 20 | 20 |  | L | L | L |  | c | L | L |  |
| 21 | 21 |  | S | S | S* |  | c | S | S |  |
| 22 | 22 |  | C | C | C* |  | C | C | C |  |
| 23 | 23 |  | A | V | A |  | c | A | A |  |
| 24 | 24 |  | A | A | A |  | C | A | A |  |
| 25 | 25 |  | S | S | S* |  | c | S | S |  |
| 26 | 26 |  | G | G | G |  | c | G | G |  |
| 27 | 27 |  | F | F | F* |  | C | F | F |  |
| 28 | 28 |  | S | T* | T | T | C | T | S | Δ1 |
| 29 | 29 |  | F | F* | F |  | C | F | F |  |
| 30 | 30 | FR1 | N | S | S | S | S | S | N | Δ2 |
| 31 | 31 | CDR1 | A | N | S | N | c | A | A |  |
| 32 | 32 |  | Y | Y | Y | A | S | Y | Y |  |
| 33 | 33 |  | A | T | A | W | S | A | A |  |
| 34 | 34 |  | M | M | M |  | c | M | M |  |
| 35 | 35 |  | N | N | S | S | c | N | N |  |
| 35a |  |  | - | - | - |  | c | - | - |  |
| 35b |  | CDR1 | - | - | - |  | c | - | - |  |

Figure 20A

| Kabat | # | FR or CDR | Mouse 1D9 $V_H$ | Mouse IIIc | Human III | Human Acceptor 4B4'CL (000490) | Surface Or Core | 1D9 $RH_A$ | 1D9 $RH_B$ | Comment |
|---|---|---|---|---|---|---|---|---|---|---|
| 36 | 36 | FR2 | W | W | W* | | C | W | W | |
| 37 | 37 | | V | V | V* | | C | V | V | |
| 38 | 38 | | R | R | R* | | C | R | R | |
| 39 | 39 | | Q | Q | Q* | | c | Q | Q | |
| 40 | 40 | | A | S | A | | c | A | A | |
| 41 | 41 | | P | P | P | | s | P | P | |
| 42 | 42 | | G | E | G* | | s | G | G | |
| 43 | 43 | | K | K | K | | s | K | K | |
| 44 | 44 | | G | G | G | | c | G | G | |
| 45 | 45 | | L | L | L* | | C | L | L | |
| 46 | 46 | | E | E* | E | | C | E | E | |
| 47 | 47 | | W | W | W* | | C | W | W | |
| 48 | 48 | | V | V* | V* | | C | V | V | |
| 49 | 49 | FR2 | A | A | S | G | C | G | G | |
| 50 | 50 | CDR2 | R | E | V | | c | R | R | |
| 51 | 51 | | I | I | I | | c | I | I | |
| 52 | 52 | | R | R | S | K | s | R | R | |
| 52a | 53 | | T | L | G | S | s | T | T | |
| 52b | 54 | | K | K | K* | | s | K | K | |
| 52c | 55 | | N | S | T | T | c | N | N | |
| 53 | 56 | | N | H | D | D | | N | N | |
| 54 | 57 | | N | N | G | G | | N | N | |
| 55 | 58 | | Y | Y | G | G | | Y | Y | |
| 56 | 59 | | A | A | S | T | s | A | A | |
| 57 | 60 | | T | T | T | | c | T | T | |
| 58 | 61 | | Y | H | Y | D | c | Y | Y | |
| 59 | 62 | | Y | Y | Y | | c | Y | Y | |
| 60 | 63 | | A | A | A | | c | A | A | |
| 61 | 64 | | D | E | D | A | s | D | D | |
| 62 | 65 | | S | S | S | P | s | S | S | |
| 63 | 66 | | V | V | V* | | c | V | V | |
| 64 | 67 | | K | K | K | | s | K | K | |
| 65 | 68 | CDR2 | D | G | G* | G | s | D | D | |
| 66 | 69 | FR3 | R | R | R* | | C | R | R | |
| 67 | 70 | | Y | F | F* | F | C | F | F | |
| 68 | 71 | | T | T | T | | C | T | T | |
| 69 | 72 | | I | I* | I* | | C | I | I | |
| 70 | 73 | | S | S | S* | | S | S | S | |
| 71 | 74 | | R | R | R* | | C | R | R | |
| 72 | 75 | | D | D | D | | c | D | D | |
| 73 | 76 | | D | D | N | | C | D | D | |
| 74 | 77 | | S | S | S | | s | S | S | |
| 75 | 78 | | E | K | K | K | s | K | K | |
| 76 | 79 | | S | S | N | N | s | N | N | |
| 77 | 80 | | M | S | T | T | c | T | T | |
| 78 | 81 | | L | V | L | | C | L | L | |
| 79 | 82 | | F | Y | Y | Y | c | Y | Y | |
| 80 | 83 | | L | L | L* | | c | L | L | |

Figure 20B

| Kabat | # | FR or CDR | Mouse 1D9 $V_H$ | Mouse IIIc | Human III | Human Acceptor 4B4'CL (000490) | Surface Or Core | 1D9 $RH_A$ | 1D9 $RH_B$ | Comment |
|---|---|---|---|---|---|---|---|---|---|---|
| 81 | 84 | I | Q | Q* | Q | | c | Q | Q | |
| 82 | 85 | I | M | M | M* | | C | M | M | |
| 82a | 86 | I | N | N | N | | s | N | N | |
| 82b | 87 | I | N | N | S | S | s | S | S | |
| 82c | 88 | I | L | L | L* | | c | L | L | |
| 83 | 89 | I | K | R | R | | s | K | K | |
| 84 | 90 | I | T | A | A | | c | T | T | |
| 85 | 91 | I | E | E | E | | s | E | E | |
| 86 | 92 | I | D | D | D | | C | D | D | |
| 87 | 93 | I | T | T | T | | c | T | T | |
| 88 | 94 | I | A | G | A* | | c | A | A | |
| 89 | 95 | I | M | I | V | V | c | V | V | |
| 90 | 96 | I | Y | Y | Y* | | c | Y | Y | |
| 91 | 97 | I | Y | Y | Y* | | C | Y | Y | |
| 92 | 98 | I | C | C* | C* | | C | C | C | |
| 93 | 99 | I | V | T | A | T | C | T | T | |
| 94 | 100 | FR3 | T | T | R | | C | T | T | |
| 95 | 101 | CDR3 | F | G | G | D | c | F | F | |
| 96 | 102 | I | Y | F | R | S | c | Y | Y | |
| 97 | 103 | I | G | - | x | L | s | G | G | |
| 98 | 104 | I | N | - | G | P | c | N | N | |
| 99 | | I | - | - | x | P | c | - | - | |
| 100 | | I | - | - | S | H | c | - | - | |
| 100 a | | I | - | - | L | | C | - | - | |
| 100 b | | I | - | - | S | | C | - | - | |
| 100 c | | I | - | - | G | | | - | - | |
| 100 d | | I | - | - | x | | | - | - | |
| 100 e | | I | - | - | Y | | | - | - | |
| 100 f | | I | - | - | Y | | | - | - | |
| 100 g | | I | - | - | Y | | | - | - | |
| 100 h | | I | - | - | Y | | | - | - | |
| 100 I | | I | - | - | H | | | - | - | |
| 100 j | | I | - | - | Y | | | - | - | |
| 100 k | | I | - | F | F | | C | - | - | |
| 101 | 105 | I | G | A | D | R | C | G | G | |
| 102 | 106 | CDR3 | V | Y | Y | | C | V | V | |
| 103 | 107 | FR4 | W | W | W* | | C | W | W | |
| 104 | 108 | I | G | G | G* | | C | G | G | |
| 105 | 109 | I | T | Q | Q | Q | S | Q | Q | |
| 106 | 110 | I | G | G | G* | | C | G | G | |
| 107 | 111 | I | T | T | T* | | C | T | T | |
| 108 | 112 | I | T | L | L | L | C | L | L | |
| 109 | 113 | I | V | V | V* | | C | V | V | |
| 110 | 114 | I | T | T | T* | | C | T | T | |
| 111 | 115 | I | V | V* | V* | | | V | V | |
| 112 | 116 | I | S | S | S* | | | S | S | |
| 113 | 117 | FR4 | S | S | S* | | | S | S | |

GAGGTGCAATTGGTTGAGTCTGGAGGAGGATTGGTGAAGCCTGGGGGGTCATTGAGACTCTCATGTGCAGCCTCTGGATTCACTTTCAGTGCCTACGCCA
         10
CTCCACGTTAACCAACTCAGAACCTCCTCCTAACCACTTCGAGACCCCCAGTAACTCTGAGAGTACACGTCGGAGACCTAAGTGAAAGTCACGGATGCGGT
Mfe I

E  V  Q  L  V  E  S  G  G  G  L  V  K  P  G  G  S  L  R  L  S  C  A  A  S  G  F  T  F  S  A  Y  A

TGAACTGGGTCCGCCAGGCTCCAGGAAAGGGTTTGGAATGGTTGGCCGCATAAGAACTAAAAAATAATAATTATGCAACATATTATGCCGATTCAGTGAA
                              20
ACTTGACCCAGGCGGTCCGAGGTCCTTCCCAAACCTTACCCAACCGGCGTATTCTTGATTTTTATTATTAATACGTTGTATAATACGGCTAAGTCACTT

M  N  W  V  R  Q  A  P  G  K  G  L  E  W  V  G  R  I  R  T  K  N  N  N  Y  A  T  Y  Y  A  D  S  V  K

AGACAGATTCACCATCTCCAGAGATGATTCAAAAAACACGTCTCTATCTGCAAATGAACAGCTTGAAAACTGAGGACACAGCCGTGTATTACTGTACCACC
                                                        30
TCTGTCTAAGTGGTAGAGGTCTCTACTAAGTTTTTTGTGCAGAGATAGACGTTTACTTGTGAACTTTGACTCCTGTGTCGGCACATAATGACATGGTGG

D  R  F  T  I  S  R  D  D  S  K  N  T  L  Y  L  Q  M  N  S  L  K  T  E  D  T  A  V  Y  Y  C  T  T

TTTTACGGTAACCGGTCGTCTGGGCCAGGGGACCCTGGTCACCGTCAGCTCAGCCAAA
                                              357
AAAATGCCATTGGCCAGCAGACCCGGTCCCCTGGGACCAGTGGCCAGTCGAGTCGGTTT
                                         Blp I

```
                                                                                    10
CTACGTAGTGATGACCCAGTCTCCACTCTCCTTGCCCTGTTACCCTTGGACAGCCAGCCTCCATCTCTTGCAAGTCAGAGCCTCTTAGATAGTGAT
GATGCATCACTACTGGGTCAGAGGTGAGAGGAACGGGACAATGGGAACCTGTCGGTCGGAGGTAGAGAACGTTCAGTCTCGGAGAATCTATCACTA
 [Y] V  V  M  T  Q  S  P  L  S  L  P  V  T  L  G  Q  P  A  S  I  S  C  K  S  S  Q  S  L  L  D  S  D
                                                                                    20
GGAAAGACATTTTGAATTGGTTTCAGCAGAGGCCAGGCCAGTCTCCAAGGCGCCTAATCTATCTGGTGTCTAAACTGGACTCTTGGAGTCCCTGACAGGT
CCTTTCTGTAAAACTTAACCAAAGTCGTCTCCGGTCCAGAGGTTCCGCGGATTAGATAGACCACAGATTTGACCTGAGACCTCAGGGACTGTCCA
 G  K  T  F  L  N  W  F  Q  Q  R  P  G  Q  S  P  R  R  L  I  Y  L  V  S  K  L  D  S  G  V  P  D  R
                                                                                    30
TCAGCGGCAGTGGATCAGGGACAGATTTCACACTGAAAATCAGCAGAGTGGAGGCTGAGGATGTTGGAGTTTATTATTGCTGCAAGGTACACATTTTCC
AGTCGCCGTCACCTAGTCCCTGTCTAAAGTGTGACTTTTAGTCGTCTCACTCCGACTCCTACAACCTCAAATAATAACGACCGTTCCATGTGTAAAAGG
 F  S  G  S  G  S  G  T  D  F  T  L  K  I  S  R  V  E  A  E  D  V  G  V  Y  Y  C  W  Q  G  T  H  F  P
                                                       BstWI
                                                                    344
GTACACGTTCGGACAAGGGACCCTGACTGGAAATAAAACGTACGG
CATGTGCAAGCCTGTTCCCTGGGCTGACCTTTATTTTGCATGCC
 Y  T  F  G  Q  G  T  R  L  E  I  K  R  T
```

Figure 24

RECOMBINANT ANTI-CCR2 ANTIBODIES AND METHODS OF USE THEREFOR

RELATED APPLICATIONS

This application is a continuation-in-part of U.S. application Ser. No. 09/359,193, filed Jul. 22, 1999, now U.S. Pat. No. 6,352,832, which is a continuation-in-part of U.S. application Ser. No. 09/121,781, filed Jul. 23, 1998, now U.S. Pat. No. 6,312,689, the entire teachings of both of which are incorporated herein by reference.

BACKGROUND OF THE INVENTION

Over the past several years a growing family of leukocyte chemoattractant/activating factors, termed chemokines, has been described (Oppenheim, J. J. et al., *Annu. Rev. Immunol.*, 9:617–648 (1991); Schall and Bacon, *Curr. Opin. Immunol.*, 6:865–873 (1994); Baggiolini, M., et al., *Adv. Imunol.*, 55:97–179 (1994)). Members of this family are produced and secreted by many cell types in response to early inflammatory mediators such as IL-1β or TNFα. The chemokine superfamily comprises two main branches: the α-chemokines (or CXC chemokines) and the β-chemokines (CC chemokines). The (α-chemokine branch includes proteins such as IL-8, neutrophil activating peptide-2 (NAP-2), melanoma growth stimulatory activity (MGSA/gro or GROα), and ENA-78, each of which have attracting and activating effects predominantly on neutrophils. The members of the β-chemokine branch affect other cell types such as monocytes, lymphocytes, basophils, and eosinophils (Oppenheim, J. J. et al., *Annu. Rev. Immunol.*, 9:617–648 (1991); Baggiolini, M., et al., *Adv. Imunol.*, 55:97–179 (1994); Miller and Krangel, *Crit. Rev. Immunol.*, 12:17–46 (1992); Jose, P. J., et al., *J. Exp. Med.*, 179:881–118 (1994); Ponath, P. D., et al., *J. Clin. Invest.*, 97:604–612 (1996)), and include proteins such as monocyte chemotactic proteins 1–4 (MCP-1, MCP-2, MCP-3, and MCP-4), RANTES, and macrophage inflammatory proteins (MIP-1α, MIP-1β). Recently a new class of membrane-bound chemokines designated CX3C chemokines has been identified (Bazan, J. F., et al., *Nature* 385:640–644 (1997)). Chemokines can mediate a range of pro-inflammatory effects on leukocytes, such as triggering of chemotaxis, degranulation, synthesis of lipid mediators, and integrin activation (Oppenheim, J. J. et al., *Annu. Rev. Immunol.*, 9:617–648 (1991); Baggiolini, M., et al., *Adv. Imunol.*, 55:97–179 (1994); Miller, M. D. and Krangel, M. S., *Crit. Rev. Immunol.*, 12:17–46 (1992)). Lately, certain β-chemokines have been shown to suppress HIV-1 infection of human T cell lines in vitro (Cocchi, F., et al., *Science* (Wash. DC), 270:1811–1815 (1995)).

Chemokines bind to 7 transmembrane spanning (7TMS) G protein-coupled receptors (Murphy, P. M., *Annu. Rev. Immunol.*, 12:593–633 (1994)). Some known receptors for the CC or β chemokines include CCR1, which binds MIP-1α and RANTES (Neote, K., et al., *Cell*, 72:415–425 (1993); Gao, J. L., *J. Exp. Med.*, 177:1421–1427 (1993)); CCR2, which binds chemokines including MCP-1, MCP-2, MCP-3 and MCP-4 (Charo, I. F., et al., *Proc. Natl. Acad. Sci. USA*, 91:2752–2756 (1994); Myers, S. J., et al., *J. Biol. Chem.*, 270:5786–5792 (1995); Gong et al., *J. Biol Chem* 272:11682–11685 (1997); Garcia-Zepeda et al., *J. Immunol.* 157:5613–5626 (1996)); CCR3, which binds chemokines including eotaxin, RANTES and MCP-3 (Ponath, P. D., et al., *J. Exp. Med.*, 183:2437–2448 (1996)); CCR4, which has been found to signal in response to MCP-1, MIP-1α, and RANTES (Power, C. A., et al., *J. Biol. Chem.*, 270:19495–19500 (1995)); and CCR5, which has been shown to signal in response to MIP-1α, MIP-1β and RANTES (Boring, L., et al., *J. Biol. Chem.*, 271 (13):7551–7558 (1996); Raport, C. J., *J. Biol. Chem.*, 271:17161–17166 (1996); and Samson, M. et al., *Biochemistry*, 35:3362–3367 (1996)).

CCR2 is expressed on the surface of several leukocyte subsets, and appears to be expressed in two slightly different forms (CCR2a and CCR2b) due to alternative splicing of the MRNA encoding the carboxy-terminal region (Charo et al., *Proc. Natl. Acad. Sci. USA* 91:2752–2756 (1994)). MCP-1 acts upon monocytes, lymphocytes and basophils, inducing chemotaxis, granule release, respiratory burst and histamine and cytokine release. Studies have suggested that MCP-1 is implicated in the pathology of diseases such as rheumatoid arthritis, atherosclerosis, granulomatous diseases and multiple sclerosis (Koch, J. Clin. Invest. 90:772–79 (1992); Hosaka et al., Clin. Exp. Immunol. 97:451–457 (1994); Schwartz et al., Am. J. Cardiol. 71(6):9B-14B (1993); Schimmer et al., J. Immunol. 160:1466–1471 (1998); Flory et al., Lab. Invest. 69:396–404 (1993); Gong et al., J. Exp. Med. 186:131–137 (1997)). Additionally, CCR2 can act as a co-receptor for HIV (Connor et al., J. Exp. Med. 185:621–628 (1997)). Thus, CCR2 receptor antagonists may represent a new class of important therapeutic agents.

SUMMARY OF THE INVENTION

The present invention relates to an antibody (imunoglobulin) or functional fragment thereof (e.g., an antigen-binding fragment) which binds to a mammalian CC-chemokine receptor 2 (also referred to as CCR2, CKR-2, MCP-1RA or MCP-1RB) or portion of the receptor (anti-CCR2). In one embodiment, the antibody of the present invention or fragment thereof has specificity for human or rhesus CCR2 or a portion thereof. In another embodiment, the antibody or fragment of the invention blocks binding of a ligand (e.g., MCP-1, MCP-2, MCP-3, MCP-4) to the receptor and inhibits function associated with binding of the ligand to the receptor (e.g., leukocyte trafficking). For example, as described herein, antibodies and fragments thereof of the present invention which bind human or rhesus CCR2 or a portion thereof, can block binding of a chemokine (e.g., MCP-1, MCP-2, MCP-3, MCP-4) to the receptor and inhibit function associated with binding of the chemokine to the receptor. In one embodiment, the antibody is monoclonal antibody (mAb) LS132.1D9 (1D9) or an antibody which can compete with 1D9 for binding to human CCR2 or a portion of human CCR2. Functional fragments of the foregoing antibodies are also envisioned.

In another embodiment, the antibody or functional fragment of the present invention binds human CCR2 or a portion thereof, and inhibits human immunodeficiency virus (HIV) binding to the receptor, thereby inhibiting function associated with binding of HIV to the receptor (e.g., HIV antigen release and infectivity). In one embodiment, the antibody is monoclonal antibody 1D9 or an antibody which can compete with 1D9 for binding to human CCR2 or a portion of human CCR2.

The present invention also relates to an antibody or functional fragment thereof (e.g., an antigen-binding fragment) which binds to a mammalian CCR2 or portion of the receptor and provides increased fluorescent staining intensity of CCR2 or compositions comprising CCR2 relative to other anti-CCR2 antibodies. In one embodiment, the antibody is monoclonal antibody 1D9 or LS132.8G2 (8G2) or an antibody which can compete with 1D9 or 8G2 for binding to human CCR2 or a portion of human CCR2.

The present invention also relates to a humanized immunoglobulin or antigen-biding fragment thereof having binding specificity for CCR2, said immunoglobulin comprising an antigen binding region of nonhuman origin (e.g., rodent) and at least a portion of an immunoglobulin of human origin (e.g., a human framework region, a human constant region of the gamma type). In one embodiment, the humanized immunoglobulin or fragment thereof described herein can compete with 1D9 for binding to CCR2. In a preferred embodiment, the antigen binding region of the humanized immunoglobulin is derived from monoclonal antibody 1D9 (e.g., an immunoglobulin comprising the variable regions of the light and heavy chains as shown in FIG. 7 (SEQ ID NO: 9) and FIG. 8 (SEQ ID NO: 10), respectively).

For example, the humanized immunoglobulin or antigen-binding fragment thereof can comprise an antigen binding region comprising at least one complementarity determining region (CDR) of nonhuman origin, and a framework region (FR) derived from a human framework region. In one aspect, the humanized immunoglobulin having binding specificity for CCR2 comprises a light chain comprising at least one CDR derived from an antibody of nonhuman origin which binds CCR2 and a FR derived from a light chain of human origin (e.g., from HF-21/28), and a heavy chain comprising a CDR derived from an antibody of nonhuman origin which binds CCR2 and a FR derived from a heavy chain of human origin (e.g., from 4B4'CL). In another aspect, the light chain comprises three CDRs derived from the light chain of the 1D9 antibody, and the heavy chain comprises three CDRs derived from the heavy chain of the 1D9 antibody.

The present invention also relates to humanized immunoglobulin light chains and antigen-binding fragments thereof (e.g., comprising CDR1, CDR2 and CDR3 of the light chain of the 1D9 antibody, and a human light chain FR), and to humanized immunoglobulin heavy chains and antigen-binding fragments thereof (e.g., comprising CDR1, CDR2 and CDR3 of the heavy chain of the 1D9 antibody, and a human heavy chain FR). In a preferred embodiment, the invention relates to humanized heavy and light chains described herein (e.g., a humanized light chain comprising the variable region of the light chain shown in FIG. 7 (SEQ ID NO: 9), a humanized heavy chain comprising the variable region of the heavy chain shown in FIG. 8 (SEQ ID NO: 10). Also encompassed are humanized immunoglobulins comprising one or more humanized light and/or heavy chains.

The invention further relates to isolated nucleic acid molecules comprising a nucleic acid sequence which encodes a humanized immunoglobulin of the present invention (e.g., a single chain antibody), as well as to isolated nucleic acid molecules comprising a sequence which encodes a humanized immunoglobulin light chain (e.g., comprising nucleotides 52–390 of SEQ ID NO: 95) or heavy chain (e.g., comprising nucleotides 58–411 of SEQ ID NO: 96) of the present invention. For example, the present invention provides a gene (e.g., a fused gene) encoding a humanized immunoglobulin light or heavy chain comprising a first nucleic acid sequence encoding an antigen binding region derived from murine 1D9 monoclonal antibody; and a second nucleic acid sequence encoding at least a portion of a constant region of an immunoglobulin of human origin.

The present invention further relates to a construct comprising a nucleic acid molecule encoding a humanized immunoglobulin having binding specificity for CCR2 or a chain of such an immunoglobulin. For example, an expression vector comprising a gene (e.g., a fused gene) encoding a humanized immunoglobulin light chain, comprising a nucleotide sequence encoding a CDR derived from a light chain of a nonhuman antibody having binding specificity for CCR2, and a framework region derived from a light chain of human origin, is provided. An expression vector comprising a gene encoding a humanized immunoglobulin heavy chain, comprising a nucleotide sequence encoding a CDR derived from a heavy chain of a nonhuman antibody having binding specificity for CCR2, and a framework region derived from a heavy chain of human origin is another example of such a construct.

The present invention also relates to a host cell comprising a nucleic acid molecule of the present invention, including one or more constructs comprising a nucleic acid molecule of the present invention. In one embodiment, the invention relates to a host cell comprising a first recombinant nucleic acid encoding a humanized immunoglobulin light chain, and a second recombinant nucleic acid encoding a humanized immunoglobulin heavy chain, said first nucleic acid comprising a nucleotide sequence encoding a CDR derived from the light chain of murine 1D9 antibody and a framework region derived from a light chain of human origin; and said second nucleic acid comprising a nucleotide sequence encoding a CDR derived from the heavy chain of murine 1D9 antibody and a framework region derived from a heavy chain of human origin.

The present invention also provides a method of preparing a humanized immunoglobulin comprising maintaining a host cell of the present invention under conditions appropriate for expression of a humanized immunoglobulin, whereby a humanized immunoglobulin chain(s) is expressed and a humanized immunoglobulin is produced. The method can further comprise the step of isolating the humanized immunoglobulin.

The humanized immunoglobulins of the present invention can be less immunogenic than their murine or other nonhuman counterparts. Thus, the humanized immunoglobulins described herein can be used as therapeutic agents in humans, for example to control lymphocyte homing to mucosal lymphoid tissue, thereby, reducing inflammatory responses.

The invention further relates to a humanized immunoglobulin of the present invention for use in diagnosis or therapy (including prophylaxis). In one embodiment, the invention relates to a humanized immunoglobulin of the present invention for use in the treatment of diseases associated with leukocyte infiltration of tissues, for example, in the treatment of inflammatory diseases, autoimmune diseases, graft rejection, HIV infection and monocyte-mediated disorders such as atherosclerosis.

In another aspect, the invention relates to use of a humanized immunoglobulin of the present invention for the manufacture of a medicament for the treatment of diseases associated with leukocyte infiltration of tissues, for example, in the treatment of inflammatory diseases, autoimmune diseases, monocyte-mediated disorders such as atherosclerosis, graft rejection, or HIV infection.

The present invention further relates to a method of inhibiting the interaction of a cell bearing mammalian (e.g., human, non-human primate or murine) CCR2 with a ligand thereof, comprising contacting the cell with an effective amount of an antibody or functional fragment thereof which binds to a mammalian CCR2 or a portion of CCR2. Suitable cells include granulocytes, leukocytes, such as monocytes, macrophages, basophils and eosinophils, mast cells, and lymphocytes including T cells (e.g., CD8+ cells, CD4+ cells, CD25+ cells, CD45RO+ cells), and other cells expressing CCR2 such as a recombinant cell expressing CCR2 (e.g., transfected cells). In a particular embodiment, the antibody is 1D9 or an antibody which can compete with 1D9 for binding to human CCR2 or a portion of human CCR2.

Another embodiment of the invention relates to a method of inhibiting the interaction of a cell bearing mammalian CCR2 with a chemokine, comprising contacting said cell with an effective amount of an antibody or functional fragment thereof which binds to CCR2 or a portion of said receptor. In one embodiment of the method, the antibody or functional fragment thereof is any one or more of 1D9, an antigen-binding fragment of 1D9 or an antibody or fragment thereof having an epitopic specificity which is the same as or similar to that of 1D9. Furthermore, the invention relates to a method of inhibiting a function associated with binding of a chemokine to CCR2, comprising administering an effective amount of an antibody or functional fragment thereof which binds to a mammalian CCR2 protein or a portion of said receptor. In one aspect of the method, the antibody or functional fragment thereof is any one or more of 1D9, an antigen-binding fragment of 1D9 or an antibody or fragment thereof having an epitopic specificity which is the same as or similar to that of 1D9.

Another aspect of the invention is a method of identifying expression of a mammalian CCR2 or portion of the receptor by a cell. According to the method, a composition comprising a cell or fraction thereof (e.g., a membrane fraction) is contacted with an antibody or functional fragment thereof (e.g., 1D9 or 8G2) which binds to a mammalian CCR2 protein or portion of the receptor under conditions appropriate for binding of the antibody thereto, and the formation of a complex between said antibody or fragment and said protein or portion thereof is detected. Detection of the complex, directly or indirectly, indicates the presence of the receptor on the cell. The present invention also relates to a kit for use in detecting the presence of CCR2 or a portion thereof in a biological sample, comprising an antibody or functional fragment thereof which binds to a mammalian CC-chemokine receptor 2 or a portion of said receptor, and one or more ancillary reagents suitable for detecting the presence of a complex between said antibody or fragment and said protein or portion thereof.

Also encompassed by the present invention are methods of identifying additional ligands or other substances which bind a mammalian CCR2 protein, including inhibitors and/or promoters of mammalian CCR2 function. For example, agents having the same or a similar binding specificity as that of an antibody of the present invention or functional fragment thereof can be identified by a competition assay with said antibody or fragment. Thus, the present invention also encompasses methods of identifying ligands or other substances which bind the CCR2 receptor, including inhibitors (e.g., antagonists) or promoters (e.g., agonists) of receptor function. In one embodiment, cells which naturally express CCR2 receptor protein or suitable host cells which have been engineered to express a CCR2 receptor or variant encoded by a nucleic acid introduced into said cells are used in an assay to identify and assess the efficacy of ligands, inhibitors or promoters of receptor function. Such cells are also useful in assessing the function of the expressed receptor protein or polypeptide.

Thus, the invention also relates to a method of detecting or identifying an agent which binds a mammalian CCR2 or ligand binding variant thereof, comprising combining an agent to be tested, an antibody or antigen-binding fragment of the present invention (e.g., monoclonal antibody 1D9, an antibody having an epitopic specificity which is the same as or similar to that of 1D9, antigen-binding fragments of 1D9, monoclonal antibody 8G2, an antibody having an epitopic specificity which is the same as or similar to that of 8G2, and antigen-binding fragments of 8G2) and a composition comprising a mammalian CCR2 protein or a ligand binding variant thereof. The foregoing components can be combined under conditions suitable for binding of the antibody or antigen-binding fragment to mammalian CCR2 protein or a ligand binding variant thereof, and binding of the antibody or fragment to the mammalian CCR2 protein or ligand binding variant is detected or measured, either directly or indirectly, according to methods described herein or other suitable methods. A decrease in the amount of complex formed relative to a suitable control (e.g., in the absence of the agent to be tested) is indicative that the agent binds said receptor or variant. The composition comprising a mammalian CCR2 protein or a ligand binding variant thereof can be a membrane fraction of a cell bearing recombinant CCR2 protein or ligand binding variant thereof. The antibody or fragment thereof can be labeled with a label such as a radioisotope, spin label, antigen label, enzyme label, fluorescent group and chemiluminescent group. These and similar assays can be used to detect agents, including ligands (e.g., chemokines which interact with CCR2) or other substances, including inhibitors or promoters of receptor function, which can bind CCR2 and compete with the antibodies described herein for binding to the receptor.

According to the present invention, ligands, inhibitors or promoters of receptor function can be identified in a suitable assay, and further assessed for therapeutic effect. Inhibitors of receptor function can be used to inhibit (reduce or prevent) receptor activity, and ligands and/or promoters can be used to induce (trigger or enhance) normal receptor function where indicated. The present invention also provides a method of treating inflammatory diseases, autoimmune diseases, atherosclerosis, and graft rejection, or HIV infection, comprising administering an inhibitor of receptor function (e.g., chemokine binding or HIV binding) to an individual (e.g., a mammal, such as a human). The present invention further provides a method of stimulating receptor function by administering a novel ligand or promoter to an individual, providing a new approach to selective stimulation of leukocyte function, which is useful, for example, in the treatment of infectious diseases and cancer.

Another aspect of the invention relates to a method of inhibiting HIV infection of a cell which expresses a mammalian CCR2 or portion thereof, comprising contacting the cell with an effective amount of an antibody or functional fragment thereof which binds to a mammalian CCR2 or portion of the receptor and inhibits HIV binding and infection. In a particular embodiment of the invention, the antibody or functional fragment thereof is any of 1D9, an antibody having an epitopic specificity which is the same as or similar to that of 1D9, an antibody which can compete with 1D9 for binding to human CCR2, and antigen-binding fragments thereof.

Also encompassed by the present invention is a method of inhibiting (e.g., treating) HIV in a patient, comprising administering to the patient an effective amount of an antibody or functional fragment thereof which binds to a mammalian CCR2 or a portion of said receptor and inhibits HIV binding to the CCR2 receptor. The anti-CCR2 antibody or fragment can be administered alone or in combination with one or more additional therapeutic agents, e.g., one or more antibodies which bind a co-receptor for HIV infection and inhibit binding to said co-receptor, such as an anti-CCR3, anti-CCR5, and/or anti-CXCR4 antibody.

Another aspect of the invention also relates to a method of preventing or inhibiting HIV infection in an individual, comprising administering to the individual an effective amount of an antibody or functional fragment thereof which binds to CCR2 and inhibits HIV binding to CCR2. According to the method, preventing HIV infection includes treatment in order to prevent (reduce or eliminate) infection of new cells in an infected individual or in order to prevent infection in an individual who may be, may have been or has been exposed to HIV. For example, individuals such as an HIV infected individual, a fetus of an HIV infected female, or a health care worker can be treated according to the method of the present invention.

The present invention also encompasses a method of inhibiting leukocyte trafficking in a patient, comprising administering to the patient an effective amount of an antibody or functional fragment thereof which binds to a mammalian CCR2 or portion of said receptor and inhibits function associated with binding of a ligand to the receptor.

The present invention also relates to a method of inhibiting or treating CCR2-mediated disorders, such as inflammatory disorders, comprising administering to a patient an effective amount of an antibody or functional fragment thereof which binds to a mammalian CCR2 or portion of said receptor and inhibits CCR2-mediated function. For example, the invention relates to a method of inhibiting or treating stenosis or restenosis of the vasculature comprising administering to a patient an effective amount of an antibody or functional fragment thereof which binds to a mammalian CCR2 or portion of said receptor and inhibits CCR2-mediated function.

The present invention further relates to an antibody or fragment thereof as described herein (e.g., monoclonal antibody 1D9 or an antigen-binding fragment thereof) for use in therapy (including prophylaxis) or diagnosis, and to the use of such an antibody or fragment for the manufacture of a medicament for the treatment of a CCR2-mediated disorder, or other disease or inflammatory condition as described herein.

BRIEF DESCRIPTION OF THE FIGURES

FIGS. 2A-2L are FACS dot plots showing expression of CCR2 on most monocytes, a subpopulation of lymphocytes and a small subset of granulocytes. Whole blood cells were stained with one of three anti-CCR2 mAbs (5A11, generated using a peptide consisting of the first 32 amino acids of the CCR2 amino-terminus as an immunogen, and 1D9 and 8G2 generated as described herein using CCR2b L½ cell transfectants as the immunogen). Staining was analyzed by flow cytometry, and the lymphocyte, granulocyte and monocyte populations were gated using the forward and side light scatter. The X-axis represents forward light scatter (a measure of cell size), and the Y-axis fluorescence intensity of staining for CCR2. The level of negative control staining is indicated by a line.

FIG. 6A shows the results of chemotaxis assays of PBMC to 10 nM MCP-1 with no antibody, or 0.1 or 10 μg/ml of 1D9 or nonspecific murine IgG2a. The spontaneous nonspecific migration is also indicated. FIG. 6B shows the results of chemotaxis assays of PBMC to 10 nM RANTES with no antibody, 10 μg/ml 1D9 or 10 μg/ml nonspecific murine IgG2a. The spontaneous nonspecific migration in the absence of RANTES is also indicated.

FIG. 7 shows the amino acid sequence (SEQ ID NO: 9) of the kappa light chain variable region of the murine 1D9 antibody. The CDRs are highlighted in bold.

FIG. 8 shows the amino acid sequence (SEQ ID NO: 10) of the heavy chain variable region of the murine 1D9 antibody. The CDRs are highlighed in bold.

FIG. 9 illustrates the canonical classes of CDRs in the murine 1D9 $V_K$ region. "Chothia Canonical Classes" indicates where the canonical classes as defined by Chothia and his colleagues (Chothia and Lesk, J. Mol. Biol. 197:901 (1987); Chothia et al., Nature 34:877 (1989); Tramontano et al., J. Mol. Biol. 215:175 (1990); and Chothia et al., J. Mol. Biol. 227:799 (1992)) were used, while "Martin Canonical Classes" signifies where the canonical classes defined by Martin and Thornton (Martin and Thornton, J. Mol. Biol. 263:800 (1996)) were used. FR residues are highlighted in bold.

FIG. 10 illustrates the canonical classes of CDRs in the murine 1D9 $V_H$ region. "Chothia Canonical Classes" indicates where the canonical classes as defined by Chothia and his colleagues (Chothia and Lesk, J. Mol. Biol. 197:901 (1987); Chothia et al., Nature 34:877 (1989); Tramontano et al., J. Mol. Biol. 215:175 (1990); and Chothia et al., J. Mol. Biol. 227:799 (1992)) were used, while "Martin Canonical Classes" signifies where the canonical classes defined by Martin and Thornton (Martin and Thornton, J. Mol. Biol. 263:800 (1996)) were used. FR residues are highlighted in bold.

FIG. 11 shows the amino acid sequences of various versions of the humanised 1D9 $V_K$ region (SEQ ID NOS: 12–15, respectively). Where the 1D9 $V_K$ region residues (SEQ ID NO: 9) and the human HF-21/28 $V_K$ region (SEQ ID NO: 11) sequences match a dot [.] is shown. Where no amino acid is present at a specific residue position a dash [-] is shown. Where an amino acid in the HF-21/28 FRs is changed in the humanised 1D9 $V_K$ region, it is highlighted in bold. The CDRs are described by the use of nomenclature [==L1==]. The numbering used is according to Kabat et al., *Sequences of proteins of immunological interest*, Fifth edition, U.S. Department of Health and Human Services, U.S. Government Printing Office (1991).

FIG. 12 shows the amino acid sequences of various versions of the humanised 1D9 $V_H$ region (SEQ ID NOS: 17–20, respectively). Where the 1D9 $V_H$ region residues (SEQ ID NO: 10) and the human 4B4'CL $V_H$ region sequences (SEQ ID NO: 16) match a dot [.] is shown. Where no amino acid is present at a specific residue position a dash [-] is shown. Where an amino acid in the 4B4'CL is changed in the humanised 1D9 VH region, it is highlighted in bold. The CDRs are described by the use of nomenclature [==H1==], while [- - - ] denotes part of the H1 structure loop. The numbering used is according to Kabat et al., *Sequences of proteins of immunological interest*, Fifth edition, U.S. Department of Health and Human Services, U.S. Government Printing Office (1991).

FIG. 13 shows a comparison of a portion of the murine 1D9 $V_K$ region (SEQ ID NO: 21) with mouse germline $V_K$ gene sequences (SEQ ID NOS: 22–33, respectively). "Identical residues" represents the number of identical residues in a mouse germline $V_K$ region to the murine 1D9 $V_K$ region. Where the 1D9 $V_K$ region sequence and the mouse germnine $V_K$ region sequences match a dot [.] is shown. Where no amino acid is present at a specific residue position a dash [-] is shown.

FIG. 14 shows a comparison of a portion of the murine 1D9 $V_H$ region (SEQ ID NO: 34) with mouse germline $V_H$ gene sequences (SEQ ID NOS: 35–53, respectively). "Identical residues" represents the number of identical residues in a mouse germline $V_H$ region to the murine 1D9 $V_H$ region. Where the 1D9 $V_H$ region sequence and the mouse germline $V_H$ region sequences match a dot [.] is shown. Where no amino acid is present at a specific residue position a dash [-] is shown.

FIG. 15 shows a comparison of the murine 1D9 $V_K$ region (SEQ ID NO: 9) with the most homologous seventeen human $V_K$ amino acid sequences (SEQ ID NOS: 54–70, respectively). "ID" represents the percentage identity of the human $V_K$ sequences to the murine 1D9 $V_K$ region. Where the 1D9 $V_K$ region residues and the human $V_K$ region sequences match a dot [.] is shown. Where no amino acid is present at a specific residue position a dash [-] is shown. "S" indicates amino acid positions on the surface of the $F_V$ domain. "C" indicates residues located within the core of the $F_V$ domain. Residues within 5 Å of a CDR are defined using capital letters, while those located further away are described with a lower case letter. The CDRs themselves are described by the use of the nomenclature ==L1==. "v" denotes the Vernier residues (Foote and Winter, *J. Mol. Biol.* 224:487 (1992)) located in the FRs. Those residues in the human $V_K$ region sequences which are underlined differ from their closest human $V_K$ germline gene. The numbering used is as according to Kabat et al., *Sequences of proteins of immunological interest*, Fifth edition, U.S. Department of Health and Human Services, U.S. Government Printing Office (1991).

FIG. 16 shows a comparison of the murine 1D9 $V_K$ region with the most homologous seventeen human $V_K$ amino acid sequences. "ID" indicates the percentage identity of the human $V_K$ sequence to the murine 1D9 $V_K$ region. "Surface" indicates the number of identical residues on the surface. "Core" indicates the number of identical residues within the core of the $F_V$ domain. "CDR" indicates the number of identical residues within the CDRs. "FR" indicates the number of identical residues within the FRs. "FR Surface" indicates the number of identical residues which are surface exposed. "FR Core" indicates the number of identical residues which are located within the core of the $F_V$ domain. "FR Near CDR" represents the number of identical residues amongst the FR amino acids within 5 Å of a CDR. "Vernier" indicates the number of identical residues amongst the 14 Vernier amino acids (Foote and Winter, *J. Mol. Biol.* 224:487 (1992)). "$V_K$" indicates the number of identical residues within the $V_K$ gene. "J Chain" indicates the number of identical residues within the J chain gene. "L1 Len" to "L3 Len" defines the number of residues in each CDR, while "L1 Class" to "L3 Class" describes the canonical class of the CDR according to Martin and Thornton (Martin and Thornton, *J. Mol. Biol.* 263:800(1996)).

FIGS. 17A–17B show a comparison of the murine 1D9 $V_H$ region (SEQ ID NO: 10) with the most homologous 24 human $V_H$ amino acid sequences (SEQ ID NOS: 71–94, respectively). "ID" represents the percentage identity of the human $V_H$ sequences to the murine 1D9 $V_H$ region. Where the 1D9 $V_H$ region residues and the human $V_H$ region sequences match a dot [.] is shown. Where no amino acid is present at a specific residue position a dash [-] is shown. "S" indicates amino acid positions on the surface of the $F_V$ domain. "C" indicates residues located within the core of the $F_V$ domain. Residues within 5 Å of a CDR are defined using capital letters, while those located farther away are described with a lower case letter. The CDRs themselves are described by the use of the nomenclature ==H1==. "v" denotes the Vernier residues (Foote and Winter, *J. Mol. Biol.* 224:487 (1992)) located in the FRs. Those residues in the human $V_H$ region sequences which are underlined differ from their closest human $V_H$ germline gene. The numbering used is as according to Kabat et al., *Sequences of proteins of immunological interest*, Fifth edition, U.S. Department of Health and Human Services, U.S. Government Printing Office (1991).

FIGS. 18A–18B show a comparison of the murine 1D9 $V_H$ region with the most homologous 24 human $V_H$ amino acid sequences. "ID" indicates percentage identity of the human $V_H$ sequence to the murine 1D9 $V_H$ region. "All" indicates the number of identical residues in the whole of the human $V_H$ region when compared to the whole of the murine 1D9 $V_H$ region. "Surface" indicates the number of identical residues on the surface. "Core" indicates the number of identical residues within the core of the $F_V$ domain. "CDR" indicates the number of identical residues within the CDRs. "FR" indicates the number of identical residues within the Frs. "FR Surface" indicates the number of identical residues which are surface exposed. "FR Core" indicates the number of identical residues which are located within the core of the $F_V$ domain. "FR Near CDR" represents the number of identical residues amongst the FR amino acids within 5 Å of a CDR. "Vernier" indicates the number of identical residues amongst the 14 Vernier amino acids (Foote and Winter, *J. Mol. Biol.* 224:487 (1992)). "$V_H$" indicates the number of identical residues within the $V_H$ gene. "J Chain" indicates the number of identical residues within the J chain gene. "H1 Size" to "H3 Size" define the number of residues in each CDR, while "H1 Class" and "H2 Class" describe the canonical class of the CDR according to Martin and Thornton, (*J. Mol. Biol.* 263:800 (1996)).

FIGS. 19A–19C show the alignment of amino acid sequences leading to the design of the first (1D9RK$_A$) and second (1D9RK$_B$) humanised versions of the 1D9 antibody kappa light chain variable region. Amino acids identical to the mouse 1D9 at a particular residue position in column 7 are not shown; "-" indicates no amino acid is located at this residue position. Boldface type indicates positions in FRs and CDRs where the human amino acid residue was replaced by the corresponding mouse residue. "Δ" indicates the numbering of changes in the human FRs of 1D9°RK$_A$. "Mouse 1D9 V$_K$" indicates the amino acid sequence of the V$_K$ region from the murine 1D9 kappa light chain variable region. "Mouse κ-II" indicates the consensus sequence of mouse V$_K$ regions from Kabat subgroup κ-II. "Human κ-II" indicates the consensus sequence of human V$_K$ regions from Kabat subgroup κ-II. "HF-21/28" indicates the amino acid sequence of the light chain variable region from the human HF-21/28 antibody (Chastagner et al., *Gene* 101(2):305–6 (1991)). The number in parenthesis (005056) is the Kabat database ID number. "Surface or Core" indicates the position of the amino acid in relation to the rest of the residues in both chains of the antibody variable regions. Residues within 5 Å of a CDR are defined using capital letters. "1D9RK$_A$" indicates the amino acid sequence of the first version of the humanised 1D9 V$_K$ region. "1D9RK$_B$" indicates the amino acid sequence of the second version of the humanised 1D9 V$_K$ region.

FIGS. 20A–20C show the alignment of amino acid sequences leading to the design of the first (1D9RH$_A$) and second (1D9RH$_B$) humanised human versions of the 1D9 antibody kappa heavy chain variable region. Amino acids identical to the mouse 1D9 at a particular residue position in column 7 are not shown. "-" indicates that no amino acid is located at this residue position. Boldface type indicates positions in the FRs and CDRs where the human amino acid residue was replaced by the corresponding mouse residue. "Δ" indicates the numbering of changes in the human FRs of 1D9°RHA. "Mouse 1D9 V$_H$" indicates the amino acid sequence of the V$_H$ region from the murine 1D9 heavy chain variable region. "Mouse IIIc" indicates the consensus sequence of mouse V$_H$ regions from Kabat subgroup IIIc. "Human III" indicates the consensus sequence of human V$_H$ regions from Kabat subgroup III. "4B4'CL" indicates the amino acid sequence of the heavy chain variable region from the human 4B4'CL antibody (Sanz et al., *Journal of Immunology* 142:883 (1989)). The number in parenthesis (000490) is the Kabat database ID number. "Surface or Core" indicates the position of the amino acid in relation to the rest of the residues in both chains of the antibody variable regions. Residues within 5 Å of a CDR are defined using capital letters. "1D9RH$_A$" indicates the amino acid sequence of the first version of the humanised 1D9 V$_H$ region. "1D9RH$_B$" indicates the amino acid sequence of the second version of the humanised. 1D9 V$_H$ region.

FIG. 21 shows the nucleotide sequence, complement and encoded amino acid sequence of the murine antibody 1D9 heavy chain variable region. The leader sequence and a portion of the constant region are also shown. The illustrated nucleotide sequence is SEQ ID NO: 96, the complementary sequence is SEQ ID NO: 99, and the amino acid sequence is SEQ ID NO: 100.

FIG. 22 shows the nucleotide sequence, complement and encoded amino acid sequence of the murine antibody 1D9 kappa light chain variable region. The leader sequence and a portion of the constant region are also shown. The illustrated nucleotide sequence is SEQ ID NO: 95, the complementary sequence is SEQ ID NO: 101, and the amino acid sequence is SEQ ID NO: 102.

FIG. 23 shows the nucleotide sequence of the humanized heavy chain 1D9RH$_A$. The indicated enzyme sites were added for cloning into the vector pLKTOK38. The vector also has human leader and constant regions. The illustrated nucleotide sequence is SEQ ID NO: 97, the complementary sequence is SEQ ID NO: 103, and the amino acid sequence is SEQ ID NO: 104.

FIG. 24 shows the nucleotide sequence of the humanized light chain 1D9RK$_A$. The indicated enzyme sites were added for cloning into the vector pLKTOK38. The vector also has human leader and constant regions. The bracketed Y indicates a residue which changes to aspartate when put into the vector pLKTOK38. The illustrated nucleotide sequence is SEQ ID NO: 98, the complementary sequence is SEQ ID NO: 105, and the amino acid sequence is SEQ ID NO: 106.

DETAILED DESCRIPTION OF THE INVENTION

Figure 1A:
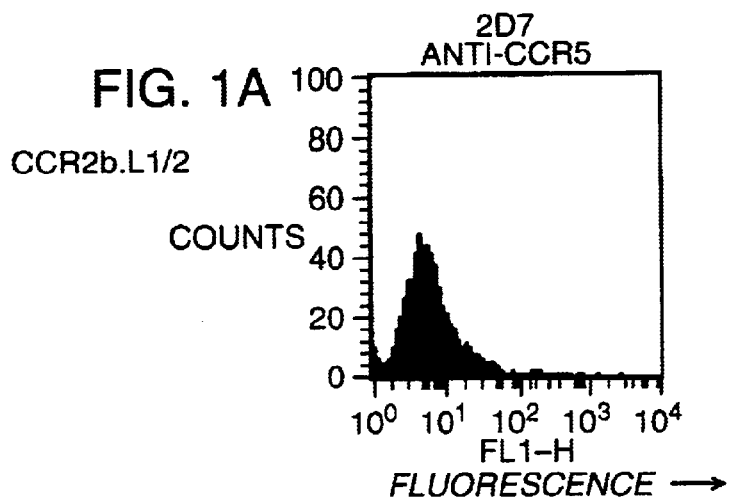
FIGS. 1A-1O are fluorescence activated cell scanning (FACS) histogram profile illustrating that mAbs 1D9 and 8G2 stain CCR2 transfectants but not CCR5 or CCR1 transfectants. L½ (also referred to herein as L1.2) murine pre-B lymphoma host cells were transfected with CCR2, CCR5 and CCR1 as indicated, and stained with antibodies with different receptor specificities. Staining was analyzed by flow cytometry.
Figure 1B:
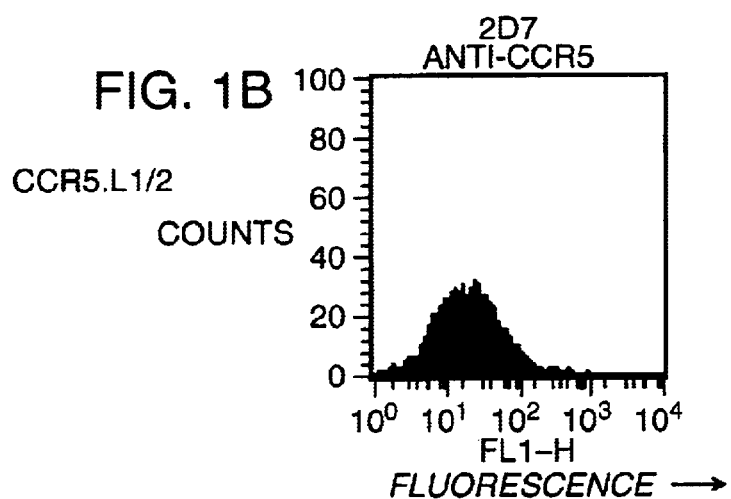
Figure 1C:
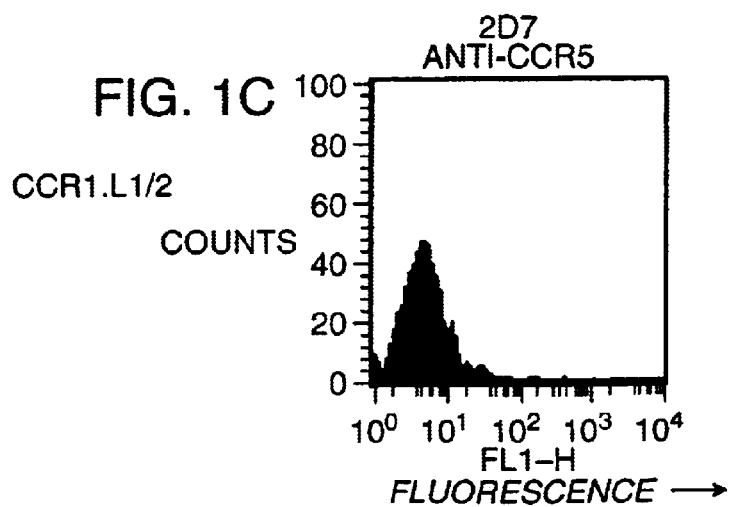
Figure 1D:
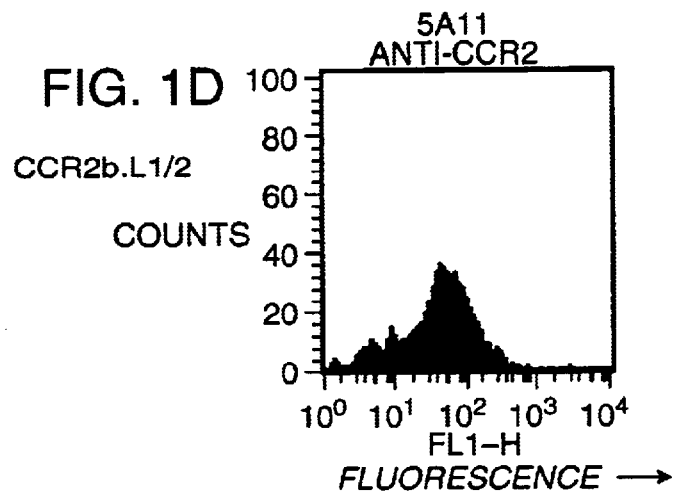
Figure 1E:
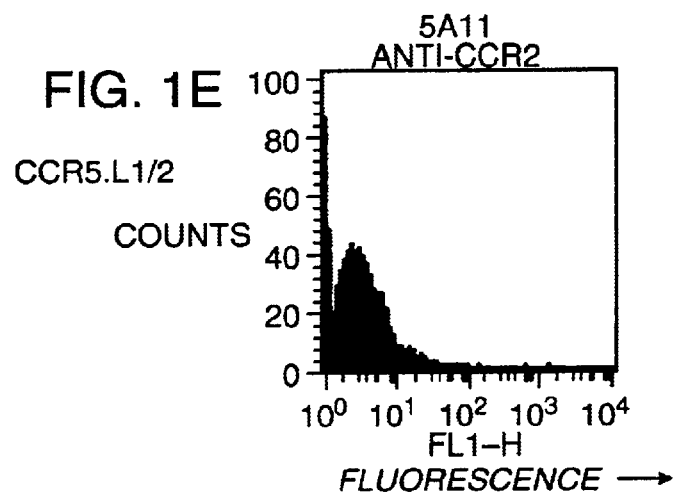
Figure 1F:
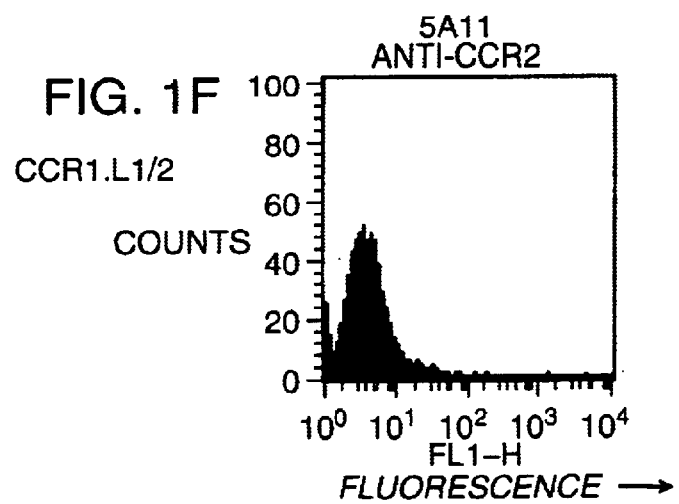
Figure 1G:
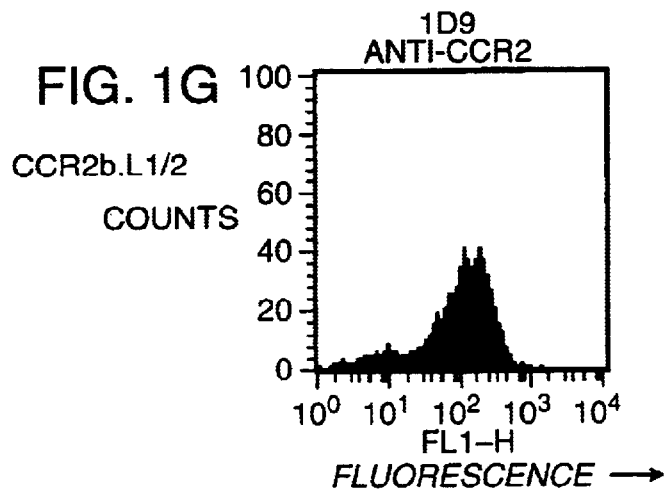
Figure 1H:
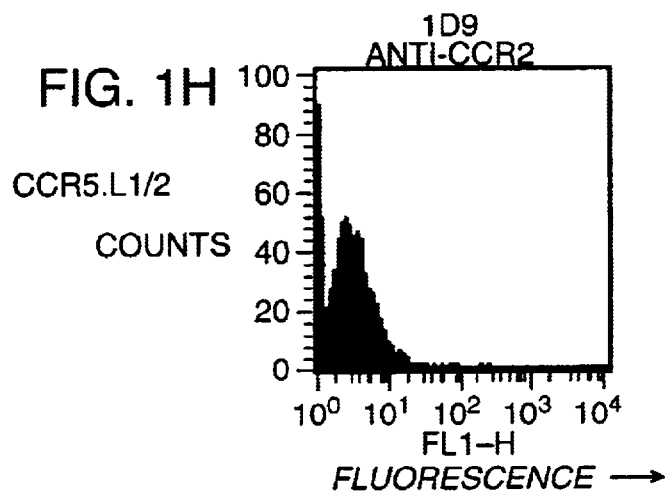
Figure 1I:
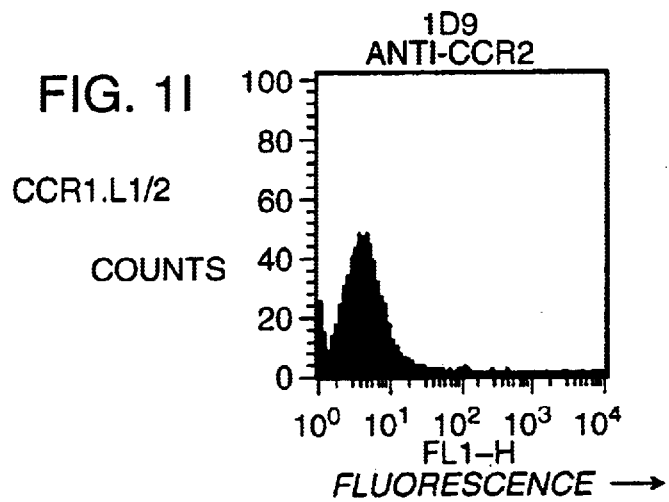
Figure 1J:
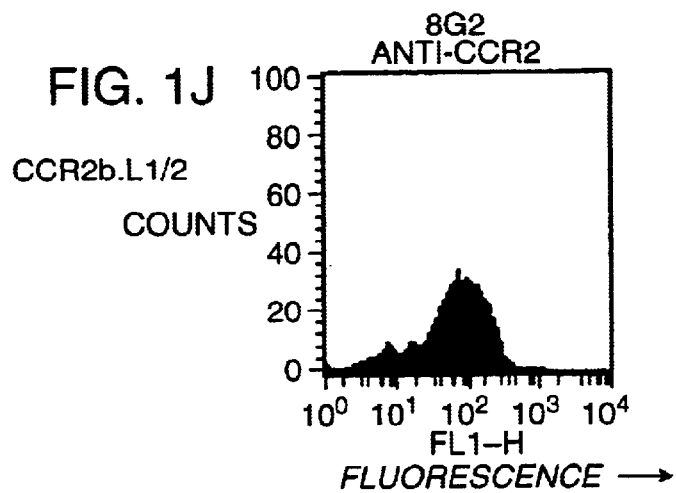
Figure 1K:
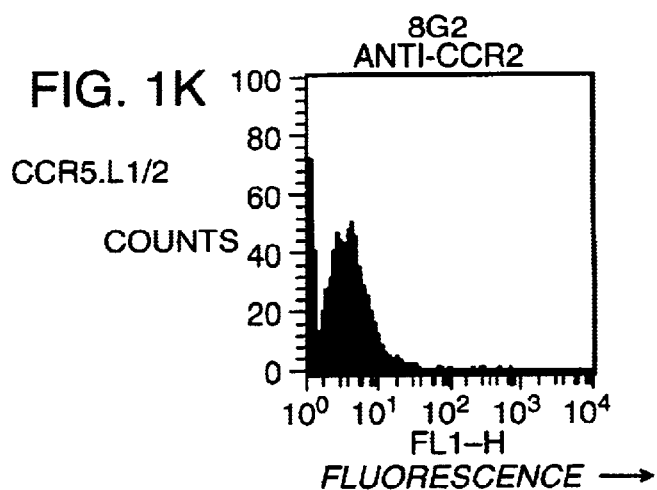
Figure 1L:
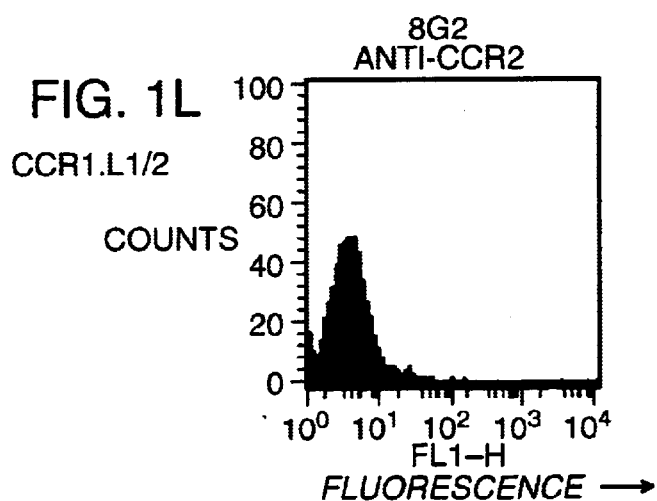
Figure 1M:
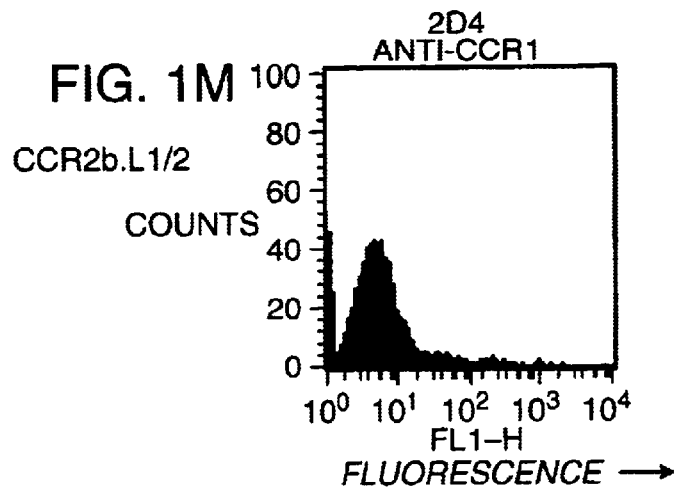
Figure 1N:
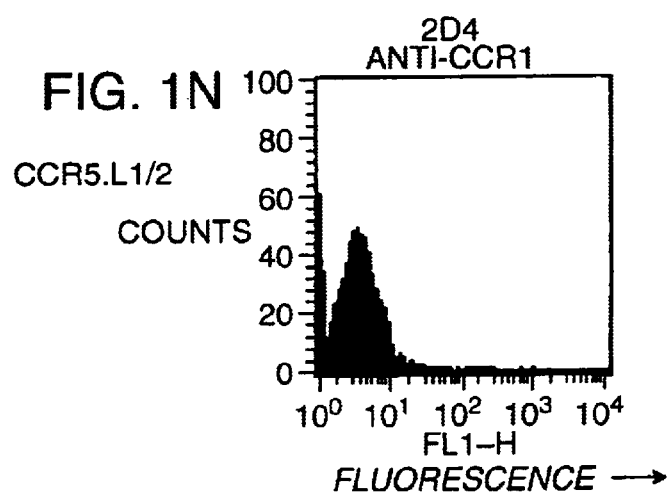
Figure 1O:
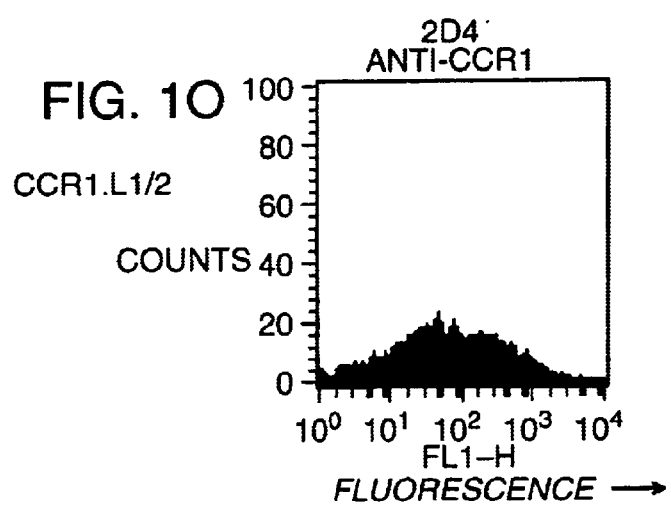
Figure 2F:
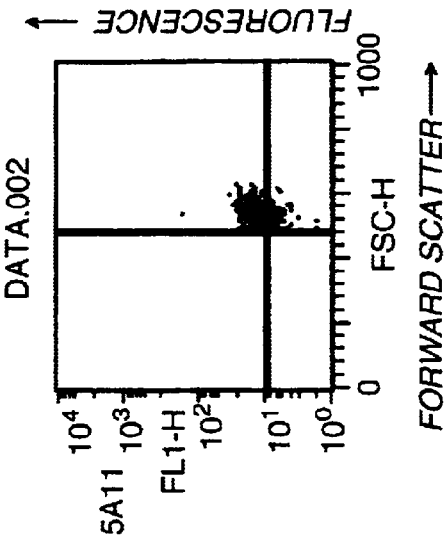
Figure 2E:
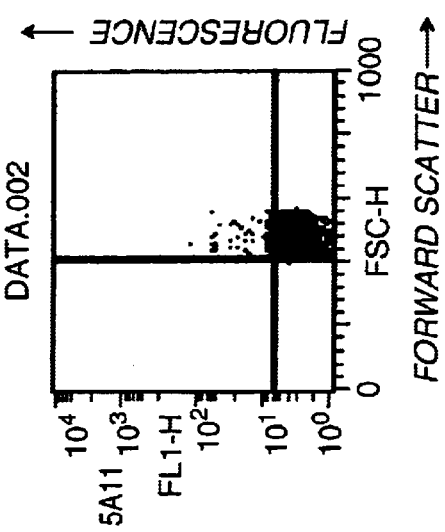
Figure 2D:
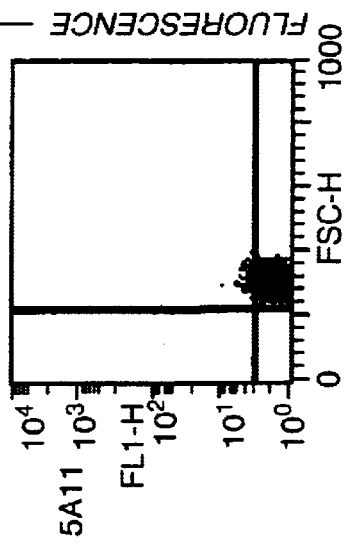
Figure 2I:
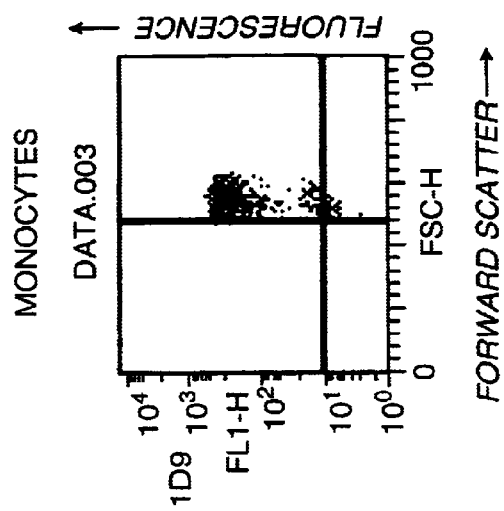
Figure 2H:
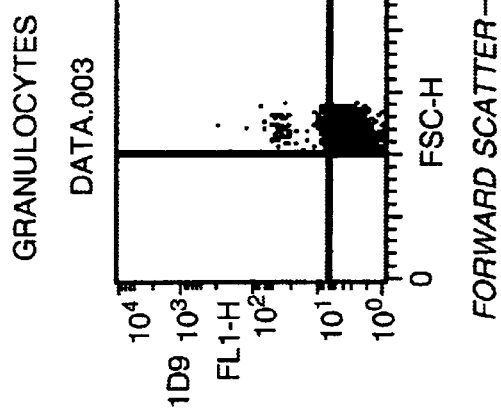
Figure 2G:
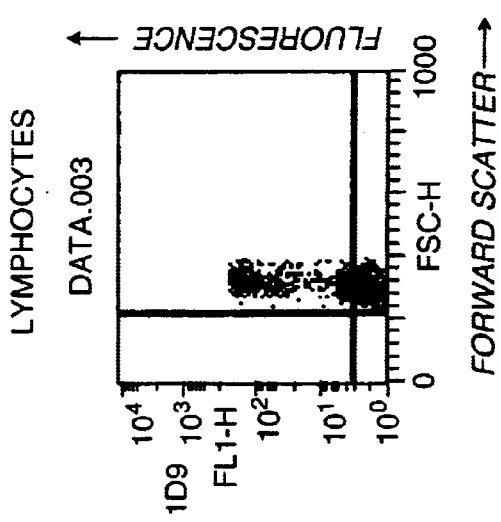
Figure 2L:
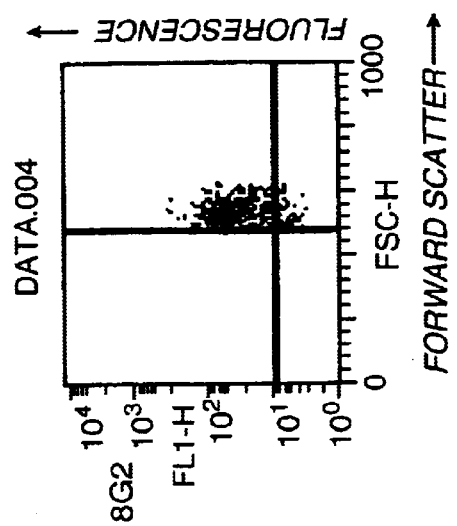
Figure 2K:
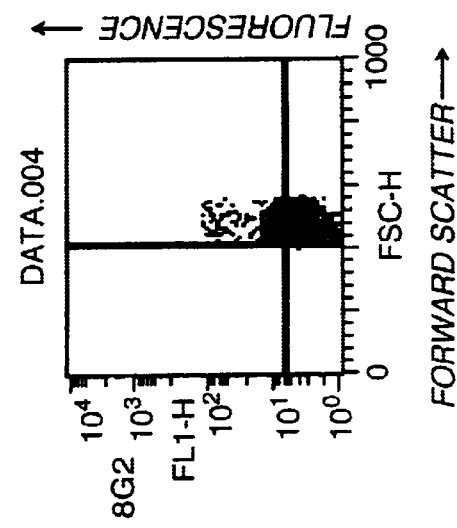
Figure 2J:
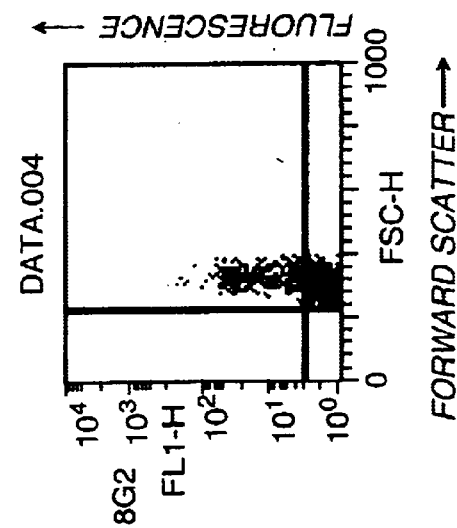
Figure 3A:
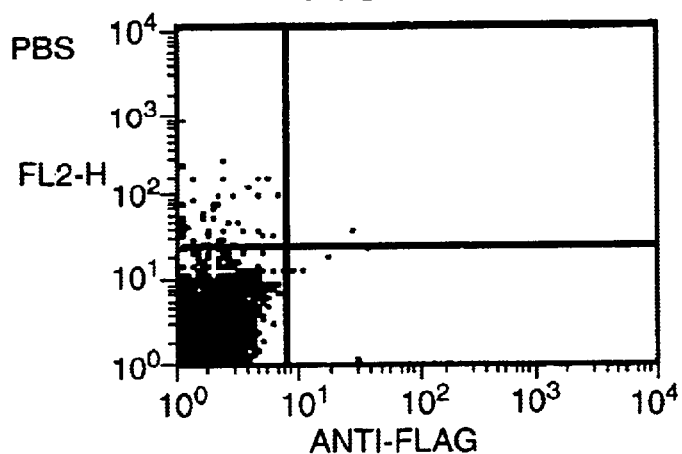
FIGS. 3A-3I are FACS dot plots showing that mAb 1D9 stains an IgE positive population in peripheral blood (basophils) using two-color staining for IgE and CCR2. Whole blood cells were first stained with either a negative control antibody (anti-Flag), anti-CCR2 antibody 1D9, or an anti-CXCR1 antibody, as indicated, and detected by an anti-mouse-FITC conjugate. A second staining was done using either PBS or a biotinylated antibody specific for IgE or CD16, as indicated, and detected with a streptavidin-phycoerythrin. Staining was analyzed by flow cytometry.
Figure 3B:
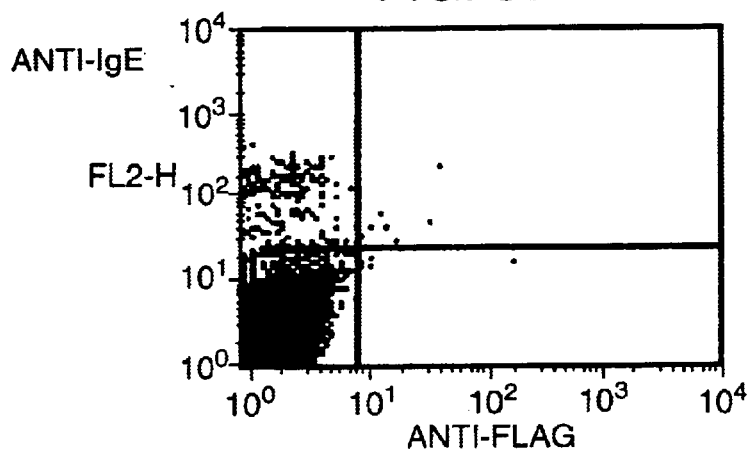
Figure 3C:
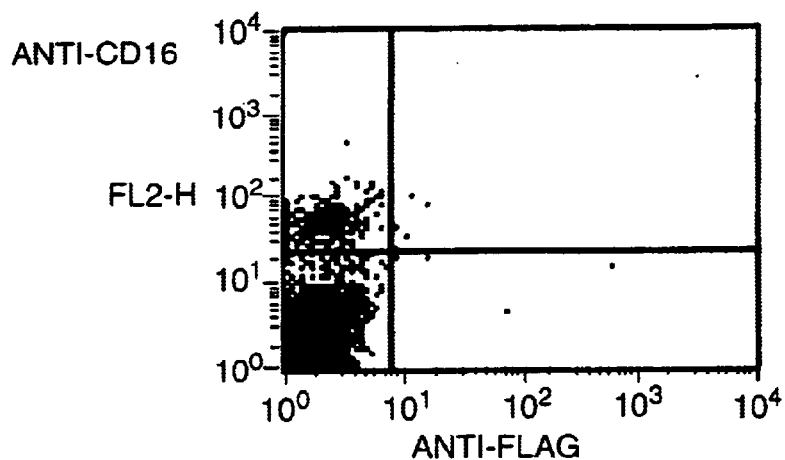
Figure 3D:
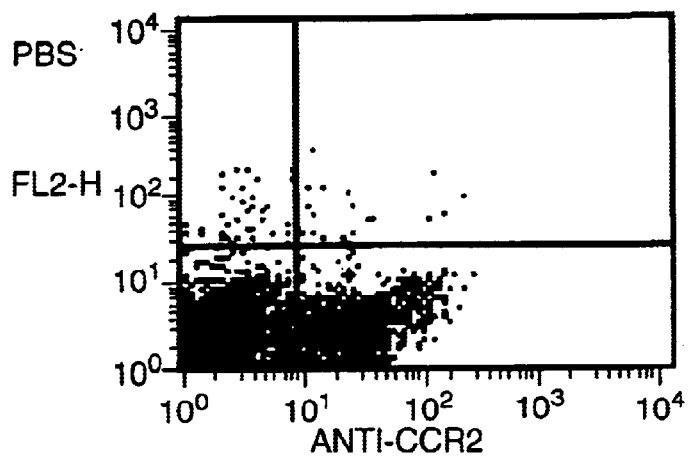
Figure 3E:
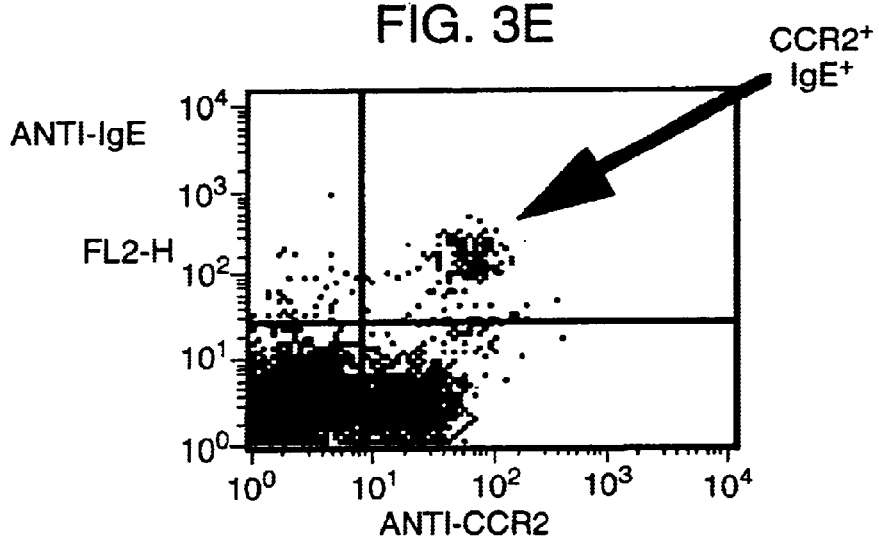
Figure 3F:
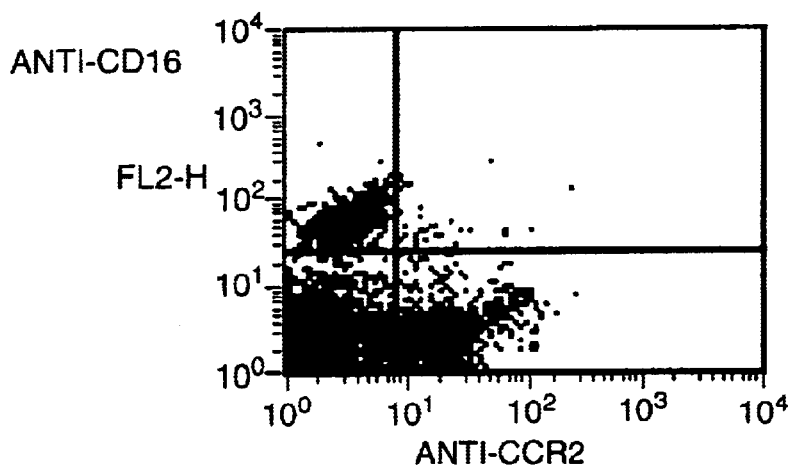
Figure 3G:
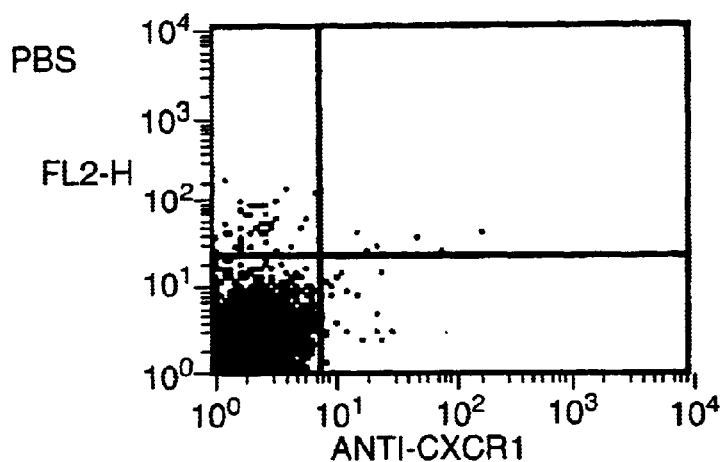
Figure 3H:
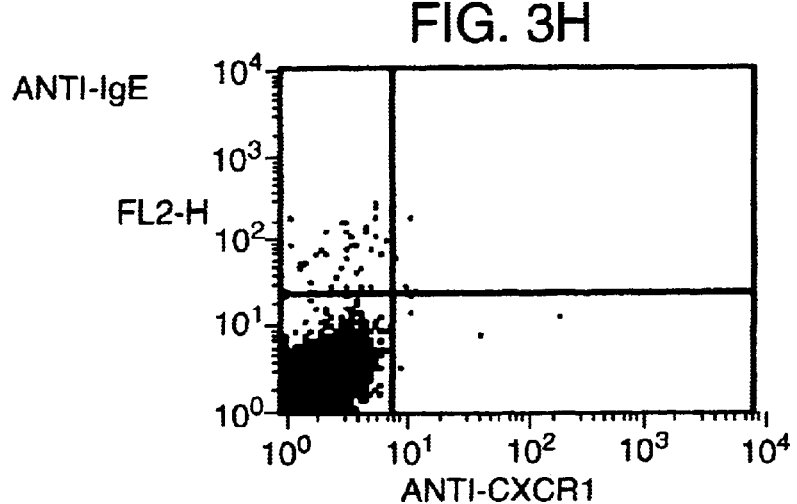
Figure 3I:
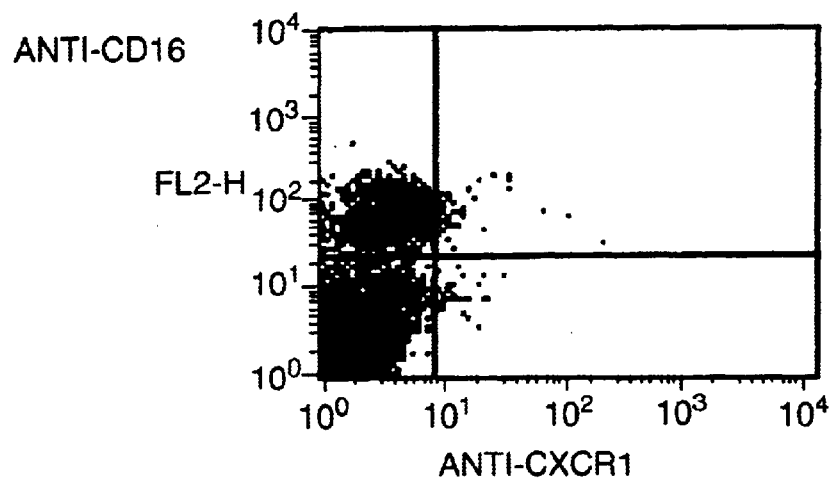

The present invention relates to an antibody (anti-CCR2) or functional fragment thereof which binds mammalian CC-chemokine receptor 2 (CCR2, CKR-2, MCP-1RA or MCP-1RB) or a portion of CCR2. In one embodiment, the antibody has specificity for human or rhesus CCR2 or portion thereof. In one embodiment, the antibodies (immunoglobulins) are raised against an isolated and/or recombinant mammalian CCR2 or portion thereof (e.g., peptide) or against a host cell which expresses mammalian CCR2. In a preferred embodiment, the antibodies specifically bind human CCR2 receptor(s) (e.g., CCR2a and/or CCR2b) or a portion thereof, and in a particularly preferred embodiment the antibodies have specificity for a naturally occurring or endogenous human CCR2. As used herein, "CC-chemokine receptor 2" ("CCR2") refers to CC-chemokine receptor 2a and/or CC-chemokine receptor 2b. Antibodies or functional fragments thereof which can inhibit one or more functions characteristic of a mammalian CCR2, such as a binding activity (e.g., ligand, inhibitor and/or promoter binding), a signaling activity (e.g., activation of a mammalian G protein, induction of a rapid and transient increase in the concentration of cytosolic free calcium [Ca$^{2+}$]i), and/or stimulation of a cellular response (e.g., stimulation of chemotaxis, exocytosis or inflammatory mediator release by leukocytes, integrin activation) are also encompassed by the present invention, such as an antibody which can inhibit binding of a ligand (i.e., one or more ligands) to CCR2 and/or one or more functions mediated by CCR2 in response to a ligand. For example, in one aspect, the antibodies or functional fragments thereof can inhibit (reduce or prevent) the interaction of receptor with a natural ligand, such as MCP-1, MCP-2, MCP-3 and/or MCP-4. In another aspect, an antibody or functional fragment thereof that binds to CCR2 can inhibit binding of MCP-1, MCP-2, MCP-3 and/or MCP-4 and/or HIV to mammalian CCR2 (e.g., human CCR2, non-human primate CCR2, murine CCR2). The antibodies or functional fragments thereof of the present invention can inhibit functions mediated by human CCR2, including leukocyte trafficking, HIV entry into a cell, T cell activation, inflammatory mediator release and/or leukocyte degranulation. Preferably, the antibodies or fragments can bind CCR2 with an affinity of at least about 0.1×10$^{-9}$ M, preferably at least about 1×10$^{-9}$ M, and more preferably at least about 3×10$^{-9}$ M. In a particular embodiment, antibodies or functional fragments thereof demonstrate inhibition of chemokine-induced (e.g., MCP-1-induced) chemotaxis of cells (e.g., PBMC) at less than about 150 μg/ml, preferably less than about 100 μg/ml, more preferably less than about 50 μg/ml, and even more preferably less than about 20 μg/ml.

In a further embodiment of the invention, the antibodies or functional fragments thereof of the invention can inhibit binding of a CCR2 ligand (e.g., a chemokine) to CCR2 with an $IC_{50}$ of less than about 1.0 μg/ml, preferably less than about 0.05 μg/ml, and more preferably less than about 0.005 μg/ml.

Murine monoclonal antibodies specific for CCR2, designated 1D9 and 8G2, were produced as described herein. In a preferred embodiment, the antibodies of the present invention bind human CCR2, and have an epitopic specificity which is the same as or similar to that of murine 1D9 or 8G2 antibody described herein. Antibodies with an epitopic specificity which is the same as or similar to that of murine 1D9 monoclonal antibody can be identified by their ability to compete with murine 1D9 monoclonal antibody for binding to human CCR2 (e.g., to cells bearing human CCR2, such as transfectants bearing CCR2, CD8+ cells, CD4+ cells, CDR45RO+ cells, CD25+ cells, monocytes, dendritic cells, macrophages and basophils). Similarly, antibodies with an epitopic specificity which is the same as or similar to that of murine 8G2 monoclonal antibody can be identified by their ability to compete with murine 8G2 monoclonal antibody for binding to human CCR2. Using receptor chimeras (Rucker et al., Cell 87:437–446 (1996)), the binding site of mAbs 1D9 and 8G2 has been mapped to the amino-terminal domain of human CC-chemokine receptor 2, specifically to an epitope comprising from about amino acid 1 to about amino acid 30 of the protein. Using these or other suitable techniques, antibodies having an epitopic specificity which is the same as or similar to that of an antibody of the present invention can be identified. mAbs 1D9 and 8G2 have epitopic specificity for the amino-terminal domain of the CCR2 receptor, e.g., from about amino acid number 1 to about amino acid number 30 of the receptor protein. Thus, the invention pertains to an antibody or functional portion thereof which binds to the amino-terminal domain or portion thereof of mammalian CC-chemokine receptor 2, and particularly to an epitope comprising from about amino acid 1 to about amino acid 30 of mammalian CC-chemokine receptor 2.

The invention also relates to a bispecific antibody, or functional fragment thereof (e.g., F(ab')$_2$), which has the same or similar epitopic specificity as at least two of the antibodies described herein (see, e.g., U.S. Pat. No. 5,141, 736 (Iwasa et al.), U.S. Pat. Nos. 4,444,878, 5,292,668, 5,523,210 (all to Paulus et al.) and U.S. Pat. No. 5,496,549 (Yamazaki et al.). For example, a bispecific antibody of the present invention can have the same or similar epitopic specificity as mAb 1D9 and 8G2, e.g., binds the amino terminal domain, or portion thereof, of mammalian CCR2 protein.

Hybridoma cell lines producing antibodies according to the present invention were deposited on Jul. 17, 1998, on behalf of LeukoSite, Inc., 215 First Street, Cambridge, Mass. 02142, U.S.A., at the American Type Culture Collection, 10801 University Boulevard, Manassas, Va. 20110, U.S.A., under Accession Nos. HB-12549 (1D9) and HB-12550(8G2). The present invention also pertains to the hybridoma cell lines deposited under ATCC Accession No. HB-12549 and ATCC Accession No. HB-12550, as well as to the monoclonal antibodies produced by the hybridoma cell lines deposited under ATCC Accession Nos. HB-12549 and HB-12550.

The antibodies of the present invention can be polyclonal or monoclonal, and the term "antibody" is intended to encompass both polyclonal and monoclonal antibodies. Furthermore, it is understood that methods described herein which utilize 8G2 can also utilize functional fragments (e.g., antigen-binding fragments) of 8G2, antibodies which have the same or similar epitopic specificity as 8G2, and combinations thereof, optionally in combination with antibodies or fragments having an epitopic specificity which is not the same as or similar to 8G2; similarly, methods described as utilizing 1D9 can also utilize functional fragments of 1D9, antibodies which have the same or similar epitopic specificity as 1D9, and combinations thereof, optionally in combination with antibodies or fragments having an epitopic specificity which is not the same as or similar to 1D9. Antibodies of the present invention can be raised against an appropriate immunogen, such as isolated and/or recombinant mammalian CCR2 protein or portion thereof, or synthetic molecules, such as synthetic peptides. In a preferred embodiment, cells which express receptor, such as transfected cells, can be used as immunogens or in a screen for antibody which binds receptor.

The antibodies of the present invention, and fragments thereof, are useful in therapeutic, diagnostic and research applications as described herein. The present invention encompasses an antibody or functional portion thereof of the present invention (e.g., mAb 1D9 or 8G2, or antigen-binding fragments thereof) for use in therapy (including prophylaxis) or diagnosis (e.g., of particular diseases or conditions as described herein), and use of such antibodies or functional portions thereof for the manufacture of a medicament for use in treatment of diseases or conditions as described herein.

Preparation of immunizing antigen, and polyclonal and monoclonal antibody production can be performed as described herein, or using other suitable techniques. A variety of methods have been described (see e.g., Kohler et al., Nature, 256: 495–497 (1975) and Eur. J. Immunol. 6: 511–519 (1976); Milstein et al., Nature 266: 550–552 (1977); Koprowski et al., U.S. Pat. No. 4,172,124; Harlow, E. and D. Lane, 1988, Antibodies: *A Laboratory Manual*, (Cold Spring Harbor Laboratory: Cold Spring Harbor, N.Y.); *Current Protocols In Molecular Biology*, Vol. 2 (Supplement 27, Summer '94), Ausubel, F. M. et al., Eds., (John Wiley & Sons: New York, N.Y.), Chapter 11, (1991)). Generally, a hybridoma can be produced by fusing a suitable immortal cell line (e.g., a myeloma cell line such as SP2/0) with antibody producing cells. The antibody producing cell, preferably those of the spleen or lymph nodes, are obtained from animals immunized with the antigen of interest. The fused cells (hybridomas) can be isolated using selective culture conditions, and cloned by limiting dilution. Cells which produce antibodies with the desired binding properties can be selected by a suitable assay (e.g., ELISA).

Other suitable methods of producing or isolating antibodies which bind CCR2, including human or artificial antibodies, can be used, including, for example, methods which select recombinant antibody (e.g., single chain Fv or Fab) from a library, or which rely upon immunization of transgenic animals (e.g., mice) capable of producing a repertoire of human antibodies (see e.g., Jakobovits et al., Proc. Natl. Acad. Sci. USA, 90: 2551–2555 (1993); Jakobovits et al., Nature, 362: 255–258 (1993); Lonberg et al., U.S. Pat. No. 5,545,806; Surani et al., U.S. Pat. No. 5,545,807).

Single chain antibodies, and chimeric, humanized or primatized (CDR-grafted) antibodies, as well as chimeric or CDR-grafted single chain antibodies, and the like, comprising portions derived from different species, are also encompassed by the present invention and the term "antibody". The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; and Queen et al., U.S. Pat. Nos. 5,585089, 5,698,761 and 5,698,762. See also, Newman, R. et al., *BioTechnology*, 10: 1455–1460 (1992), regarding primatized antibody, and Ladner et al., U.S. Pat. No. 4,946,778 and Bird, R. E. et al., *Science*, 242: 423–426 (1988)) regarding single chain antibodies.

In addition, functional fragments of antibodies, including fragments of chimeric, humanized, primatized or single chain antibodies, can also be produced. Functional fragments of the foregoing antibodies retain at least one binding function and/or modulation function of the full-length antibody from which they are derived. Preferred functional fragments retain an antigen-binding function of a corresponding full-length antibody (e.g., the ability to bind a mammalian CCR2). Particularly preferred functional fragments retain the ability to inhibit one or more functions characteristic of a mammalian CCR2, such as a binding activity, a signaling activity, and/or stimulation of a cellular response. For example, in one embodiment, a functional fragment can inhibit the interaction of CCR2 with one or more of its ligands (e.g., MCP-1, MCP-2, MCP-3 and/or MCP-4) and/or can inhibit one or more receptor-mediated functions, such as leukocyte trafficking, HIV entry into cells, T cell activation, inflammatory mediator release and/or leukocyte degranulation.

For example, antibody fragments capable of binding to a mammalian CCR2 receptor or portion thereof, including, but not limited to, Fv, Fab, Fab' and F(ab')$_2$ fragments are encompassed by the invention. Such fragments can be produced by enzymatic cleavage or by recombinant techniques, for example. For instance, papain or pepsin cleavage can generate Fab or F(ab')$_2$ fragments, respectively. Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH$_1$ domain and hinge region of the heavy chain.

The present invention relates to a humanized immunoglobulin or antigen-binding fragment thereof having binding specificity for CCR2, comprising an antigen binding region of nonhuman origin (e.g., rodent) and at least a portion of an immunoglobulin of human origin (e.g., a human framework region, a human constant region or portion thereof). In one embodiment, the humanized immunoglobulin includes an antigen binding region of nonhuman origin which binds CCR2 and a constant region derived from a human constant region. In another embodiment, the humanized immunoglobulin which binds CCR2 comprises a complementarity determining region of nonhuman origin and a variable framework region of human origin, and optionally, a constant region of human origin. For example, the humanized immunoglobulin can comprise a heavy chain and a light chain, wherein the light chain comprises a complementarity determining region derived from an antibody of nonhuman origin which binds CCR2 and a framework region derived from a light chain of human origin, and the heavy chain comprises a complementarity determining region derived from an antibody of nonhuman origin which binds CCR2 and a framework region derived from a heavy chain of human origin.

In one embodiment, the humanized immunoglobulin can compete with murine 1D9 or 8G2 monoclonal antibody for binding to human CCR2. In a preferred embodiment, the antigen-binding region of the humanized immunoglobulin (a) is derived from 1D9 monoclonal antibody (e.g., as in a humanized immunoglobulin comprising CDR1, CDR2 and CDR3 of the 1D9 light chain and/or CDR1, CDR2 and CDR3 of the 1D9 heavy chain) or (b) is derived from 8G2 monoclonal antibody (e.g., as in a humanized immunoglobulin comprising CDR1, CDR2 and CDR3 of the 8G2 light chain and/or CDR1, CDR2 and CDR3 of the 8G2 heavy chain). Chimeric or CDR-grafted single chain antibodies are also encompassed by the term humanized immunoglobulin.

The present invention also relates to a humanized immunoglobulin light chain or antigen-binding fragment thereof or a humanized immunoglobulin heavy chain or antigen-binding fragment thereof. In one embodiment, the invention relates to a humanized light chain comprising a light chain CDR (i.e., one or more CDRs) of nonhuman origin and a human light chain framework region. In another embodiment, the present invention relates to a humanized immnunoglobulin heavy chain comprising a heavy chain CDR (i.e., one or more CDRs) of nonhuman origin and a human heavy chain framework region. The CDRs can be derived from a nonhuman immunoglobulin.

Naturally occurring immunoglobulins have a common core structure in which two identical light chains (about 24 kD) and two identical heavy chains (about 55 or 70 kD) form a tetramer. The amino-terminal portion of each chain is known as the variable (V) region and can be distinguished from the more conserved constant (C) regions of the remainder of each chain. Within the variable region of the light chain is a C-terminal portion known as the J region. Within the variable region of the heavy chain, there is a D region in addition to the J region. Most of the amino acid sequence variation in immunoglobulins is confined to three separate locations in the V regions known as hypervariable regions or complementarity determining regions (CDRs) which are directly involved in antigen binding. Proceeding from the amino-terminus, these regions are designated CDR1, CDR2 and CDR3, respectively. The CDRs are held in place by more conserved framework regions (FRs). Proceeding from the amino-terminus, these regions are designated FR1, FR2, FR3, and FR4, respectively. The locations of CDR and FR regions and a numbering system have been defined by Kabat et al. (Kabat et al., *Sequences of Proteins of Immunological Interest*, Fifth Edition, U.S. Department of Health and Human Services, U.S. Government Printing Office (1 991)).

Human immunoglobulins can be divided into classes and subclasses, depending on the isotype of the heavy chain. The classes include IgG, IgM, IgA, IgD and IgE, in which the heavy chains are of the gamma ($\gamma$), mu ($\mu$), alpha ($\alpha$), delta ($\delta$) or epsilon ($\epsilon$) type, respectively. Subclasses include IgG1, IgG2, IgG3, IgG4, IgA1 and IgA2, in which the heavy chains are of the $\gamma$1, $\gamma$2, $\gamma$3, $\gamma$4, $\alpha$1 and $\alpha$2 type, respectively. Human immunoglobulin molecules of a selected class or subclass may contain either a kappa ($\kappa$) or lambda ($\lambda$) light chain. See e.g., *Cellular and Molecular Immunology*, Wonsiewicz, M. J., Ed., Chapter 45, pp. 41–50, W. B. Saunders Co, Philadelphia, Pa. (1991); Nisonoff, A., *Introduction to Molecular Immunology*, 2nd Ed., Chapter 4, pp. 45–65, Sinauer Associates, Inc., Sunderland, Mass. (1984).

The term "immunoglobulin" as used herein includes whole antibodies and biologically functional fragments thereof. Such biologically functional fragments retain at least one antigen-binding function of a corresponding full-length antibody (e.g., specificity for CCR2 of antibody 1D9), and preferably, retain the ability to inhibit the interaction of CCR2 with one or more of its ligands (e.g., HIV, MCP-1, MCP-2, MCP-3, MCP-4). Examples of biologically functional antibody fragments which can be used include fragments capable of binding to CCR2, such as single chain antibodies, $F_v$, Fab, Fab' and $F(ab')_2$ fragments. Such fragments can be produced by enzymatic cleavage or by recombinant techniques. For instance, papain or pepsin cleavage can be used to generate Fab or $F(ab')_2$ fragments, respectively. Antibodies can also be produced in a variety of truncated forms using antibody genes in which one or more stop codons have been introduced upstream of the natural stop site. For example, a chimeric gene encoding the heavy chain of an $F(ab')_2$ fragment can be designed to include DNA sequences encoding the $CH_1$ domain and hinge region of the heavy chain. As used herein, an antigen-binding fragment of a humanized immunoglobulin heavy or light chain is intended to mean a fragment which binds to an antigen when paired with a complementary chain. That is, an antigen-binding fragment of a humanized light chain will bind to an antigen when paired with a heavy chain (e.g., murine, chimeric, humanized) comprising a variable region, and an antigen-binding fragment of a humanized heavy chain will bind to an antigen when paired with a light chain (e.g., murine, chimeric, humanized) comprising a variable region.

The term "humanized immunoglobulin" as used herein refers to an immunoglobulin comprising portions of immunoglobulins of different origin, wherein at least one portion is of human origin. For example, the humanized antibody can comprise portions derived from an immunoglobulin of nonhuman origin with the requisite specificity, such as a mouse, and from immunoglobulin sequences of human origin (e.g., chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized immunoglobulin of the present invention is an immunoglobulin containing one or more immunoglobulin chains comprising a CDR derived from an antibody of nonhuman origin and a framework region derived from a light and/or heavy chain of human origin (e.g., CDR-grafted antibodies with or without framework changes). Chimeric or CDR-grafted single chain antibodies are also encompassed by the term humanized immunoglobulin. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519,596 A1. See also, Ladner et al., U.S. Pat. No. 4,946,778; Huston, U.S. Pat. No. 5,476,786; and Bird, R. E. et al., *Science*, 242: 423–426 (1988)), regarding single chain antibodies.

For example, humanized immunoglobulins can be produced using synthetic and/or recombinant nucleic acids to prepare genes (e.g., cDNA) encoding the desired humanized chain. For example, nucleic acid (e.g., DNA) sequences coding for humanized variable regions can be constructed using PCR mutagenesis methods to alter DNA sequences encoding a human or humanized chain, such as a DNA template from a previously humanized variable region (see e.g., Kamman, M., et al., *Nucl. Acids Res.*, 17: 5404 (1989)); Sato, K., et al., *Cancer Research*, 53: 851–856 (1993); Daugherty, B. L. et al., *Nucleic Acids Res.*, 19(9): 2471–2476 (1991); and Lewis, A. P. and J. S. Crowe, *Gene*, 101: 297–302 (1991)). Using these or other suitable methods, variants can also be readily produced. In one embodiment, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993)).

The antigen binding region of the humanized immunoglobulin (the nonhuman portion) can be derived from an immunoglobulin of nonhuman origin (referred to as a donor immunoglobulin) having binding specificity for CCR2. For example, a suitable antigen binding region can be derived from the murine monoclonal antibody 1D9. Other sources include CCR2-specific antibodies obtained from nonhuman sources, such as rodent (e.g., mouse, rat), rabbit, pig goat or non-human primate (e.g., monkey). Additionally, other polyclonal or monoclonal antibodies, such as antibodies which bind to the same or similar epitope as the 1D9 antibody, can be made (e.g., Kohler et al., *Nature*, 256:495–497 (1975); Harlow et al., 1988, Antibodies: A Laboratory Manual, (Cold Spring Harbor, N.Y.); and Current Protocols in Molecular Biology, Vol. 2 (Supplement 27, Summer '94), Ausubel et al., Eds. (John Wiley & Sons: N.Y., N.Y.), Chapter 11 (1991)).

For example, antibodies can be raised against an appropriate immunogen in a suitable mammal (e.g., a mouse, rat, rabbit or sheep). Cells bearing CCR2, membrane fractions containing CCR2, and immunogenic fragments of CCR2 are examples of suitable immunogens. Antibody-producing cells (e.g., a lymphocyte) can be isolated from, for example, the lymph nodes or spleen of an immunized animal. The cells can then be fused to a suitable immortalized cell (e.g., a myeloma cell line), thereby forming a hybridoma. Fused cells can be isolated employing selective culturing techniques. Cells which produce antibodies with the desired specificity can be selected by a suitable assay (e.g., ELISA). Immunoglobulins of nonhuman origin having binding specificity for CCR2 can also be obtained from antibody libraries (e.g., a phage library comprising nonhuman Fab molecules).

In one embodiment, the antigen binding region of the humanized immunoglobulin comprises a CDR of nonhuman origin. In this embodiment, the humanized immunoglobulin having binding specificity for CCR2 comprises at least one CDR of nonhuman origin. For example, CDRs can be derived from the light and heavy chain variable regions of immunoglobulins of nonhuman origin, such that a humanized immunoglobulin includes substantially heavy chain CDR1, CDR2 and/or CDR3, and/or light chain CDR1, CDR2 and/or CDR3, from one or more immunoglobulins of nonhuman origin, and the resulting humanized immunoglobulin has binding specificity for CCR2. Preferably, all three CDRs of a selected chain are substantially the same as the CDRs of the corresponding chain of a donor, and more preferably, all three CDRs of the light and heavy chains are substantially the same as the CDRs of the corresponding donor chain. In one embodiment, the invention relates to an immunoglobulin having binding specificity for CCR2 comprising a humanized light chain or antigen-binding fragment thereof comprising CDR1, CDR2 and CDR3 of the light chain of the 1D9 antibody and a heavy chain, e.g., a human heavy chain. The invention also includes an immunoglobulin having binding specificity for CCR2 comprising a humanized heavy chain or antigen-binding fragment thereof comprising CDR1, CDR2 and CDR3 of the heavy chain of the 1D9 antibody and a light chain, e.g., a human light chain.

The invention also relates to an immunoglobulin having binding specificity for CCR2 comprising a light chain and a heavy chain, wherein the light chain comprises at least 1 CDR of an antibody of non-human origin (e.g., 1D9) and framework and constant regions of human origin (e.g., SEQ ID NO: 12, SEQ ID NO: 13, SEQ ID NO: 14 and SEQ ID NO: 15), and wherein the heavy chain comprises a variable region of non-human origin (e.g., from 1D9) and a constant region of human origin. The invention also provides antigen-binding fragments of these immunoglobulins. The invention also relates to an immunoglobulin having binding specificity for CCR2 comprising a light chain and a heavy chain, wherein the light chain comprises a variable chain of non-human origin (e.g., from 1D9) and a constant region of human origin, and wherein the heavy chain comprises at least 1 CDR of an antibody of non-human origin (e.g., 1D9) and framework and constant regions of human origin (e.g., SEQ ID NO: 17, SEQ ID NO: 18, SEQ ID NO:19 and SEQ ID NO: 20). The invention also provides antigen-binding fragments of these immunoglobulins.

The portion of the humanized immunoglobulin or immunoglobulin chain which is of human origin (the human portion) can be derived from any suitable human immunoglobulin or immunoglobulin chain. For example, a human constant region or portion thereof, if present, can be derived from the κ or λ light chains, and/or the γ (e.g., γ1, γ2, γ3, γ4), μ, α (e.g., α1, α2), δ or ε heavy chains of human antibodies, including allelic variants. A particular constant region (e.g., IgG1), variant or portions thereof can be selected in order to tailor effector function. For example, a mutated constant region (variant) can be incorporated into a fusion protein to minimize binding to Fc receptors and/or ability to fix complement (see e.g., Winter et al., GB 2,209,757 B; Morrison et al., WO 89/07142; Morgan et al., WO 94/29351, Dec. 22, 1994).

If present, human framework regions (e.g., of the light chain variable region) are preferably derived from a human antibody variable region having sequence similarity to the analogous or equivalent region (e.g., light chain variable region) of the antigen binding region donor. Other sources of framework regions for portions of human origin of a humanized immunoglobulin include human variable consensus sequences (see, e.g., Kettleborough, C. A. et al., *Protein Engineering* 4:773–783 (1991); Carter et al., WO 94/04679, published Mar. 3, 1994)). For example, the sequence of the antibody or variable region used to obtain the nonhuman portion can be compared to human sequences as described in Kabat et al., *Sequences of Proteins of immunological Interest*, Fifth Edition, U.S. Department of Health and Human Services, U.S. Government Printing Office (1991). In a particularly preferred embodiment, the framework regions of a humanized immunoglobulin chain are derived from a human variable region having at least about 60% overall sequence identity, preferably at least about 70% overall sequence identity and more preferably at least about 85% overall sequence identity, with the variable region of the nonhuman donor (e.g., murine antibody 1D9). A human portion can also be derived from a human antibody having at least about 65% sequence identity, and preferably at least about 70% sequence identity, within the particular portion (e.g., FR) being used, when compared to the equivalent portion (e.g., FR) of the nonhuman donor.

In one embodiment, the humanized immunoglobulin comprises at least one of the framework regions (FR) derived from one or more chains of an antibody of human origin. Thus, the FR can include a FR1 and/or FR2 and/or FR3 and/or FR4 derived from one or more antibodies of human origin. Preferably, the human portion of a selected humanized chain includes FR1, FR2, FR3 and FR4 derived from a variable region of human origin (e.g., from a human immunoglobulin chain, from a human consensus sequence).

The immunoglobulin portions of nonhuman and human origin for use in the present invention have sequences identical to immunoglobulins or immunoglobulin portions from which they are derived or to variants thereof. Such variants include mutants differing by the addition, deletion, or substitution of one or more residues. As indicated above, the CDRs which are of nonhuman origin are substantially the same as in the nonhuman donor, and preferably are identical to the CDRs of the nonhuman donor. As described in Example 2, changes in the framework region, such as those which substitute a residue of the framework region of human origin with a residue from the corresponding position of the donor, can be made. One or more mutations in the framework region can be made, including deletions, insertions and substitutions of one or more amino acids. Several such substitutions are described in the design of humanized 1D9 antibodies in Example 2. For a selected humanized antibody or chain, framework mutations can be designed as described herein. Preferably, the humanized immunoglobulins can bind CCR2 with an affinity similar to or better than that of the nonhuman donor. Variants can be produced by a variety of suitable methods, including mutagenesis of non-human donor or acceptor human chains.

The humanized immunoglobulins of the present invention have binding specificity for human CCR2. In a preferred embodiment, the humanized immunoglobulin of the present invention has at least one functional characteristic of murine antibody 1D9, such as binding function (e.g., having specificity for CCR2, having the same or similar epitopic specificity), and/or inhibitory function (e.g., the ability to inhibit CCR2-dependent function in vitro and/or in vivo, such as the ability to inhibit the binding of a cell bearing CCR2 to a ligand thereof (e.g., a chemokine)). Thus, preferred humanized immunoglobulins can have the binding specificity of the murine antibody 1D9, the epitopic specificity of murine antibody 1D9 (e.g., can compete with murine 1D9, a chimeric 1D9 antibody, or humanized 1D9 for binding to CCR2 (e.g., on a cell bearing CCR2)), and/or inhibitory function of murine antibody 1D9.

The binding function of a humanized immunoglobulin having binding specificity for CCR2 can be detected by standard immunological methods, for example using assays which monitor formation of a complex between humanized immunoglobulin and CCR2 (e.g., a membrane fraction comprising CCR2, on a cell bearing CCR2, human cell line or recombinant host cell comprising nucleic acid encoding CCR2 which expresses CCR2). Binding and/or adhesion assays or other suitable methods can also be used in procedures for the identification and/or isolation of humanized immunoglobulins (e.g., from a library) with the requisite specificity (e.g., an assay which monitors adhesion between a cell bearing CCR2 and a ligand thereof (e.g., HIV, MCP-1, MCP-2, MCP-3, MCP-4), or other suitable methods.

The immunoglobulin portions of nonhuman and human origin for use in the present invention include light chains, heavy chains and portions of light and heavy chains. These immunoglobulin portions can be obtained or derived from immunoglobulins (e.g., by de novo synthesis of a portion), or nucleic acid molecules encoding an immunoglobulin or chain thereof having the desired property (e.g., binding CCR2, sequence similarity) can be produced and expressed. Humanized immunoglobulins comprising the desired portions (e.g., antigen binding region, CDR, FR, C region) of human and nonhuman origin can be produced using synthetic and/or recombinant nucleic acids to prepare genes (e.g., cDNA) encoding the desired humanized chain. To prepare a portion of a chain, one or more stop codons can be introduced at the desired position. For example, nucleic acid (e.g., DNA) sequences coding for newly designed humanized variable regions can be constructed using PCR mutagenesis methods to alter existing DNA sequences (see e.g., Kamman, M., et al., *Nucl. Acids Res.* 17:5404(1989)). PCR primers coding for the new CDRs can be hybridized to a DNA template of a previously humanized variable region which is based on the same, or a very similar, human variable region (Sato, K., et al., *Cancer Research* 53:851–856 (1993)). If a similar DNA sequence is not available for use as a template, a nucleic acid comprising a sequence encoding a variable region sequence can be constructed from synthetic oligonucleotides (see e.g., Kolbinger, F., *Protein Engineering* 8:971–980 (1993)). A sequence encoding a signal peptide can also be incorporated into the nucleic acid (e.g., on synthesis, upon insertion into a vector). If the natural signal peptide sequence is unavailable, a signal peptide sequence from another antibody can be used (see, e.g., Kettleborough, C. A., *Protein Engineering* 4:773–783 (1991)). Using these methods, methods described herein or other suitable methods, variants can be readily produced. In one embodiment, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993)).

The invention relates to a humanized immunoglobulin light chain or antigen-binding fragment thereof, said light chain or antigen-binding fragment thereof having an amino acid sequence comprising at least a functional portion of the light chain variable region amino acid sequence of SEQ ID NO: 9. In a preferred embodiment, the amino acid sequence comprises at least one, preferably two, and more preferably three of the CDRs of SEQ ID NO: 9. The invention also relates to a humanized immunoglobulin heavy chain or antigen-binding fragment thereof, said heavy chain or antigen-binding fragment thereof having an amino acid sequence comprising at least a functional portion of the heavy chain variable region amino acid sequence shown in SEQ ID NO: 10. In a preferred embodiment, the amino acid sequence comprises at least one, preferably two, and more preferably three of the CDRs of SEQ ID NO: 10. It is noted that all murine sequences described herein are derived from *Mus musculus*.

According to one embodiment of the invention, a humanized immunoglobulin light chain or antigen-binding fragment thereof having binding specificity for CCR2 can comprise an amino acid sequence selected from the group consisting of SEQ ID NO: 12, SEQ ID NO: 13, SEQ ID NO: 14, and SEQ ID NO: 15. According to another embodiment of the invention, a humanized immunoglobulin heavy chain or antigen-binding fragment thereof having binding specificity for CCR2 can comprise an amino acid sequence selected from the group consisting of SEQ ID NO: 17, SEQ ID NO: 18, SEQ ID NO: 19, and SEQ ID NO: 20. In a particular embodiment, a humanized immunoglobulin of the invention can comprise both a light chain or antigen-binding fragment thereof having binding specificity for CCR2, comprising an amino acid sequence selected from the group consisting of SEQ ID NO: 12, SEQ ID NO: 13, SEQ ID NO: 14, and SEQ ID NO: 15, and a heavy chain or antigen-binding fragment thereof having binding specificity for CCR2 comprising an amino acid sequence selected from the group consisting of SEQ ID NO: 17, SEQ ID NO: 18, SEQ ID NO: 19, and SEQ ID NO: 20. In one embodiment, the humanized immunoglobulin light chain or antigen-binding fragment thereof having binding specificity for CCR2 can be encoded by a nucleic acid molecule comprising SEQ ID NO: 98. In another embodiment, the humanized immunoglobulin heavy chain or antigen-binding fragment thereof having binding specificity for CCR2 can be encoded by a nucleic acid molecule comprising SEQ ID NO: 97.

The invention also relates to a chimeric immunoglobulin or antigen-binding fragment thereof having binding specificity for CCR2 comprising a light chain variable region of nonhuman origin and a human constant region (e.g., a light chain constant region). The invention further relates to a chimeric immunoglobulin or antigen-binding fragment thereof having binding specificity for CCR2 comprising a heavy chain variable region of nonhuman origin and a human constant region (e.g., a heavy chain constant region). In another embodiment, the chimeric immunoglobulin or antigen-binding fragment thereof having binding specificity for CCR2 comprises a light chain variable chain region of nonhuman origin and a heavy chain variable region of nonhuman origin and further comprises a human constant region (e.g., a human light chain constant region and/or a human heavy chain constant region).

Nucleic Acids and Constructs

The present invention also relates to isolated and/or recombinant (including, e.g., essentially pure) nucleic acid molecules comprising nucleic acid sequences which encode a humanized immunoglobulin or humanized immunoglobulin light or heavy chain of the present invention.

Nucleic acid molecules referred to herein as "isolated" are nucleic acid molecules which have been separated away from the nucleic acids of the genomic DNA or cellular RNA of their source of origin (e.g., as it exists in cells or in a mixture of nucleic acids such as a library), and include nucleic acid molecules obtained by methods described herein or other suitable methods, including essentially pure nucleic acid molecules, nucleic acid molecules produced by chemical synthesis, by combinations of biological and chemical methods, and recombinant nucleic acid molecules which are isolated (see e.g., Daugherty, B. L. et al., *Nucleic Acids Res.*, 19(9): 2471–2476 (1991); Lewis, A. P. and J. S. Crowe, *Gene*, 101: 297–302 (1991)).

Nucleic acid molecules referred to herein as "recombinant" are nucleic acid molecules which have been produced by recombinant DNA methodology, including those nucleic acid molecules that are generated by procedures which rely upon a method of artificial recombination, such as the polymerase chain reaction (PCR) and/or cloning into a vector using restriction enzymes. "Recombinant" nucleic acid molecules are also those that result from recombination events that occur through the natural mechanisms of cells, but are selected for after the introduction to the cells of nucleic acids designed to allow and make probable a desired recombination event.

Figure 21:
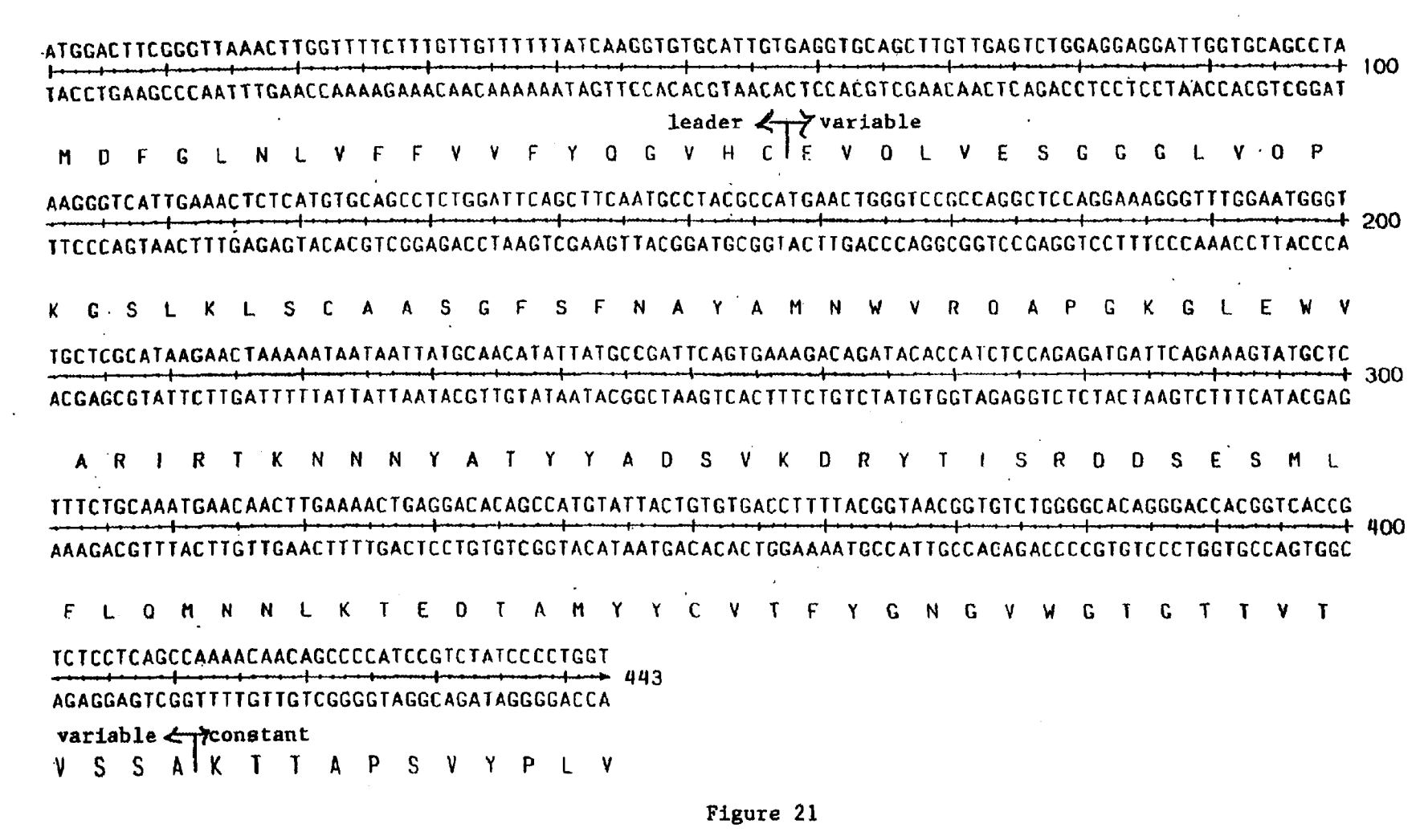

The present invention also relates more specifically to isolated and/or recombinant nucleic acid molecules comprising a nucleotide sequence which encodes a humanized 1D9 immunoglobulin (i.e., a humanized immunoglobulin of the present invention in which the nonhuman portion is derived from the murine monoclonal antibody 1D9) or chain thereof. In one embodiment, the light chain comprises three complementarity determining regions derived from the light chain of the 1D9 antibody, and the heavy chain comprises three complementarity determining regions derived from the heavy chain of the 1D9 antibody. Such nucleic acid molecules include, for example, (a) a nucleic acid molecule comprising a sequence which encodes a polypeptide comprising the amino acid sequence of the heavy chain variable region of a humanized 1D9 immunoglobulin (e.g., heavy chain variable region of FIGS. 8 and 21) (e.g., nucleotides 58–411 of SEQ ID NO: 96); (b) a nucleic acid molecule comprising a sequence which encodes a polypeptide comprising the amino acid sequence of the light chain variable region of a humanized 1D9 immunoglobulin (e.g., light chain variable region of FIGS. 7 and 22) (e.g., nucleotides 52–390 of SEQ ID NO: 95); (c) a nucleic acid molecule comprising a sequence which encodes at least a functional portion of the light or heavy chain variable region of a humanized 1D9 immunoglobulin (e.g., a portion sufficient for antigen binding of a humanized immunoglobulin which comprises said chain). Due to the degeneracy of the genetic code, a variety of nucleic acids can be made which encode a selected polypeptide. In one embodiment, the nucleic acid comprises the nucleotide sequence of the variable region as set forth or substantially as set forth in FIG. 21 or as set forth or substantially as set forth in FIG. 22, including double or single-stranded polynucleotides. (Although various figures may illustrate polypeptides which are larger than the variable region (i.e., include a signal peptide coding sequence or a portion of a constant region coding sequence), reference to the variable region of a particular figure is meant to include the variable region portion of the sequence shown). Isolated and/or recombinant nucleic acid molecules meeting these criteria can comprise nucleic acid molecules encoding sequences identical to sequences of humanized 1D9 antibody or variants thereof as discussed above.

Nucleic acid molecules of the present invention can be used in the production of humanized immunoglobulins having binding specificity for CCR2. For example, a nucleic acid molecule (e.g., DNA) encoding a humanized immunoglobulin of the present invention can be incorporated into a suitable construct (e.g., a vector) for further manipulation of sequences or for production of the encoded polypeptide in suitable host cells.

Targeting Molecules

The invention also relates to targeting molecules which can effectuate the interaction of a CCR2-expressing cell with a target cell. The targeting molecule includes a first binding moiety which can bind mammalian CCR2, and a second binding moiety which can bind a molecule expressed on the surface of a target cell. Preferred target cells include tumor cells and virus infected cells. A variety of molecules which are expressed at higher levels or uniquely on tumor cells (e.g., tumor antigens, such as Lewis Y, HER-2/neu, disialoganglioside G3, carcinoembrionic antigen, CD30) and/or virus infected cells (e.g., viral antigens, such as influenza virus hemagglutinin, Epstein-Barr virus LMP-1, hepatitis C virus E2 glycoprotein, HIV gp160, HIV gp120) are known in the art. The targeting molecule can contain any suitable binding second moiety which binds to a molecule expressed on a desired target cell (see, for example Ring, U.S. Pat. No. 5,948,647, the entire teachings of which are incorporated herein by reference). Suitable binding moieties include, for example, proteins and peptides (including post-translationally modified forms e.g. glycosylated, phosphorylated, lipidated), sugars, lipids, peptidomimetics, small organic molecules, nucleic acids and other agents which bind mammalian CCR2 or a molecule expressed on the surface of a target cell. Suitable binding moieties can be identified using any suitable method, such as the binding assays described herein.

In a preferred embodiment, the first binding moiety can be, for example, a humanized immunoglobulin of the invention which binds mammalian CCR2 or antigen-binding fragment thereof (e.g., Fab, Fv, Fab', F(ab)'$_2$). The second binding moiety can be, for example, an antibody (e.g., a second humanized immunoglobulin) or antigen-binding fragment thereof which binds to a molecule expressed on the target cell or antigen binding fragment thereof. Where the targeting molecule comprises a first binding moiety which is a humanized anti-CCR2 immunoglobulin or antigen-binding fragment thereof, it is preferred that the humanized anti-CCR2 immunoglobulin does not inhibit binding of ligand to CCR2.

The first binding moiety can be directly or indirectly bonded to the second binding moiety through a variety of suitable linkages. For example, when the first binding moiety and the second binding moiety are both proteins or peptides, the moieties can be part of a contiguous polypeptide (i.e., a fusion protein). Where the targeting molecule is a fusion protein, the first and second binding moieties can be arranged on the polypeptide in any suitable configuration. The first and second binding moieties can be indirectly bonded through a (i.e., one or more) peptide linker, or bonded directly to each other through a peptide bond.

Where the binding moieties are not part of a contiguous polypeptide they can be directly bonded by a chemical bond formed by reaction of a functional group (or activated derivative thereof) on the first moiety with a second functional group (or activated derivative thereof) on the second moiety. For example, two thiols can react to form a disulfide bond and an amine can react with a carboxylic acid or acyl halide to form an amide. A variety of other suitable reactions which can be used are known in the art (see, for example, Hermanson, G. T., *Bioconjugate Techniques*, Academic Press: San Diego, Calif. (1996)). The binding moieties can be indirectly bonded through a suitable linker (e.g., a peptide linker). Generally, a linker contains two reactive groups which can react to form bonds with the first binding moiety and/or the second binding moiety. Linkers which contain two different reactive groups (e.g., a heterobifunctional linker) can be used to selectively conjugate the first binding moiety to the second binding moiety. Many linkers which are suitable for forming conjugates between proteins, nucleic acids, peptides, vitamins, sugars, lipids, small organic molecules and other suitable agents are known (see, for example, U.S. Pat. Nos. 5,856,571, 5,880,270; Hermanson, G. T., *Bioconjugate Techniques*, Academic Press: San Diego, Calif. (1996)).

Preferably, the independent activities of the binding moieties (e.g., binding activities, chemoattractant activity) of the targeting molecule are not significantly different from the activities of the binding moieties as separate molecular entities. For example, where the first binding moiety is a humanized immunoglobulin or antigen-binding fragment that binds CCR2, the targeting molecule can bind to CCR2 with an affinity which is within a factor of about 1000, preferably within a factor of 100, more preferably within a factor of 10 or substantially the same as the affinity of the free antibody or antigen-binding fragment. Target molecules with these preferred characteristics can be prepared using any suitable method. The resulting targeting molecule can then be assayed for binding (e.g., by ELISA) and for chemoattractant activity.

In one embodiment, the targeting molecule is a bispecific humanized antibody or bispecific antigen-binding fragment thereof (e.g., F(ab')$_2$) which has specificity for mammalian CCR2 and a molecule expressed on a target cell (e.g., tumor antigen, viral antigen). Bispecific antibodies can be secreted by triomas and hybrid hybridomas. The supernatants of triomas and hybrid hybridomas can be assayed for bispecific antibody using a suitable assay (e.g., ELISA), and bispecific antibodies can be purified using conventional methods. These antibodies can then be humanized according to methods described herein. Thus, the invention provides a targeting molecule which is a humanized bispecific antibody having binding specificity for CCR2 and an antigen expressed on a target cell, or a bivalent antigen-binding fragment of the bispecific antibody. The invention also relates to a method of effectuating the interaction of a CCR2-bearing cell with a target cell in a patient, comprising administering to the patient an effective amount of a targeting molecule which is a humanized bispecific antibody having binding specificity for CCR2 and an antigen expressed on a target cell, or a bivalent antigen-binding fragment of the bispecific antibody.

Method of Producing Humanized Immunoglobulins Having Specificity for CCR2

Another aspect of the invention relates to a method of preparing a humanized immunoglobulin which has binding specificity for CCR2. The humanized immunoglobulin can be obtained, for example, by the expression of one or more recombinant nucleic acids encoding a humanized immunoglobulin having binding specificity for CCR2 in a suitable host cell, for example.

Constructs or expression vectors suitable for the expression of a humanized immunoglobulin having binding specificity for CCR2 are also provided. The constructs can be introduced into a suitable host cell, and cells which express a humanized immunoglobulin of the present invention can be produced and maintained in culture. Suitable host cells can be prokaryotic, including bacterial cells such as *E. coli*, *B. subtilis* and or other suitable bacteria, or eucaryotic, such as fungal or yeast cells (e.g., *Pichia pastoris*, Aspergillus species, *Saccharomyces cerevisiae*, *Schizosaccharomyces ppombe*, *Neurospora crassa*), or other lower eucaryotic cells, and cells of higher eucaryotes such as those from insects (e.g., Sf9 insect cells (WO 94/26087, O'Connor, published Nov. 24, 1994)) or mammals (e.g., COS cells, such as COS-1 (ATCC Accession No. CRL-1650) and COS-7 (ATCC Accession No. CRL-1651), CHO (e.g., ATCC Accession No. CRL-9096), 293 (ATCC Accession No. CRL-1573), HeLa (ATCC Accession No. CCL-2), CV1 (ATCC Accession No. CCL-70), WOP (Dailey et al., *J. Virol.* 54:739–749 (1985)), 3T3, 293T (Pear et al., *Proc. Natl. Acad. Sci. U.S.A.*, 90:8392–8396 (1993)), NSO cells, SP2/0, HuT 78 cells, and the like (see, e.g., Ausubel, F. M. et al., eds. *Current Protocols in Molecular Biology*, Greene Publishing Associates and John Wiley & Sons Inc., (1993)).

Host cells which produce a humanized immunoglobulin having binding specificity for CCR2 can be produced as follows. For example, a nucleic acid encoding all or part of the coding sequence for the desired humanized immunoglobulin can be inserted into a nucleic acid vector, e.g., a DNA vector, such as a plasmid, virus or other suitable replicon for expression. A variety of vectors are available, including vectors which are maintained in single copy or multiple copy, or which become integrated into the host cell chromosome.

Suitable expression vectors can contain a number of components, including, but not limited to one or more of the following: an origin of replication; a selectable marker gene; one or more expression control elements, such as a transcriptional control element (e.g., a promoter, an enhancer, terminator), and/or one or more translation signals; a signal sequence or leader sequence for membrane targeting or secretion. In a construct, a signal sequence can be provided by the vector or other source. For example, the transcriptional and/or translational signals of an immunoglobulin can be used to direct expression.

A promoter can be provided for expression in a suitable host cell. Promoters can be constitutive or inducible. For example, a promoter can be operably linked to a nucleic acid encoding a humanized immunoglobulin or immunoglobulin chain, such that it directs expression of the encoded polypeptide. A variety of suitable promoters for procaryotic (e.g., lac, tac, T3, T7 promoters for *E. coli*) and eucaryotic (e.g., yeast alcohol dehydrogenase (ADH1), SV40, CMV) hosts are available.

In addition, the expression vectors typically comprise a selectable marker for selection of host cells carrying the vector, and, in the case of replicable expression vector, an origin or replication. Genes encoding products which confer antibiotic or drug resistance are common selectable markers and may be used in procaryotic (e.g., β-lactamase gene (ampicillin resistance), Tet gene for tetracycline resistance) and eucaryotic cells (e.g., neomycin (G418 or geneticin), gpt (mycophenolic acid), ampicillin, or hygromycin resistance genes). Dihydrofolate reductase marker genes permit selection with methotrexate in a variety of hosts. Genes encoding the gene product of auxotrophic markers of the host (e.g., LEU2, URA3, HIS3) are often used as selectable markers in yeast. Use of viral (e.g., .baculovirus) or phage vectors, and vectors which are capable of integrating into the genome of the host cell, such as retroviral vectors, are also contemplated. In one embodiment, the vector is pLKTOK38. The present invention also relates to cells carrying these expression vectors. An expression vector comprising a fused gene encoding a humanized immunoglobulin light chain, said gene comprising a nucleotide sequence encoding a CDR derived from a light chain of a nonhuman antibody having binding specificity for CCR2 and a framework region derived from a light chain of human origin.

Thus, the invention includes an expression vector comprising a gene encoding a humanized immunoglobulin light chain, said gene comprising a nucleotide sequence encoding a CDR derived from a light chain of a nonhuman antibody having binding specificity for CCR2 and a framework region derived from a light chain of human origin. The invention also relates to an expression vector comprising a gene encoding a humanized immunoglobulin heavy chain, said gene comprising a nucleotide sequence encoding a CDR derived from a heavy chain of a nonhuman antibody having binding specificity for CCR2 and a framework region derived from a heavy chain of human origin. In on embodiment, the nonhuman antibody is murine antibody 1D9. The invention also includes host cells comprising the expression vectors of the invention. The invention also relates to an isolated or recombinant gene encoding a humanized immunoglobulin light or heavy chain comprising a first nucleic acid sequence encoding an antigen binding region derived from murine monoclonal antibody 1D9; and a second nucleic acid sequence encoding at least a portion of a constant region of an immuno lobulin of human origin.

The invention also relates to a host cell (e.g., which expresses a humanized immunoglobulin or an antigen binding fragment thereof having specificity for CCR2) comprising a first recombinant nucleic acid molecule encoding a humanized immunoglobulin light chain or fragment thereof and a second recombinant nucleic acid molecule encoding a humanized immunoglobulin heavy chain or fragment thereof, wherein said first nucleic acid molecule comprises a nucleotide sequence encoding a CDR derived from the light chain of murine antibody 1D9 and a framework region derived from a light chain of human origin, and wherein said second nucleic acid molecule comprises a nucleotide sequence encoding a CDR derived from the heavy chain of murine antibody 1D9 and a framework region derived from a heavy chain of human origin. The invention also includes a method of preparing a humanized immunoglobulin or antigen-binding fragment thereof comprising maintaining a host cell of the invention under conditions appropriate for expression of a humanized immunoglobulin, whereby humanized immunoglobulin chains are expressed and a humanized immunoglobulin or antigen-binding fragment thereof having specificity for CCR2 is produced. The method can further comprise the step of isolating the humanized immunoglobulin or fragment thereof.

For example, a nucleic acid molecule (i.e., one or more nucleic acid molecules) encoding the heavy and light chains of a humanized immunoglobulin having binding specificity for CCR2, or a construct (i.e., one or more constructs) comprising such nucleic acid molecule(s), can be introduced into a suitable host cell by a method appropriate to the host cell selected (e.g., transformation, transfection, electroporation, infection), such that the nucleic acid molecule(s) are operably linked to one or more expression control elements (e.g., in a vector, in a construct created by processes in the cell, integrated into the host cell genome). Host cells can be maintained under conditions suitable for expression (e.g., in the presence of inducer, suitable media supplemented with appropriate salts, growth factors, antibiotic, nutritional supplements, etc.), whereby the encoded polypeptide(s) are produced. If desired, the encoded protein (e.g., humanized 1D9 antibody) can be isolated from, e.g., the host cells, medium, milk. This process encompasses expression in a host cell of a transgenic animal (see e.g., WO 92/03918, GenPharm International, published Mar. 19, 1992).

Fusion proteins can be produced in which a humanized immunoglobulin or immunoglobulin chain is linked to a non-immunoglobulin moiety (i.e., a moiety which does not occur in immunoglobulins as found in nature) in an N-terminal location, C-terminal location or internal to the fusion protein. For example, some embodiments can be produced by the insertion of a nucleic acid encoding immunoglobulin sequences into a suitable expression vector, such as a pET vector (e.g., pET-15b, Novagen), a phage vector (e.g., pCANTAB 5 E, Pharmacia), or other vector (e.g., pRIT2T Protein A fusion vector, Pharnacia). The resulting construct can be introduced into a suitable host cell for expression. Upon expression, some fusion proteins can be isolated or purified from a cell lysate by means of a suitable affinity matrix (see e.g., *Current Protocols in Molecular Biology* (Ausubel, F. M. et al., eds., Vol. 2, Suppl. 26, pp. 16.4.1–16.7.8 (1991)).

Therapeutic Methods and Compositions

The present invention provides humanized immunoglobulins which (1) can bind CCR2 in vitro and/or in vivo; and/or (2) can modulate an activity or function of CCR2, such as (a) binding function (e.g., the ability of CCR2 to bind to a ligand) and/or (b) leukocyte trafficking, including recruitment and/or accumulation of leukocytes in tissues. Preferably the humanized immunoglobulins are capable of selectively binding CCR2 in vitro and/or in vivo, and inhibiting CCR2-mediated interactions. In one embodiment, a humanized immunoglobulin can bind CCR2, and can inhibit binding of CCR2 to one or more of its ligands (e.g., HIV, MCP-1, MCP-2, MCP-3, MCP-4).

The humanized immunoglobulins of the present invention are useful in a variety of processes with applications in research, diagnosis and therapy. For instance, they can be used to detect, isolate, and/or purify CCR2 or variants thereof (e.g., by affinity purification or other suitable methods), and to study CCR2 structure (e.g., conformation) and function. The humanized immunoglobulins of the present invention can also be used in diagnostic applications (e.g., in vitro, ex vivo) or to modulate CCR2 function in therapeutic (including prophylactic) applications.

For example, the humanized immunoglobulins of the present invention can be used to detect and/or measure the level of CCR2 in a sample (e.g., tissues or body fluids, such as an inflammatory exudate, blood, serum, bowel fluid, on cells bearing CCR2). For example, a sample (e.g., tissue and/or body fluid) can be obtained from an individual and a suitable immunological method can be used to detect and/or measure CCR2 expression, including methods such as enzyme-linked immunosorbent assays (ELISA), including chemiluminescence assays, radioimmunoassay, and immunohistology. In one embodiment, a method of detecting a selected CCR2 in a sample is provided, comprising contacting a sample with a humanized immunoglobulin of the present invention under conditions suitable for specific binding of the humanized immunoglobulin to CCR2 and detecting antibody-CCR2 complexes which are formed. In an application of the method, humanized immunoglobulins can be used to analyze normal versus inflamed tissues (e.g., from a human) for CCR2 reactivity and/or expression (e.g., immunohistologically)), to detect associations between particular conditions and increased expression of CCR2 (e.g., in affected tissues). The humanized immunoglobulins of the present invention permit immunological methods of assessment of the presence of CCR2 in normal versus inflamed tissues, through which the presence of disease, disease progress and/or the efficacy of anti-CCR2 integrin therapy in inflammatory disease can be assessed.

The humanized immnunoglobulins of the present invention can also be used to modulate (e.g., inhibit (reduce or prevent)) binding function and/or leukocyte (e.g., lymphocyte, monocyte) trafficking modulated by CCR2. For example, humanized immunoglobulins which inhibit the binding of CCR2 to a ligand (i.e., one or more ligands) can be administered according to the method in the treatment of diseases associated with leukocyte (e.g., lymphocyte, monocyte) infiltration of tissues. Additionally, humanized immunoglobulins which inhibit the binding of CCR2 to a ligand (i.e., one or more ligands) can be administered according to the method in the treatment of HIV. An effective amount of a humanized immunoglobulin of the present invention (i.e., one or more) is administered to an individual (e.g., a mammal, such as a human or other primate) in order to treat such a disease.

The humanized immunoglobulin is administered in an effective amount which inhibits binding of CCR2 to a ligand thereof. For therapy, an effective amount will be sufficient to achieve the desired therapeutic (including prophylactic) effect (such as an amount sufficient to reduce or prevent CCR2-mediated binding and/or signalling). The humanized immunoglobulin can be administered in a single dose or multiple doses. The dosage can be determined by methods known in the art and can be dependent, for example, upon the individual's age, sensitivity, tolerance and overall well-being. Suitable dosages for antibodies can be from about 0.1 mg/kg body weight to about 10.0 mg/kg body weight per treatment.

According to the method, the humanized immunoglobulin can be administered to an individual (e.g., a human) alone or in conjunction with another agent. A humanized immunoglobulin can be administered before, along with or subsequent to administration of the additional agent. Thus, the invention includes pharmaceutical compositions comprising a humanized immunoglobulin or antigen-binding fragment thereof of the invention and a suitable carrier. In one embodiment, more than one humanized immunoglobulin which inhibits the binding of CCR2 to its ligands is administered. In another embodiment an additional monoclonal antibody is administered in addition to a humanized immunoglobulin of the present invention. In yet another embodiment, an additional pharmacologically active ingredient (e.g., an antiinflammatory compound, such as sulfasalazine, another non-steroidal antiinflammatory compound, or a steroidal antiinflammatory compound) can be administered in conjunction with a humanized immunoglobulin of the present invention.

A variety of routes of administration are possible, including, but not necessarily limited to, parenteral (e.g., intravenous, intraarterial, intramuscular, subcutaneous injection), oral (e.g., dietary), topical, inhalation (e.g., intrabronchial, intranasal or oral inhalation, intranasal drops), or rectal, depending on the disease or condition to be treated. Parenteral administration is a preferred mode of administration.

Formulation will vary according to the route of administration selected (e.g., solution, emulsion). An appropriate composition comprising the humanized antibody to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See, generally, *Remington's Pharmaceutical Sciences*, 17th Edition, Mack Publishing Co., Pa., 1985). For inhalation, the compound can be solubilized and loaded into a suitable dispenser for administration. (e.g., an atomizer, nebulizer or pressurized aerosol dispenser).

Thus, the invention includes a method of inhibiting HIV infection of a cell, comprising contacting a cell with an effective amount of a composition comprising a humanized immunoglobulin or antigen-binding fragment thereof of the invention. The invention also relates to a method of treating HIV or inhibiting HIV infection in a patient comprising administering to the patient a composition comprising an effective amount of a humanized immunoglobulin of or antigen-binding fragment thereof of the invention.

The invention also relates to a method of inhibiting a function associated with binding of a chemokine to mammalian CCR2 or a functional portion of CCR2, comprising contacting a composition comprising CCR2 or portion thereof with an effective amount of a humanized immunoglobulin or antigen-binding fragment thereof of the invention, wherein said humanized immunoglobulin inhibits binding of the chemokine to mammalian CCR2 and inhibits one or more functions associated with binding of the chemokine to CCR2. For example, the chemokine can be selected from the group consisting of MCP-1, MCP-2, MCP-3, MCP-4 and combinations thereof.

The invention also relates to a method of inhibiting leukocyte trafficking in a patient, comprising administering to the patient a composition comprising an effective amount of a humanized immunoglobulin or antigen-binding fragment thereof of the invention which binds to mammalian CCR2 and inhibits binding of a ligand to the receptor. For example, the ligand can be a chemokine (e.g., MCP-1, MCP-2, MCP-3, MCP-4) or HIV.

The invention also relates to a method of inhibiting the interaction of a first cell expressing CCR2 with a ligand (e.g., on a second cell expressing a ligand of CCR2), comprising contacting the first cell with an effective amount of a humanized immunoglobulin or antigen-binding fragment thereof of the invention, particularly wherein said immunoglobulin or fragment inhibits the binding of ligand to CCR2. For example, the cell can be selected from the group consisting of lymphocytes, monocytes, granulocytes, T cells, basophils, and cells comprising a recombinant nucleic acid encoding CCR2 or a portion thereof. In one embodiment, the ligand is a chemokine (e.g., MCP-1, MCP-2, MCP-3, MCP-4). In another embodiment, the ligand is HIV.

The invention also includes a method of treating a CCR2-mediated disorder in a patient, comprising administering to the patient an effective amount of a humanized immunoglobulin or antigen-binding fragment thereof of the invention which binds to mammalian CCR2. The disorder can include, but is not limited to, allergy, atherogenesis, anaphylaxis, malignancy, chronic and acute inflammatory disorders, histamine and IgE-mediated allergic reactions, shock, and rheumatoid arthritis, atherosclerosis, multiple sclerosis, stenosis, restenosis, allograft rejection, fibrotic disease, asthma, and inflammatory glomerulopathies.

In a particular embodiment, the invention relates to a method of inhibiting restenosis in a patient, comprising administering to the patient an effective amount of a humanized immunoglobulin or antigen-binding fragment thereof of the invention which binds to mammalian CCR2. The invention also includes a humanized immunoglobulin or antigen-binding fragment thereof of the invention for use in therapy or diagnosis or for use in treating a CCR2-mediated disease or disorder. The invention also includes the use of a humanized immunoglobulin or antigen-binding fragment thereof of the invention for the manufacture of a medicament for treating a CCR2-mediated disease.

Anti-idiotypic antibodies are also provided. Anti-idiotypic antibodies recognize antigenic determinants associated with the antigen-binding site of another antibody. Anti-idiotypic antibodies can be prepared against second antibody by immunizing an animal of the same species, and preferably of the same strain, as the animal used to produce the second antibody. See e.g., U.S. Pat. No. 4,699,880.

The present invention also pertains to the hybridoma cell lines deposited under ATCC Accession Nos. HB-12549 and HB-12550, as well as to the monoclonal antibodies produced by the hybridoma cell lines deposited under ATCC Accession Nos. HB-12549 and HB-12550. The cell lines of the present invention have uses other than for the production of the monoclonal antibodies. For example, the cell lines of the present invention can be fused with other cells (such as suitably drug-marked human myeloma, mouse myeloma, human-mouse heteromyeloma or human lymphoblastoid cells) to produce additional hybridomas, and thus provide for the transfer of the genes encoding the monoclonal antibodies. In addition, the cell lines can be used as a source of nucleic acids encoding the anti-CCR2 immunoglobulin chains, which can be isolated and expressed (e.g., upon transfer to other cells using any suitable technique (see e.g., Cabilly et al., U.S. Pat. No. 4,816,567; Winter, U.S. Pat. No. 5,225,539)). For instance, clones comprising a rearranged anti-CCR2 light or heavy chain can be isolated (e.g., by PCR) or cDNA libraries can be prepared from mRNA isolated from the cell lines, and cDNA clones encoding an anti-CCR2 immunoglobulin chain can be isolated. Thus, nucleic acids encoding the heavy and/or light chains of the antibodies or portions thereof can be obtained and used in accordance with recombinant DNA techniques for the production of the specific immunoglobulin, immunoglobulin chain, or variants thereof (e.g., humanized immunoglobulins) in a variety of host cells or in an ini vitro translation system. For example, the nucleic acids, including cDNAs, or derivatives thereof encoding variants such as a humanized immunoglobulin or immunoglobulin chain, can be placed into suitable prokaryotic or eukaryotic vectors (e.g., expression vectors) and introduced into a suitable host cell by an appropriate method (e.g., transformation, transfection, electroporation, infection), such that the nucleic acid is operably linked to one or more expression control elements (e.g., in the vector or integrated into the host cell genome). For production, host cells can be maintained under conditions suitable for expression (e.g., in the presence of inducer, suitable media supplemented with appropriate salts, growth factors, antibiotic, nutritional supplements, etc.), whereby the encoded polypeptide is produced. If desired, the encoded protein can be recovered and/or isolated (e.g., from the host cells, medium, milk). It will be appreciated that the method of production encompasses expression in a host cell of a transgenic animal (see e.g., WO 92/03918, GenPharm International, published Mar. 19, 1992).

As described herein, antibodies and functional fragments thereof of the present invention can block (inhibit) binding of a ligand to CCR2 and/or inhibit function associated with binding of the ligand to the CCP2. As discussed below various methods can be used to assess inhibition of binding of a ligand to CCR2 and/or function associated with binding of the ligand to the receptor.

Binding Assays

As used herein "mammalian CCR2 protein" refers to naturally occurring or endogenous mammalian CCR2 proteins and to proteins having an amino acid sequence which is the same as that of a naturally occurring or endogenous corresponding mammalian CCR2 protein (e.g., recombinant proteins). Accordingly, as defined herein, the term includes mature receptor protein, polymorphic or allelic variants, and other isoforms of a mammalian CCR2 (e.g., produced by alternative splicing or other cellular processes), and modified or unmodified forms of the foregoing (e.g., glycosylated, unglycosylated). Mammalian CCR2 proteins can be isolated and/or recombinant proteins (including synthetically produced proteins). Naturally occurring or endogenous mammalian CCR2 proteins include wild type proteins such as mature CCR2, polymorphic or allelic variants and other isoforms which occur naturally in mammals (e.g., humans, non-human primates), such as the CCR2a and CCR2b forms of the receptor protein which are produced by alternative splicing of the carboxy-terminus of the protein. Such proteins can be recovered or isolated from a source which naturally produces mammalian CCR2, for example. These proteins and mammalian CCR2 proteins having the same amino acid sequence as a naturally occurring or endogenous corresponding mammalian CCR2, are referred to by the name of the corresponding mamunal. For example, where the corresponding mammal is a human, the protein is designated as a human CCR2 protein (e.g., a recombinant human CCR2 produced in a suitable host cell).

"Functional variants" of mammalian CCR2 proteins include functional fragments, functional mutant proteins, and/or functional fusion proteins (e.g., produced via mutagenesis and/or recombinant techniques). Generally, fragments or portions of mammalian CCR2 proteins include those having a deletion (i.e., one or more deletions) of an amino acid (i.e., one or more amino acids) relative to the mature mammalian CCR2 protein (such as N-terminal, C-terminal or internal deletions). Fragments or portions in which only contiguous amino acids have been deleted or in which non-contiguous amino acids have been deleted relative to mature mammalian CCR2 protein are also envisioned.

Generally, mutants of mammalian CCR2 proteins include natural or artificial variants of a mammalian CCR2 protein differing by the addition, deletion and/or substitution of one or more contiguous or non-contiguous amino acid residues (e.g., receptor chimeras). Such mutations can be in a conserved region or nonconserved region (compared to other CXC and/or CC chemokine receptors), extracellular, cytoplasmic, or transmembrane region, for example.

Generally, fusion proteins encompass polypeptides comprising a mammalian CCR2 (e.g., human CCR2) as a first moiety, linked via a peptide cond to a second moiety not occurring in the mammalian CCR2 as found in nature. Thus, the second moiety can be an amino acid, oligopeptide or polypeptide. The first moiety can be in an N-terminal location, C-terminal location or internal to the fusion protein. In one embodiment, the fusion protein comprises an affinity ligand (e.g., an enzyme, an antigen, epitope tage) as the first moiety, and a second moiety comprising a linker sequence and human CCR2 or a portion thereof.

A "functional fragment or portion", "functional mutant" and/or "functional fusion protein" of a mammalian CCR2 protein refers to an isolated and/or recombinant protein or polypeptide which has at least one function characteristic of a mammalian CCR2 protein as described herein, such as a binding activity, a signaling activity and/or ability to stimulate a cellular response. Preferred functional variants can bind a ligand (i.e., one or more ligands such as MCP-1, MCP-2, MCP-3 and/or MCP-4), and are referred to herein as "ligand binding variants".

In one embodiment, a functional variant of mammalian CCR2 shares at least about 85% sequence identity with said mammalian CCR2, preferably at least about 90% sequence identity, and more preferably at least about 95% sequence identity with said mammalian CCR2. The nucleic acid and amino acid sequences of human CCR2a and CCR2b are described in U.S. Pat. No. 5,707,815. Sequence identity can be determine using a suitable program, such as the Blastx program (Version 1.4), using appropriate parameters, such as default parameters. In one embodiment, parameters for Blastx search are scoring matrix BLOSUM62, W=3. In another embodiment, a functional variant comprises a nucleic acid sequence which is different from the naturally-occurring nucleic acid molecule but which, due to the degeneracy of the genetic code, encodes mammalian CCR2 or a portion thereof A composition comprising an isolated and/or recombinant mammalian CCR2 or functional variant thereof can be maintained under conditions suitable for binding, the mammalian CCR2 or variant is contacted with an antibody or fragment to be tested, and binding is detected or measured directly or indirectly. In one embodiment, cells which naturally express CCR2 or cells comprising a recombinant nucleic acid sequence which encodes a mammalian CCR2 or variant thereof are used. The cells are maintained under conditions appropriate for expression of receptor. The cells are contacted with an antibody or fragment under conditions suitable for binding (e.g., in a suitable binding buffer), and binding is detected by standard techniques. To determine binding, the extent of binding can be determined relative to a suitable control (e.g., compared with background determined in the absence of antibody, compared with binding of a second antibody (i.e., a standard), compared with binding of antibody to untransfected cells). A cellular fraction, such as a membrane fraction, containing receptor or liposomes comprising receptor can be used in lieu of whole cells.

In one embodiment, the antibody is labeled with a suitable label (e.g., fluorescent label, isotope label, antigen or epitope label, enzyme label), and binding is determined by detection of the label. In another embodiment, bound antibody can be detected by labeled second antibody. Specificity of binding can be assessed by competition or displacement, for example, using unlabeled antibody or a ligand as competitor.

Binding inhibition assays can also be used to identify antibodies or fragments thereof which bind CCR2 and inhibit binding of another compound such as a ligand (e.g., MCP-1, MCP-2, MCP-3 and/or MCP-4) to CCR2 or a functional variant. For example, a binding assay can be conducted in which a reduction in the binding of a ligand of CCR2 (in the presence of an antibody), as compared to binding of the ligand in the absence of the antibody, is detected or measured. A composition comprising an isolated and/or recombinant mammalian CCR2 or functional variant thereof can be contacted with the ligand and antibody simultaneously, or one after the other, in either order. A reduction in the extent of binding of the ligand in the presence of the antibody, is indicative of inhibition of binding by the antibody. For example, binding of the ligand could be decreased or abolished.

In one embodiment, direct inhibition of the binding of a ligand (e.g., a chemokine such as MCP-1) to a mammalian CCR2 or variant thereof by an antibody or fragment is monitored. For example, the ability of an antibody to inhibit the binding of $^{125}$I-labeled MCP-1, $^{125}$I-labeled MCP-2, $^{125}$I-labeled MCP-3 or $^{125}$I-labeled MCP-4 to mammalian CCR2 can be monitored. Such an assay can be conducted using suitable cells bearing CCR2 or a functional variant thereof, such as isolated blood cells (e.g., T cells, PBMC) or a suitable cell line naturally expressing CCR2, or a cell line containing nucleic acid encoding a mammalian CCR2, or a membrane fraction from said cells, for instance.

Other methods of identifying the presence of an antibody which binds CCR2 are available, such as other suitable binding assays, or methods which monitor events which are triggered by receptor binding, including signaling function and/or stimulation of a cellular response (e.g., leukocyte trafficking).

It will be understood that the inhibitory effect of antibodies of the present invention can be assessed in a binding inhibition assay. Competition between antibodies for receptor binding can also be assessed in the method. Antibodies which are identified in this manner can be further assessed to determine whether, subsequent to binding, they act to inhibit other functions of CCR2 and/or to assess their therapeutic utility.

Signaling Assays

The binding of a ligand or promoter, such as an agonist, to CCR2 can result in signaling by this G protein-coupled receptor, and the activity of G proteins as well as other intracellular signaling molecules is stimulated. The induction of signaling function by a compound (e.g., an antibody or fragment thereof) can be monitored using any suitable method. Such an assay can be used to identify antibody agonists of CCR2. The inhibitory activity of an antibody or functional fragment thereof can be determined using a ligand or promoter in the assay, and assessing the ability of the antibody to inhibit the activity induced by ligand or promoter.

G protein activity, such as hydrolysis of GTP to GDP, or later signaling events triggered by receptor binding, such as induction of rapid and transient increase in the concentration of intracellular (cytosolic) free calcium [$Ca^{2+}$]i, can be assayed by methods known in the art or other suitable methods (see e.g., Neote, K. et al., *Cell*, 72: 415–425 1993); Van Riper et al., *J. Exp. Med.*, 177: 851–856 (1993); Dahinden, C. A. et al., *J. Exp. Med.*, 179: 751–756 (1994)).

For example, the functional assay of Sledziewski et al. using hybrid G protein coupled receptors can be used to monitor the ability a ligand or promoter to bind receptor and activate a G protein (Sledziewski et al., U.S. Pat. No. 5,284,746, the teachings of which are incorporated herein by reference).

Such assays can be performed in the presence of the antibody or fragment thereof to be assessed, and the ability of the antibody or fragment to inhibit the activity induced by the ligand or promoter is determined using known methods and/or methods described herein.

Chemotaxis and Assays of Cellular Stimulation

Chemotaxis assays can also be used to assess the ability of an antibody or functional fragment thereof to block binding of a ligand to mammalian CCR2 or functional variant thereof and/or inhibit function associated with binding of the ligand to the receptor. These assays are based on the functional migration of cells in vitro or in vivo induced by a compound. Chemotaxis can be assessed as described in the Examples, e.g., in an assay utilizing a 96-well chemotaxis plate, or using other art-recognized methods for assessing chemotaxis. For example, the use of an in vitro transendothelial chemotaxis assay is described by Springer et al. (Springer et al., WO 94/20142, published Sep. 15, 1994, the teachings of which are incorporated herein by reference; see also Berman et al., *Immunol. Invest.* 17: 625–677 (1988)). Migration across endothelium into collagen gels has also been described (Kavanaugh et al., *J. Immunol.*, 146: 4149–4156 (1991)). Stable transfectants of mouse L1-2 pre-B cells or of other suitable host cells capable of chemotaxis can be used in chemotaxis assays, for example.

Generally, chemotaxis assays monitor the directional movement or migration of a suitable cell (such as a leukocyte (e.g., lymphocyte, eosinophil, basophil)) into or through a barrier (e.g., endothelium, a filter), toward increased levels of a compound, from a first surface of the barrier toward an opposite second surface. Membranes or filters provide convenient barriers, such that the directional movement or migration of a suitable cell into or through a filter, toward increased levels of a compound, from a first surface of the filter toward an opposite second surface of the filter, is monitored. In some assays, the membrane is coated with a substance to facilitate adhesion, such as ICAM-1, fibronectin or collagen. Such assays provide an in vitro approximation of leukocyte "homing".

For example, one can detect or measure inhibition of the migration of cells in a suitable container (a containing means), from a first chamber into or through a microporous membrane into a second chamber which contains an antibody to be tested, and which is divided from the first chamber by the membrane. A suitable membrane, having a suitable pore size for monitoring specific migration in response to compound, including, for example, nitrocellulose, polycarbonate, is selected. For example, pore sizes of about 3–8 microns, and preferably about 5–8 microns can be used. Pore size can be uniform on a filter or within a range of suitable pore sizes.

To assess migration and inhibition of migration, the distance of migration into the filter, the number of cells crossing the filter that remain adherent to the second surface of the filter, and/or the number of cells that accumulate in the second chamber can be determined using standard techniques (e.g., microscopy). In one embodiment, the cells are labeled with a detectable label (e.g., radioisotope, fluorescent label, antigen or epitope label), and migration can be assessed in the presence and absence of the antibody or fragment by determining the presence of the label adherent to the membrane and/or present in the second chamber using an appropriate method (e.g., by detecting radioactivity, fluorescence, immunoassay). The extent of migration induced by an antibody agonist can be determined relative to a suitable control (e.g., compared to background migration determined in the absence of the antibody, compared to the extent of migration induced by a second compound (i.e., a standard), compared with migration of untransfected cells induced by the antibody).

In one embodiment, particularly for T cells, monocytes or cells expressing a mammalian CCR2, transendothelial migration can be monitored. In this embodiment, transmigration through an endothelial cell layer is assessed. To prepare the cell layer, endothelial cells can be cultured on a microporous filter or membrane, optionally coated with a substance such as collagen, fibronectin, or other extracellular matrix proteins, to facilitate the attachment of endothelial cells. Preferably, endothelial cells are cultured until a confluent monolayer is formed. A variety of mammalian endothelial cells can are available for monolayer formation, including for example, vein, artery or microvascular endothelium, such as human umbilical vein endothelial cells (Clonetics Corp, San Diego, Calif.). To assay chemotaxis in response to a particular mammalian receptor, endothelial cells of the same mammal are preferred; however endothelial cells from a heterologous mammalian species or genus can also be used.

Generally, the assay is performed by detecting the directional migration of cells into or through a membrane or filter, in a direction toward increased levels of a compound, from a first surface of the filter toward an opposite second surface of the filter, wherein the filter contains an endothelial cell layer on a first surface. Directional migration occurs from the area adjacent to the first surface, into or through the membrane, towards a compound situated on the opposite side of the filter. The concentration of compound present in the area adjacent to the second surface, is greater than that in the area adjacent to the first surface.

In one embodiment used to test for an antibody inhibitor, a composition comprising cells capable of migration and expressing a mammalian CCR2 receptor can be placed in the first chamber. A composition comprising one or more ligands or promoters capable of inducing chemotaxis of the cells in the first chamber (having chemoattractant function) is placed in the second chamber. Preferably shortly before the cells are placed in the first chamber, or simultaneously with the cells, a composition comprising the antibody to be tested is placed, preferably, in the first chamber. Antibodies or functional fragments thereof which can bind receptor and inhibit the induction of chemotaxis, by a ligand or promoter, of the cells expressing a mammalian CCR2 in this assay are inhibitors of receptor function (e.g., inhibitors of stimulatory function). A reduction in the extent of migration induced by the ligand or promoter in the presence of the antibody or fragment is indicative of inhibitory activity. Separate binding studies (see above) could be performed to determine whether inhibition is a result of binding of the antibody to receptor or occurs via a different mechanism.

In vivo assays which monitor leukocyte infiltration of a tissue, in response to injection of a compound (e.g., chemokine or antibody) in the tissue, are described below (see Models of Inflammation). These models of in vivo homing measure the ability of cells to respond to a ligand or promoter by emigration and chemotaxis to a site of inflammation and to assess the ability of an antibody or fragment thereof to block this emigration.

In addition to the methods described, the effects of an antibody or fragment on the stimulatory function of CCR2 can be assessed by monitoring cellular responses induced by active receptor, using suitable host cells containing receptor.

Identification of Additional Ligands, Inhibitors and/or Promoters of Mammalian CCR2 Function The assays described above, which can be used to assess binding and function of the antibodies and fragments of the present invention, can be adapted to identify additional ligands or other substances which bind a mammalian CCR2 or functional variant thereof, as well as inhibitors and/or promoters of mammalian CCR2 function. For example, agents having the same or a similar binding specificity as that of an antibody of the present invention or functional portion thereof can be identified by a competition assay with said antibody or portion thereof. Thus, the present invention also encompasses methods of identifying ligands of the receptor or other substances which bind a mammalian CCR2 protein, as well as inhibitors (e.g., antagonists) or promoters (e.g., agonists) of receptor function. In one embodiment, cells bearing a mammalian CCR2 protein or functional variant thereof (e.g., leukocytes, cell lines or suitable host cells which have been engineered to express a mammalian CCR2 protein or functional variant encoded by a nucleic acid introduced into said cells) are used in an assay to identify and assess the efficacy of ligands or other substances which bind receptor, including inhibitors or promoters of receptor function. Such cells are also useful in assessing the function of the expressed receptor protein or polypeptide.

According to the present invention, ligands and other substances which bind receptor, inhibitors and promoters of receptor function can be identified in a suitable assay, and further assessed for therapeutic effect. Inhibitors of receptor function can be used to inhibit (reduce or prevent) receptor activity, and ligands and/or promoters can be used to induce (trigger or enhance) normal receptor function where indicated. Thus, the present invention provides a method of treating inflammatory diseases, including autoimmune disease and graft rejection, comprising administering an inhibitor of receptor function to an individual (e.g., a mammal). The present invention further provides a method of stimulating receptor function by administering a novel ligand or promoter of receptor function to an individual, providing a new approach to selective stimulation of leukocyte function, which is useful, for example, in the treatment of infectious diseases and cancer.

As used herein, a "ligand" of a mammalian CCR2 protein refers to a particular class of substances which bind to a mammalian CCR2 protein, including natural ligands and synthetic and/or recombinant forms of natural ligands. Infectious agents having a tropism for mammalian CCR2-positive cells (e.g., viruses such as HIV) can also bind to a mammalian CCR2 protein. A natural ligand of a selected mammalian receptor is of a mammalian origin which is the same as that of the mammalian CCR2 protein (e.g., a chemokine such as MCP-1, MCP-2, MCP-3 and/or MCP-4). In a preferred embodiment, ligand binding of a mammalian CCR2 protein occurs with high affinity.

As used herein, an "inhibitor" is a substance which inhibits (decreases or prevents) at least one function characteristic of a mammalian CCR2 protein (e.g., a human CCR2), such as a binding activity (e.g., ligand binding, promoter binding, antibody binding), a signaling activity (e.g., activation of a mammalian G protein, induction of rapid and transient increase in the concentration of cytosolic free calcium [$Ca^{2+}$]i), and/or cellular response function (e.g., stimulation of chemotaxis, exocytosis or inflammatory mediator release by leukocytes). An inhibitor is also a substance which inhibits HIV entry into a cell. The term inhibitor refers to substances including antagonists which bind receptor (e.g., an antibody, a mutant of a natural ligand, small molecular weight organic molecules, other competitive inhibitors of ligand binding), and substances which inhibit receptor function without binding thereto (e.g., an anti-idiotypic antibody).

As used herein, a "promoter" is a substance which promotes (induces, causes, enhances or increases) at least one function characteristic of a mammalian CCR2 protein (e.g., a human CCR2), such as a binding activity (e.g., ligand, inhibitor and/or promoter binding), a signaling activity (e.g., activation of a mammalian G protein, induction of rapid and transient increase in the concentration of cytosolic free calcium [$Ca^{2+}$]i), and/or a cellular response function (e.g., stimulation of chemotaxis, exocytosis or inflammatory mediator release by leukocytes). The term promoter refers to substances including agonists which bind receptor (e.g., an antibody, a homolog of a natural ligand from another species), and substances which promote receptor function without binding thereto (e.g., by activating an associated protein). In a preferred embodiment, the agonist is other than a homolog of a natural ligand.

Thus, the invention also relates to a method of detecting or identifying an agent which binds a mammalian CC-chemokine receptor 2 or ligand binding variant thereof, including ligands, inhibitors, promoters, and other substances which bind a mammalian CCR2 receptor or functional variant. According to the method, an agent to be tested, an antibody or antigen-binding fragment of the present invention (e.g., 8G2, 1D9, an antibody having an epitopic specificity which is the same as or similar to that of 8G2 or 1D9, and antigen-binding fragments thereof) and a composition comprising a mammalian CC-chemokine receptor 2 or a ligand binding variant thereof can be combined. The foregoing components are combined under conditions suitable for binding of the antibody or antigen-binding fragment to mammalian CC-chemokine receptor 2 or a ligand binding variant thereof, and binding of the antibody or fragment to the mammalian CC-chemokine receptor 2 or ligand binding variant is detected or measured, either directly or indirectly, according to methods described herein or other suitable methods. A decrease in the amount of complex formed relative to a suitable control (e.g., in the absence of the agent to be tested) is indicative that the agent binds said receptor or variant. The composition comprising a mammalian CC-chemokine receptor 2 or a ligand binding variant thereof can be a membrane fraction of a cell bearing recombinant chemokine receptor 2 protein or ligand binding variant thereof. The antibody or fragment thereof can be labeled with a label such as a radioisotope, spin label, antigen or epitope label, enzyme label, fluorescent group and chemiluminescent group.

In one embodiment, the invention relates to a method of detecting or identifying an agent which binds a mammalian CC-chemokine receptor 2 or a ligand binding variant thereof, comprising combining an agent to be tested, an antibody or antigen-binding fragment of the present invention (e.g., 1D9, 8G2, an antibody having an epitopic specificity which is the same as or similar to that of 1D9 or 8G2, or antigen-binding fragments thereof) and a cell bearing a mammalian CC-chemokine receptor 2 or a ligand binding variant thereof The foregoing components are combined under conditions suitable for binding of the antibody or antigen-binding fragment to the CCR2 protein or ligand binding variant thereof, and binding of the antibody or fragment to the mammalian CC-chemokine receptor 2 or variant is detected or measured, either directly or indirectly, by methods described herein and or other suitable methods. A decrease in the amount of complex formed relative to a suitable control is indicative that the agent binds the receptor or variant. The antibody or fragment thereof can be labeled with a label selected from the group consisting of a radioisotope, spin label, antigen or epitope label, enzyme label, fluorescent group and chemiluminescent group. These and similar assays can be used to detect agents, including ligands (e.g., chemokines or strains of HIV which interact with CCR2) or other substances, including inhibitors or promoters of receptor function, which can bind CCR2 and compete with the antibodies described-herein for binding to the receptor.

The assays described above can be used, alone or in combination with each other or other suitable methods, to identify ligands or other substances which bind a mammalian CCR2 protein, and inhibitors or promoters of a mammalian CCR2 protein or variant. The in vitro methods of the present invention can be adapted for high-throughput screening in which large numbers of samples are processed (e.g., a 96-well format). Cells expressing mammalian CCR2 (e.g., human CCR2) at levels suitable for high-throughput screening can be used, and thus, are particularly valuable in the identification and/or isolation of ligands or other substances which bind receptor, and inhibitors or promoters of mammalian CCR2 proteins. Expression of receptor can be monitored in a variety of ways. For instance, expression can be monitored using antibodies of the present invention which bind receptor or a portion thereof. Also, commercially available antibodies can be used to detect expression of an antigen- or epitope-tagged fusion protein comprising a receptor protein or polypeptide (e.g., FLAG tagged receptors), and cells expressing the desired level can be selected.

Nucleic acid encoding a mammalian CCR2 protein or functional variant thereof can be incorporated into an expression system to produce a receptor protein or polypeptide. An isolated and/or recombinant mammalian CCR2 protein or variant, such as a receptor expressed in cells stably or transiently transfected with a construct comprising a recombinant nucleic acid encoding a mammalian CCR2 protein or variant, or in a cell fraction containing receptor (e.g., a membrane fraction from transfected cells, liposomes incorporating receptor), can be used in tests for receptor function. The receptor can be further purified if desired. Testing of receptor function can be carried out in vitro or in vivo.

An isolated and/or recombinant mammalian CCR2 protein or functional variant thereof, such as a human CCR2, can be used in the present method, in which the effect of a compound is assessed by monitoring receptor function as described herein or using other suitable techniques. For example, stable or transient transfectants (e.g., baculovirus infected Sf9 cells, stable tranfectants of mouse L½ pre-B cells), can be used in binding assays. Stable transfectants of Jurkat cells or of other suitable cells capable of chemotaxis can be used (e.g., mouse L½ pre-B cells) in chemotaxis assays, for example.

According to the method of the present invention, compounds can be individually screened or one or more compounds can be tested simultaneously according to the methods herein. Where a mixture of compounds is tested, the compounds selected by the processes described can be separated (as appropriate) and identified by suitable methods (e.g., PCR, sequencing, chromatography, mass spectroscopy). The presence of one or more compounds (e.g., a ligand, inhibitor, promoter) in a test sample can also be determined according to these methods.

Large combinatorial libraries of compounds (e.g., organic compounds, recombinant or synthetic peptides, "peptoids", nucleic acids) produced by combinatorial chemical synthesis or other methods can be tested (see e.g., Zuckerman, R. N. et al., *J. Med. Chem.*, 37: 2678–2685 (1994) and references cited therein; see also, Ohlmeyer, M. H. J. et al., *Proc. Natl. Acad. Sci. USA* 90:10922–10926 (1993) and DeWitt, S. H. et al., *Proc. Natl. Acad. Sci. USA* 90:6909–6913 (1993), relating to tagged compounds; Rutter, W. J. et al. U.S. Pat. No. 5,010,175; Huebner, V. D. et al., U.S. Pat. No. 5,182,366; and Geysen, H. M., U.S. Pat. No. 4,833,092). Where compounds selected from a combinatorial library by the present method carry unique tags, identification of individual compounds by chromatographic methods is possible.

In one embodiment, phage display methodology is used. For example, a mammalian CCR2 protein or functional variant, an antibody or functional portion thereof of the present invention, and a phage (e.g., a phage or collection of phage such as a library) displaying a polypeptide, can be combined under conditions appropriate for binding of the antibody or portion thereof to the mammalian CCR2 protein or variant (e.g., in a suitable binding buffer). Phage which can compete with the antibody or portion thereof and bind to the mammalian CCR2 protein or variant can be detected or selected using standard techniques or other suitable methods. Bound phage can be separated from receptor using a suitable elution buffer. For example, a change in the ionic strength or pH can lead to a release of phage. Alternatively, the elution buffer can comprise a release component or components designed to disrupt binding of compounds (e.g., one or more compounds which can disrupt binding of the displayed peptide to the receptor, such as a ligand, inhibitor, and/or promoter which competitively inhibits binding). Optionally, the selection process can be repeated or another selection step can be used to further enrich for phage which bind receptor. The displayed polypeptide can be character-ized (e.g., by sequencing phage DNA). The polypeptides identified can be produced and further tested for binding, and for inhibitor or promoter function. Analogs of such peptides can be produced which will have increased stability or other desirable properties.

In one embodiment, phage expressing and displaying fusion proteins comprising a coat protein with an N-terminal peptide encoded by random sequence nucleic acids can be produced. Suitable host cells expressing a mammalian CCR2 protein or variant and an anti-CCR2 antibody or functional portion thereof, are combined with the phage, bound phage are selected, recovered and characterized. (See e.g., Doorbar, J. and G. Winter, *J. Mol. Biol.*, 244: 361 (1994) discussing a phage display procedure used with a G protein-coupled receptor).

Other sources of potential ligands or other substances which bind to, or inhibitors and/or promoters of, mammalian CCR2 proteins include, but are not limited to, variants of CCR2 ligands, including naturally occurring, synthetic or recombinant variants of MCP-1, MCP-2, MCP-3 and/or MCP-4, substances such as other chemoattractants or chemokines, variants thereof, low molecular weight organic molecules, other inhibitors and/or promoters (e.g., anti-CCR2 antibodies, antagonists, agonists), other G protein-coupled receptor ligands, inhibitors and/or promoters (e.g., antagonists or agonists), and soluble portions of a mammalian CCR2 receptor, such as a suitable receptor peptide or analog which can inhibit receptor function (see e.g., Murphy, R. B., WO 94/05695).

Models of Inflammation

In vivo models of inflammation are available which can be used to assess the effects of antibodies and fragments of the invention in vivo as therapeutic agents. For example, leukocyte infiltration upon intradermal injection of a chemokine and an antibody or fragment thereof reactive with mammalian CCR2 into a suitable animal, such as rabbit, mouse, rat, guinea pig or rhesus macaque can be monitored (see e.g., Van Damme, J. et al., *J. Exp. Med*, 176: 59–65 (1992); Zachariae, C. O. C. et al., *J. Exp. Med.* 171: 2177–2182 (1990); Jose, P. J. etal., *J. Exp. Med.* 179: 881–887 (1994)). In one embodiment, skin biopsies are assessed histologically for infiltration of leukocytes (e.g., eosinophils, granulocytes). In another embodiment, labeled cells (e.g., stably transfected cells expressing a mammalian CCR2, labeled with $^{111}$In for example) capable of chemotaxis and extravasation are administered to the animal. For example, an antibody or fragment to be assessed can be administered, either before, simultaneously with or after ligand or agonist is administered to the test animal. A decrease of the extent of infiltration in the presence of antibody as compared with the extent of infiltration in the absence of inhibitor is indicative of inhibition.

Diagnostic and Therapeutic Applications

The antibodies and fragments of the present invention are useful in a variety of applications, including research, diagnostic and therapeutic applications. In one embodiment, antibodies are labeled with a suitable label (e.g., fluorescent label, chemiluminescent label, isotope label, antigen or epitope label or enzyme label). For instance, they can be used to isolate and/or purify receptor or portions thereof, and to study receptor structure (e.g., conformation) and function.

In addition, the various antibodies of the present invention can be used to detect CCR2 or to measure the expression of receptor, for example, on T cells (e.g., CD8+ cells, CD45RO+ cells), monocytes and/or on cells transfected with a receptor gene. Thus, they also have utility in applications such as cell sorting (e.g., flow cytometry, fluorescence activated cell sorting), for diagnostic or research purposes.

The anti-CCR2 antibodies of the present invention have value in diagnostic applications. An anti-CCR2 antibody or fragment thereof can be used to monitor expression of this receptor in HIV infected individuals, similar to the way anti-CD4 has been used as a diagnostic indicator of disease stage.

Typically, diagnostic assays entail detecting the formation of a complex resulting from the binding of an antibody or fragment thereof to CCR2. For diagnostic purposes, the antibodies or antigen-binding fragments can be labeled or unlabeled. The antibodies or fragments can be directly labeled. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654 and 4,098,876). When unlabeled, the antibodies or fragments can be detected using suitable means, as in agglutination assays, for example. Unlabeled antibodies or fragments can also be used in combination with another (i.e., one or more) suitable reagent which can be used to detect antibody, such as a labeled antibody (e.g., a second antibody) reactive with the first antibody (e.g., anti-idiotype antibodies or other antibodies that are specific for the unlabeled immunoglobulin) or other suitable reagent (e.g., labeled protein A).

In one embodiment, the antibodies or fragments of the present invention can be utilized in enzyme immunoassays, wherein the subject antibody or fragment, or second antibodies, are conjugated to an enzyme. When a biological sample comprising a mammalian CCR2 protein is combined with the subject antibodies, binding occurs between the antibodies and CCR2 protein. In one embodiment, a sample containing cells expressing a mammalian CCR2 protein, such as human blood, is combined with the subject antibodies, and binding occurs between the antibodies and cells bearing a human CCR2 protein comprising an epitope recognized by the antibody. These bound cells can be separated from unbound reagents and the presence of the antibody-enzyme conjugate specifically bound to the cells can be determined, for example, by contacting the sample with a substrate of the enzyme which produces a color or other detectable change when acted on by the enzyme. In another embodiment, the subject antibodies can be unlabeled, and a second, labeled antibody can be added which recognizes the subject antibody.

Kits for use in detecting the presence of a mammalian CCR2 protein in a biological sample can also be prepared. Such kits will include an antibody or functional fragment thereof which binds to a mammalian CC-chemokine receptor 2 or portion of said receptor, as well as one or more ancillary reagents suitable for detecting the presence of a complex between the antibody or fragment and CCR2 or portion thereof. The antibody compositions of the present invention can be provided in lyophilized form, either alone or in combination with additional antibodies specific for other epitopes. The antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the antibodies can be provided as a lyophilized mixture with the adjunct ingredients, or the adjunct ingredients can be separately provided for combination by the user. Generally these adjunct materials will be present in less than about 5% weight based on the amount of active antibody, and usually will be present in a total amount of at least about 0.001% weight based on antibody concentration. Where a second antibody capable of binding to the monoclonal antibody is employed, such antibody can be provided in the kit, for instance in a separate vial or container. The second antibody, if present, is typically labeled, and can be formulated in an analogous manner with the antibody formulations described above.

Similarly, the present invention also relates to a method of detecting and/or quantitating expression of a mammalian CCR2 or a portion of the receptor by a cell, in which a composition comprising a cell or fraction thereof (e.g., membrane fraction) is contacted with an antibody or functional fragment thereof (e.g., 1D9 and/or 8G2) which binds to a mammalian CCR2 or portion of the receptor under conditions appropriate for binding of the antibody or fragment thereto, and binding is monitored. Detection of the antibody, indicative of the formation of a complex between antibody and CCR2 or a portion thereof, indicates the presence of the receptor. Binding of antibody to the cell can be determined as described above under the heading "Binding Assays", for example. The method can be used to detect expression of CCR2 on cells from an individual (e.g., in a sample, such as a body fluid, such as blood, saliva or other suitable sample). The level of expression of CCR2 on the surface of T cells or monocytes can also be determined, for instance, by flow cytometry, and the level of expression (e.g., staining intensity) can be correlated with disease susceptibility, progression or risk.

Chemokine receptors function in the migration of leukocytes throughout the body, particularly to inflammatory sites. Inflammatory cell emigration from the vasculature is regulated by a three-step process involving interactions of leukocyte and endothelial cell adhesion proteins and cell specific chemoattractants and activating factors (Springer, T. A., *Cell*, 76:301–314 (1994); Butcher, E. C., *Cell*, 67:1033–1036 (1991); Butcher, E. C. and Picker, L. J., *Science* (Wash. DC), 272:60–66 (1996)). These are: (a) a low affinity interaction between leukocyte selectins and endothelial cell carbohydrates; (b) a high-affinity interaction between leukocyte chemoattractant receptors and chemoattractant/activating factors; and (c) a tight-binding between leukocyte integrins and endothelial cell adhesion proteins of the immunoglobulin superfamily. Different leukocyte subsets express different repertoires of selectins, chemoattractant receptors and integrins. Additionally, inflammation alters the expression of endothelial adhesion proteins and the expression of chemoattractant and leukocyte activating factors. As a consequence, there is a great deal of diversity for regulating the selectivity of leukocyte recruitment to extravascular sites. The second step is crucial in that the activation of the leukocyte chemoattractant receptors is thought to cause the transition from the selectin-mediated cell rolling to the integrin-mediated tight binding. This results in the leukocyte being ready to transmigrate to perivascular sites. The chemoattractant/chemoattractant receptor interaction is also crucial for transendothelial migration and localization within a tissue (Campbell, J. J., et al., *J. Cell Biol.*, 134:255–266 (1996); Carr, M. W., et al., *Immunity*, 4:179–187 (1996)). This migration is directed by a concentration gradient of chemoattractant leading towards the inflammatory focus.

CCR2 has an important role in leukocyte trafficking. It is likely that CCR2 is a key chemokine receptor for T cell or T cell subset or monocyte migration to certain inflammatory sites, and so anti-CCR2 mAbs can be used to inhibit (reduce or prevent) T cell or monocyte migration, particularly that associated with T cell dysfunction, such as autoimmune disease, or allergic reactions or with monocyte-mediated disorders such as atherosclerosis. Accordingly, the antibodies and fragments thereof of the present invention can also be used to modulate receptor function in research and therapeutic applications. For instance, the antibodies and functional fragments described herein can act as inhibitors to inhibit (reduce or prevent) (a) binding (e.g., of a ligand, an inhibitor or a promoter) to the receptor, (b) a receptor signaling function, and/or (c) a stimulatory function. Antibodies which act as inhibitors of receptor function can block ligand or promoter binding directly or indirectly (e.g., by causing a conformational change). For example, antibodies can inhibit receptor function by inhibiting binding of a ligand, or by desensitization (with or without inhibition of binding of a ligand). Antibodies which bind receptor can also act as agonists of receptor function, triggering or stimulating a receptor function, such as a signaling and/or a stimulatory function of a receptor (e.g., leukocyte trafficking) upon binding to receptor.

Thus, the present invention provides a method of inhibiting leukocyte trafficking in a mammal (e.g., a human patient), comprising administering to the mammal an effective amount of an antibody or functional fragment of the present invention. Administration of an antibody or fragment of the present invention can result in amelioration or elimination of the disease state.

The antibody of the present invention, or a functional fragment thereof, can also be used to treat disorders in which activation of the CCR2 receptor by binding of chemokines is implicated. For example, the antibodies or functional fragments thereof (e.g., 1D9 and/or 8G2 or functional fragments thereof) can be used to treat allergy, atherogenesis, anaphylaxis, malignancy, chronic and acute inflammation, histamine and IgE-mediated allergic reactions, shock, and rheumatoid arthritis, atherosclerosis, multiple sclerosis, stenosis, restenosis, allograft rejection, fibrotic disease, asthma, and inflammatory glomerulopathies.

Diseases or conditions of humans or other species which can be treated with inhibitors of CCR2 receptor function (including antibodies or suitable fragments thereof), include, but are not limited to:

inflammatory or allergic diseases and conditions, including respiratory allergic diseases such as asthma, allergic rhinitis, hypersensitivity lung diseases, hypersensitivity pneumonitis, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); anaphylaxis or hypersensitivity responses, drug allergies (e.g., to penicillin, cephalosporins), insect sting allergies; inflammatory bowel diseases, such as Crohn's disease and ulcerative colitis; spondyloarthropathies; scleroderma; psoriasis and inflammatory dermatoses such as dernatitis, eczema, atopic dermatitis, allergic contact dermatitis, urticaria; vasculitis (e.g., necrotizing, cutaneous, and hypersensitivity vasculitis);

autoimmune diseases, such as arthritis (e.g., rheumatoid arthritis, psoriatic arthritis), multiple sclerosis, systemic lupus erythematosus, myasthenia gravis, juvenile onset diabetes, nephritides such as glomerulonephritis, autoimmune thyroiditis, Behcet's disease;

graft rejection (e.g., in transplantation), including allograft rejection or graft-versus-host disease, and organ transplant-associated arteriosclerosis;

atherosclerosis;

cancers with leukocyte infiltration of the skin or organs;

stenosis or restenosis of the vasculature, particularly of the arteries, e.g., the coronary artery, such as stenosis or restenosis which results from vascular intervention (e.g., surgical, therapeutic or mechanical intervention), as well as neointimal hyperplasia. For example, restenosis, which typically produces a narrowing of the lumenal opening of the vessel, can result from vascular injury including, but not limited to, that produced by vascular graft procedures, angioplasty, including angioplasty performed by balloon, atherectomy, laser or other suitable method (e.g., percutaneous translumenal coronary angioplasty (PTCA)), stent placement (e.g., mechanical or biological endovascular stent placement), vascular bypass procedures or combinations thereof, as well as other procedures used to treat stenotic or occluded blood vessels;

other diseases or conditions (including CCR2-mediated diseases or conditions), in which undesirable inflammatory responses are to be inhibited can be treated, including, but not limited to, reperfusion injury, certain hematologic malignancies, cytokine-induced toxicity (e.g., septic shock, endotoxic shock), polymyositis, dermatomyositis, and granulomatous diseases including sarcoidosis.

Diseases or conditions of humans or other species which can be treated with promoters of CCR2 receptor function (including antibodies or fragments thereof), include, but are not limited to:

immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; and immunosuppression due congenital deficiency in receptor function or other causes.

Anti-CCR2 antibodies of the present invention can block the binding of one or more chemokines, thereby blocking the downstream cascade of one or more events leading to the above disorders.

Antibodies and functional fragments thereof which are antagonists of CCR2 can be used as therapeutics for AIDS, as well as certain inflammatory diseases. HIV-1 and HIV-2 are the etiologic agents of acquired immunodeficiency syndrome (AIDS) in humans. AIDS results in part from the depletion of CD4+ T lymphocytes in HIV infected individuals. HIV-1 infects primarily T lymphocytes, monocytes/macrophages, dendritic cells and, in the central nervous system, microglia. All of these cells express the CD4 glycoprotein, which serves as a receptor for HIV-1 and HIV-2. Efficient entry of HIV into target cells is dependent upon binding of the viral exterior envelope glycoprotein, gp120, to the amino-terminal CD4 domain. After virus binding, the HIV-1 envelope glycoproteins mediate the fusion of viral and host cell membranes to complete the entry process. Membrane fusion directed by HIV-1 envelope glycoproteins expressed on the infected cell surface leads to cell-cell fusion, resulting in syncytia.

Recently, host cell factors in addition to CD4 have been suggested to determine the efficiency of HIV-1 envelope glycoprotein-mediated membrane fusion. The 7 transmembrane receptor (7TMR) termed HUMSTSR, LESTR, or "fusin" has been shown to allow a range of CD4-expressing cells to support infection and cell fusion mediated by laboratory-adapted HIV-1 envelope glycoproteins (Feng, Y., et al., *Science* (Wash. DC), 272:872–877 (1996)). Antibodies to HUMSTSR blocked cell fusion and infection by laboratory-adapted HIV-1 isolates but not by macrophage-tropic primary viruses in vitro (Feng, Y., et al., *Science* (Wash. DC), 272:872–877 (1996)).

The ability of chemokine receptors and related molecules to facilitate the infection of primary clinical HIV-1 isolates has been reported recently by several groups (see e.g., Bates, P., *Cell*, 86:1–3 (1996); Choe, H., et al., *Cell*, 85:1135–1148 (1996); Doranz et al., *Cell* 85:1149–1158 (1996)). These studies indicated that involvement of various members of the chemokine receptor family in the early stages of HIV-1 infection helps to explain viral tropism and β-chemokine inhibition of primary HIV-1 isolates.

The present invention also provides a method of inhibiting HIV infection of a cell (e.g., new infection and/or syncytium formation) which expresses a mammalian CCR2 or portion thereof, comprising contacting the cell with a composition comprising an effective amount of an antibody or functional fragment thereof which binds to a mammalian CCR2 or portion of said receptor. The composition can also comprise one or more additional agents effective against HIV, including, but not limited to, anti-CCR3 antibodies, anti-CCR5 antibodies, and anti-fusin antibodies.

Various methods can be used to assess binding of HIV to a cell and/or infection of a cell by HIV in the presence of the antibodies of the present invention. For example, assays which assess binding of gp120 or a portion thereof to the receptor, HIV infection and syncytium formation can be used (see, for example, Choe, H., et al., *Cell*, 85:1135–1148 (1996)). The ability of the antibody of the present invention to inhibit these processes can be assessed using these or other suitable methods.

In addition, the present invention provides a method of treating HIV in a patient, comprising administering to the patient a composition comprising an effective amount of an antibody or functional fragment thereof which binds to a mammalian CCR2 or portion of said receptor. Again, the composition can also comprise one or more additional agents effective against HIV, including, but not limited to, anti-CCR3 antibodies, anti-CCR5 antibodies, and anti-fusin antibodies. Therapeutic use of antibody to treat HIV includes prophylactic use (e.g., for treatment of a patient who may be or who may have been exposed to HIV). For example, health care providers who may be exposed or who have been exposed to HIV (e.g., by needle-stick) can be treated according to the method. Another example is the treatment of a patient exposed to virus after unprotected sexual contact or failure of protection.

In AIDS, multiple drug treatment appears the most promising. An anti-chemokine receptor antagonist that inhibits HIV infection can be added to the drug treatment regimen, in particular by blocking virus infection of new cells. Thus, administration of an antibody or fragment of the present invention in combination with one or more other therapeutic agents such as nucleoside analogues (e.g., AZT, 3TC, ddI) and/or protease inhibitors is envisioned, and provides an important addition to an HIV treatment regimen. In one embodiment, a humanized anti-CCR2 mAb is used in combination with a (i.e., one or more) therapeutic agent to reduce viral load from patients, by preventing fusion and/or infection of new cells. Such an antibody can also be useful in preventing perinatal infection.

Another aspect of the invention relates to a method of preventing HIV infection in an individual, comprising administering to the individual an effective amount of an antibody or functional fragment thereof which binds to CCR2. According to the method, preventing HIV infection includes treatment in order to prevent (reduce or eliminate) infection of new cells in an infected individual or in order to prevent infection in an individual who may be, may have been, or has been, exposed to HIV. For example, individuals such as an HIV infected individual, a fetus of an HIV infected female, or a health care worker may be treated according to the method of the present invention.

Modes of Administration

One or more antibodies or fragments of the present invention can be administered to an individual by an appropriate route, either alone or in combination with (before, simultaneous with, or after) another drug or agent, or before, simultaneous with or after surgical, mechanical or therapeutic intervention. For example, the antibodies of the present invention can also be used in combination with other monoclonal or polyclonal antibodies (e.g., in combination with antibodies which bind other chemokine receptors, including, but not limited to, CCR3 and CCR5) or with existing blood plasma products, such as commercially available gamma globulin and immune globulin products used in prophylactic or therapeutic treatments. The antibodies or fragments of the present invention can be used as separately administered compositions given in conjunction with antibiotics and/or antimicrobial agents.

An effective amount of an antibody or fragment (i.e., one or more antibodies or fragments) is administered. An effective amount is an amount sufficient to achieve the desired therapeutic (including prophylactic) effect, under the conditions of administration, such as an amount sufficient for inhibition of a CCR2 function, and thereby, inhibition of an inflammatory response or HIV infection, or an amount sufficient for promotion of a CCR2 function, as indicated.

A variety of routes of administration are possible including, but not necessarily limited to, oral, dietary, topical, parenteral (e.g., intravenous, intraarterial, intramuscular, subcutaneous injection or infusion), inhalation (e.g., intrabronchial, intraocular, intranasal or oral inhalation, intranasal drops), depending on the disease or condition to be treated. Other suitable methods of administration can also include rechargeable or biodegradable devices and slow release polymeric devices. The pharmaceutical compositions of this invention can also be administered as part of a combinatorial therapy with other agents.

Formulation of an antibody or fragment to be administered will vary according to the route of administration and formulation (e.g., solution, emulsion, capsule) selected. An appropriate pharmaceutical composition comprising an antibody or functional fragment thereof to be administered can be prepared in a physiologically acceptable vehicle or carrier. A mixture of antibodies and/or fragments can also be used. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. A variety of appropriate aqueous carriers are known to the skilled artisan, including water, buffered water, buffered saline, polyols (e.g., glycerol, propylene glycol, liquid polyethylene glycol), dextrose solution and glycine. Intravenous vehicles can include various additives, preservatives, or fluid, nutrient or electrolyte replenishers (See, generally, *Remington's Pharmaceutical*

*Science*, 16th Edition, Mack, Ed. 1980). The compositions can optionally contain pharmaceutically acceptable auxiliary substances as required to approximate physiological conditions such as pH adjusting and buffering agents and toxicity adjusting agents, for example, sodium acetate, sodium chloride, potassium chloride, calcium chloride and sodium lactate. The antibodies and fragments of this invention can be lyophilized for storage and reconstituted in a suitable carrier prior to use according to art-known lyophilization and reconstitution techniques. The optimum concentration of the active ingredient(s) in the chosen medium can be determined empirically, according to procedures well known to the skilled artisan, and will depend on the ultimate pharmaceutical formulation desired. For inhalation, the antibody or fragment can be solubilized and loaded into a suitable dispenser for administration (e.g., an atomizer, nebulizer or pressurized aerosol dispenser).

The present invention will now be illustrated by the following Examples, which are not intended to be limiting in any way. The teachings of all references cited herein are incorporated herein by reference.

EXAMPLES

Example 1

Materials

The following materials were obtained from the indicated sources:

PE-conjugated anti-CD16, PE-conjugated streptavidin, and biotinylated anti-human IgE were from Pharmingen (San Diego, Calif.). FITC-conjugated goat anti-mouse IgG was from Jackson Immunoresearch Laboratories (West Grove, Pa.). FACS Lysing Buffer was from Becton Dickenson (Mountain View, Calif.) and [$^{125}$I]-MCP-1 was from NEN (Boston, Mass.).

Cells, Cell Lines, and Tissue Culture

The murine pre-B lymphoma cell line L½ was maintained in RPMI-1640 supplemented with 10% Fetal Clone I (Gibco BRL, Gaithersburg, Md.) 50 Units/mL penicillin (Gibco BRL), 50 µg/mL streptomycin (Gibco BRL), 2 mM L-Glutamine (Gibco BRL), and 55 µM β-mercaptoethanol (Gibco BRL). Other cell lines included transfectants of L½ cells expressing either CCR1 (Campbell, J. et al. (1996) *J. Cell Bio.*, 134:255–266), CCR5 (Wu et al., *Nature* 384:179–183 (1996)) grown in the above culture medium supplemented with 800 µg/ml active G418. THP-1 cells (ATCC No. TIB202) were grown in accordance with ATCC instructions. PBMC were purified from heparinized blood as described in Ponath et al., *J. Clin. Invest.*, 97:604–612 (1996).

Preparation of CCR2b Expression Construct and Stable Transfectants

The coding region for the human CCR2b (Charo et al. (1994) *Proc. Natl. Acad. Sci. USA*, 91:2752) was obtained by RT-PCR amplification as described (Qin, S. et al. (1996) *Eur. J. Immunol.*, 26:640–647). cDNA was made using oligo(dT)-priming, and amplification of the CCR2b coding region was achieved by nested PCR with the following sets of primers which correspond to the positions of the CCR2b sequence (GenBank Accession No. U03905; Charo et al., *Proc. Natl. Acad. Sci. USA* 91:2752–2756 (1994)) as indicated:

1) 5' primer: 5'-TGAGACAAGCCACAAGCTGAAC-3' (nucleotides 11 to 32; SEQ ID NO: 1);
3' Primer: 5'-TCTGTATTAGTACACACAGCCC-3' (nucleotides 1301 to 1280; SEQ ID NO: 2);

2) 5' Primer: 5'-ATGCTGTCCACATCTCGTTCTCGG-3' (nucleotides 81 to 104; SEQ ID NO: 3);
3' Primer: 5'-TTATAAACCAGCCGAG-ACTTCCTGCTC-3' (nucleotides 1164 to 1137; SEQ ID NO: 4).

The CCR2B cDNA coding region was modified to contain the CD5 signal peptide leader sequence (Aruffo et al., *Cell* 61:1303–1313 (1990)). The predicted amino acid sequence of this peptide is:

NH$_2$-Met-Pro-Met-Gly-Ser-Leu-Gln-Pro-Leu-Ala-Thr-Leu-Tyr-Leu-Leu-Gly-Met-Leu-Val-Ala-Ser-Val-Leu-Ala. . . (SEQ ID NO: 5)

Using PCR with the CCR2b cDNA as template and two overlapping 5' primers that contain a BamH1 restriction site, encode the CD5 signal peptide sequence and the amino terminal sequence of CCR2b, and a 3' primer located internally in the CCRb coding region.

5' CD5 Seq1 primer
5'-GGGGATCCAGAAACCATGCCCATGGGGTCT-CTGCAACCGCTG GCCACCTTGTACCTGCTG-3' (SEQ ID NO: 6)

5' CD5 Seq2 primer
5'-GCCACCTTGTACCTGCTGGGGATGCTGGTC-GCTTCCGTGCTAG CGATGCTGTCCACATC-TCGTTC-3' (SEQ ID NO: 7)

3' CCR2AB2 primer-5'-GACGACCAG-CATGTTGCC-3' (SEQ ID NO: 8; U03905 nucleotides 272 to 255)

The 278 base pair amplified fragment was digested with BamHI and Apal and the resulting 209 base pair fragment was inserted at the Apal site at position 206 of the CCR2b cDNA (GenBank Accession No. U03905) to replace the endogenous 5' base pair fragment of CCR2. The resulting sequence that encodes a CCR2b with the CD5 signal peptide leader sequence immediately preceding the receptor initiator methionine was inserted into the BamHI and Xhol sites of pcDNA3 (Invitrogen, San Diego, CA) to create the mammalian expression plasmid pCD5MCPRB. The CD5-CCR2b fragment was subdloned into the BamH I-Not I site of pCDEF3 (Goldman et al., (1996) *Biotechniques* 21:1013–1015), and this construct was designated CCR2bDEF3. In this expression vector, the expression of the inserted gene is driven by the EF-1α ( promoter.

Fifty milliliters of L½ cells were seeded at 4×10$^5$ cells/mL the day before the electroporation. On the day of the electroporation, the cells, which had grown up to a density of 1×10$^6$/mL, were centrifuged out of their medium and resuspended in 800 µl room temperature electroporation buffer (Zajac et al., *DNA* 7:509–513). 120 mM L-Glutamic Acid (Sigma), 7 mM Mg Acetate (EM Science), 4.3 mM Glucose (Sigma), 17 mM K Pipes, pH 6.9 (Sigma), 1 mM EGTA (Sigma), 5 mM ATP, pH 7.0 (Sigma). Twenty-five micrograms Sca I linearized, phenol/chloroform/isoamyl alcohol extracted and isopropanol precipitated CCR2bDEF3 plasmid DNA was placed in an 0.4 cm gap electroporation curvette. The resuspended cells were added to the curvette, and a single pulse applied at 450 volts, 960 µFd. The cells were then transferred from the curvette to a T-75 flask containing 15 mL L½ growth medium (described above, and grown for three days, at which time the cells were centrifuged out of their medium and resuspended in L½ growth medium additionally supplemented with 1 mM sodium pyruvate (Gibco BRL) and 0.8 mg/mL active G418 (Gibco BRL).

Selection of Cells Expressing CCR2b by Chemotaxis

The transfected cells were allowed to grow for eleven days, at which point they were split 1:20 into fresh growth medium. On the sixteenth day, the cells were selected by chemotaxis. 600 μL 1 nM MCP-1 in RPMI 1640 supplemented with 0.5% BSA (RPMI/BSA) was placed in the lower chamber and 1×10⁶ CCR2bDEF3 cells in 100 μl of RPMI/BSA were placed in the upper chamber of a 3.0 micron pore 24-well chemotaxis plate (Becton Dickinson). The cells were allowed to chemotax for four hours and twenty minutes in a 37° C., 5% $CO_2$, humidified incubator, at which time the upper chamber was removed. This incubation time was chosen at the time of the experiment because it was sufficiently long for cells responding to the MCP-1 to chemotax, but short enough to keep the background low.

Secondary-Selection of CCR2b Expressing-Cells by FACS Sorting

The cells which had chemotaxed through the membrane and into the lower chamber were grown up, and further purified by sterile FACS sorting. Ten million CCR2bDEF3 cells were centrifuged out of their medium, resuspended in 2.5 mL PBS(+Ca, Mg) supplemented with 1% heat-inactivated Fetal Calf Serum ("HI FCS") (Gibco BRL) and 2.5 mL sterile filtered anti-CCR2b amino-terminal peptide antibody supernatant 5A11. The cells and the antibody were mixed and allowed to incubate on ice for thirty minutes. The cells were then washed twice with PBS (+) (Gibco BRL), and resuspended in 5 mL of a sterile filtered, 1:250 dilution of FITC-conjugated, affinity-purified $F(ab^1)_2$ goat anti-mouse IgG (Jackson ImmunoResearch Laboratories) in PBS (+) supplemented with 1% HI FCS. The cells were incubated for thirty minutes on ice in the dark, and then washed twice with PBS(+) (GIBCO BRL). The cells were sorted on the FACSCalibur® and the brightest 4% of cells were collected. ($FL1 \geq 3 \times 10^2$).

The sorted cells were allowed to grow up, and they were resorted using the same protocol as above. The brightest 1% of cells were collected. ($FL1 \geq 3 \times 10^3$).

Monoclonal Antibody Production

To produce mAbs to CCR2b, transfectants were continually monitored to ensure that levels of expression did not drift downward. FACS staining was performed periodically to ascertain receptor expression on the transfectants using the anti CCR2b antibody supernatant 5A11 with goat anti-mouse IgG FITC as the secondary antibody.

Twenty million CCR2bDEF3.L½ cells were washed in RPMI 1640 (Gibco BRL) and incubated in RPMI 1640 plus 0.2 mg/mL Mitomycin C for 30 minutes at 37° C. The cells were then washed twice with PBS (+) and 2×10⁷ cells in 0.5 mL PBS (+) were injected intraperitoneally into a C57 BL/6 female mouse. This was repeated two more times at two week intervals. The fourth time, 2×10⁷ cells were resuspended in 0.25 mL and injected intravenously. Three days after the intravenous injection, the mouse was sacrificed and the spleen removed and the cells fused with the SP2/0 cell line as described (*Current Protocols in Immunology*, John Wiley and Sons, New York, 1992).

This set of mice had previously been immunized many times with 2 different cell lines as well as a synthetic peptide, but no antibodies that stained CCR2 positive cells were generated from several fusions. The above four immunizations with the CCR2bDEF3.L½ cell line expressing high levels of CCR2b were critical to obtain the described antibody.

Selecting Single Cell Clone of CCR2 Transfectants by Limiting Dilution

After the mouse received the last injection, the twice sorted cells were allowed to grow up again, and then they were further purified by limiting dilution. The cells were plated at 1 and 0.5 cell per well in 96 well plates. Subcloned cells from the 0.5 cell per well dilution were grown up and tested for CCR2b expression by indirect immunofluorescent FACS analysis using the anti-CCR2b antibody supernatant 5A11 with goat anti-mouse IgG FITC as the secondary antibody. The procedure was the same as described above, except that the staining volume was 100 μl. Four positives were selected and frozen down.

Identification of Positive Monoclonal Antibodies

Immunofluorescent staining analysis using a FACScan® (Becton Dickinson & Co., Mountain View, Calif.) was used to identify the monoclonal antibodies which were reactive with the CCR2b receptor. Hybridoma culture supernatants were assayed in a 96-well format using goat anti-mouse IgG FITC as the secondary antibody. CCR2bDEF3.L½ cells were used to identify monoclonal antibodies reactive with CCR2b, and untransfected L½ cells were used to eliminate monoclonal antibodies reactive with other cell surface proteins.

FACS Staining—Cultured Cells

For the staining of cultured transfectant cell lines 0.5×10⁶ cells in 50 μl were resuspended in PBS +1% FCS in a 96 well polystyrene V-bottom plate. 50 μl of primary antibody supernatants or HT medium (negative control) were added, and the samples were incubated at 4° C. for 30 min. 100 μl of PBS were added and the cells were pelleted by centrifugation and washed once with PBS. The pellet was resuspended in 100 μl PBS +1% FCS containing FITC-conjugated goat anti-mouse IgG antibody (a 1:250 dilution) and incubated for thirty minutes at 4° C. in the dark. The cells were washed twice with PBS, resuspended in PBS, and analyzed by flow cytometry with a FacScan cytometer using the CellQuest software (Becton-Dickenson) Cells were fixed with PBS/1% formaldehyde if they were not to be analyzed the same day. Monoclonal antibodies 1D9 and 8G2 stain CCR2 transfectants but not CCR1 or CCR5 transfectants (FIG. 1).

FACS Staining—Whole Blood

100 μl whole blood was mixed with 100 μl of 1D9 antibody hybridoma supernatants or HT medium (negative control) and incubated at 4° C. for 30 min. After one wash with PBS, 100 μl FITC-conjugated goat anti-mouse IgG antibody (a 1:250 dilution) was added to each sample and incubated for 30 min. at 4° C. in the dark. Samples were then washed once with PBS if a second color staining is to be done, otherwise washed twice more in PBS. For two color staining 5 μl of mouse serum was added to the cell pellets after the single wash, mixed, and incubated for five minutes at 4° C. in the dark. Second primary antibodies (or PBS as a negative control) were added (10 μl anti-CD16, 100 μl 1:200 dilution of anti-IgE) and incubated for thirty minutes at 4° C. in the dark. Samples were then washed one time with PBS and resuspended in 100 μL streptavidin PE (1:200 PBS +1% BSA) and incubated for fifteen minutes at 4° C. in the dark. Eyrythrocytes were lysed by adding 2 ml of FACS Lysing Buffer to each sample and incubating at room temperature in the dark for fifteen minutes or until samples were clear. The cells were pelleted by centrifugation and all but 200 μl of the supernatant was aspirated. The samples were analyzed by flow cytometry on a FacScan cytometer using the CellQuest software (Becton-Dickenson). CCR2b is expressed on most monocytes, a subpopulation of lymphocytes and a subset of granulocytes (FIGS. 2A-2L). CCR2b is expressed on an IgE-positive population in peripheral blood (basophils)(FIGS. 3A-3I).

MCP-1 Binding Assays

Figure 4:
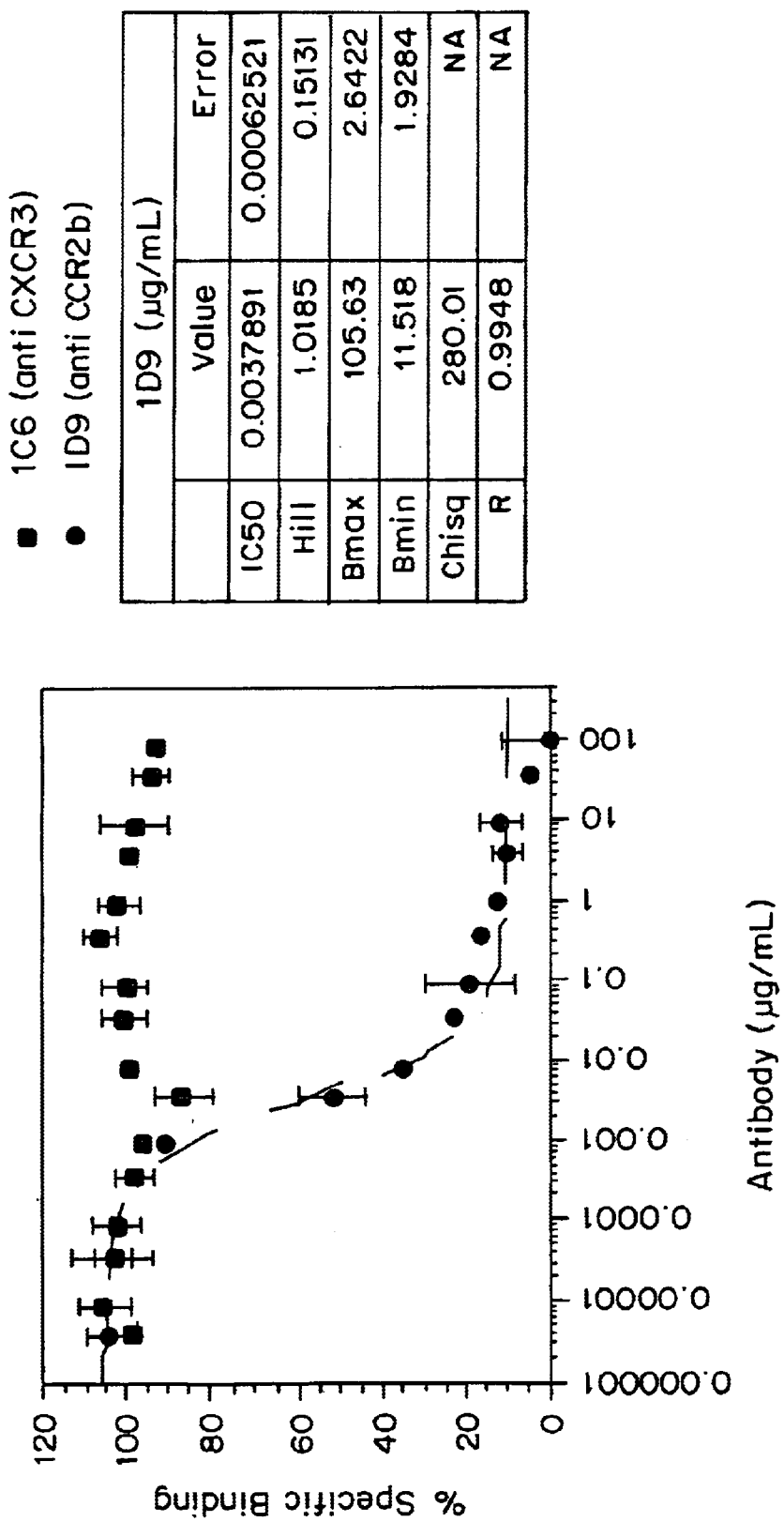
FIG. 4 illustrates that mAb 1D9 inhibits [$^{125}$I]MCP-1 binding to THP-1 cell membranes. 3.0 μg of THP-1 membrane protein was incubated with 0.1 nM [$^{125}$I]MCP-1 in the presence of various concentrations of 1D9 or the isotype-matched anti-CXCR3 antibody 1C6. The amount of bound tracer was determined by separation of free from bound by filtration and scintillation counting. The data was analyzed to determine the $IC_{50}$ value by non-linear regression using a 4-parameter logistic equation with KaleidaGraph software.
Figure 5:
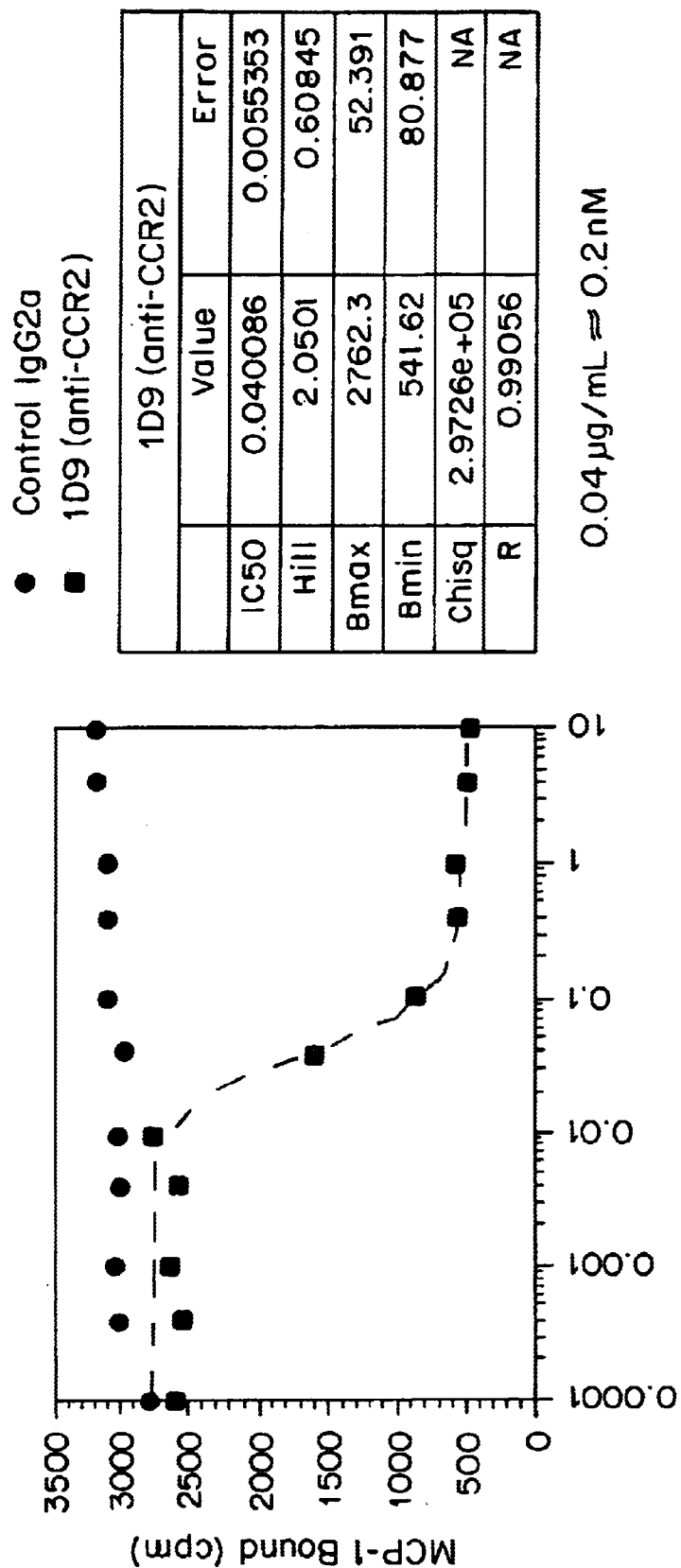
FIG. 5 illustrates that mAb 1D9 inhibits [$^{125}$I]MCP-1 binding to fresh human PBMC. Freshly isolated peripheral blood mononuclear cells (500,000) were incubated with 0.1 nM [$^{125}$I]MCP-1 in the presence of various concentrations of 1D9 or the isotype-matched anti-CXCR3 antibody 1C6. The amount of bound tracer was determined by separation of free from bound by filtration and scintillation counting. The data was analyzed to determine the $IC_{50}$ value as for FIG. 4.

MCP-1 binding was performed in a final volume of 0.1 ml of 50 mM Hepes pH 7.4, 1 mM $CaCl_2$, 5 mM $MgCl_2$, 0.02% sodium azide, 0.5% BSA (HBB), containing either 2.5 μg THP-1 membrane protein or 500,000 PBMC and 0.1 nM of [$^{125}$I]-MCP-1. Competition binding experiments were performed by including variable concentrations of unlabeled MCP-1, 1D9 antibody, or a negative control IgG2a. Non-specific binding was determined following the addition of a 2500-fold excess of unlabeled MCP-1. Samples were incubated for 60 minutes at room temperature, and bound and free tracer were separated by filtration through 96-well GF/B filterplates presoaked in 0.3% polyethyleneimine. The filters were washed in HBB further supplemented with 0.5 M NaCl, dried, and the amount of bound radioactivity determined by liquid scintillation counting. mAb 1D9 inhibits [$^{125}$I]MCP-1 binding to THP-1 cell membranes with an IC$_{50}$ of about 0.004 μg/ml (approximately 0.02 nM; FIG. 4) and to fresh PBMC with an IC$_{50}$ of 0.04 μg/ml (approximately 0.2 nM; FIG. 5).

Chemotaxis of PBMC

Figure 6A:
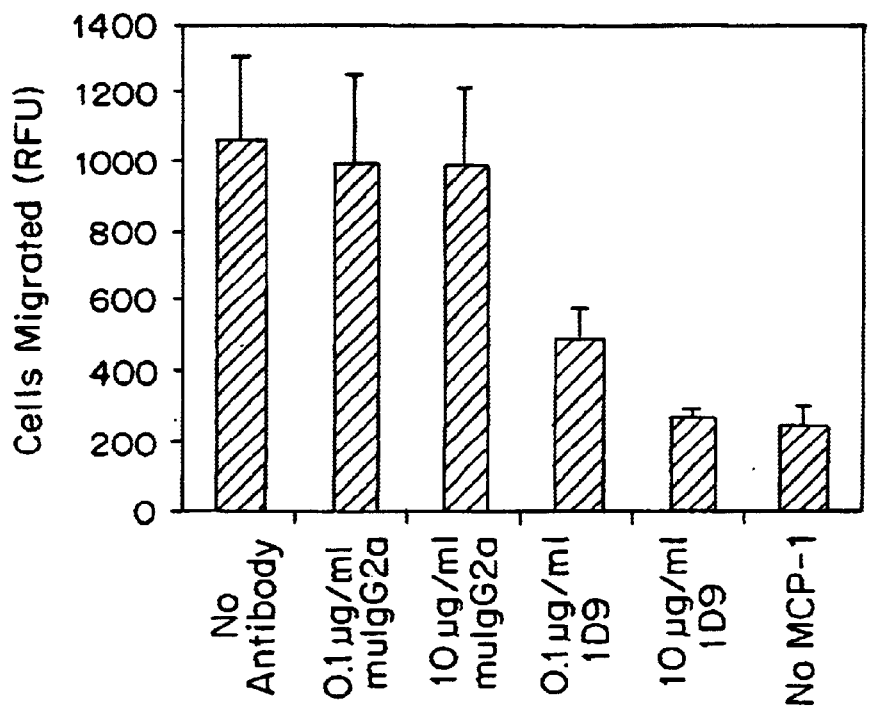
FIGS. 6A and 6B are graphs demonstrating that mAb 1D9 inhibits MCP-1-induced chemotaxis, but not RANTES-induced chemotaxis, of fresh PBMC.
Figure 6B:
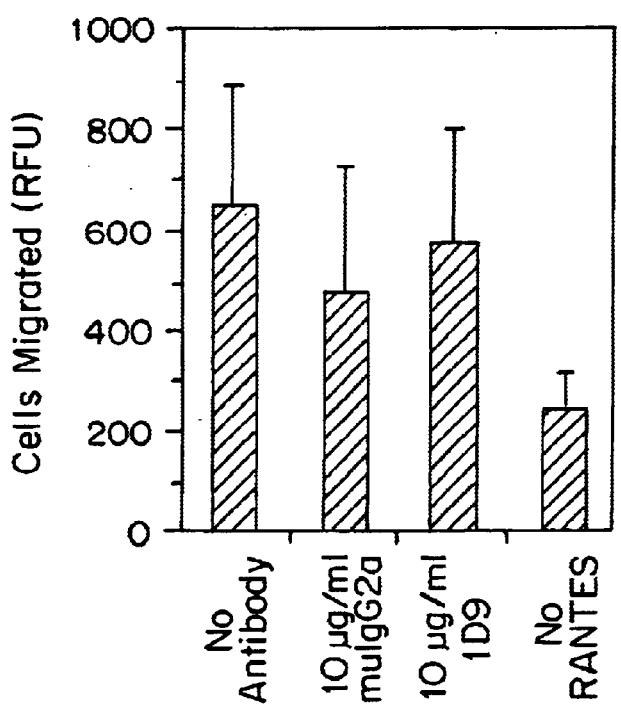

Chemotaxis was assayed using a 3 μm pore size 96-well chemotaxis plate (Neuroprobe, Cabin John, Md.). PBMC isolated by standard methods using Ficoll-Hypaque density gradient centrifugation were washed with PBS/0.5% BSA and then resuspended in chemotaxis assay media (HBSS/10 mM HEPES/0.5% Fatty acid free BSA) to a final concentration of 10×10$^6$ cells/ml. Cells were princubated in chemotaxis assay media at room temperature for 20 min. with various concentrations of the anti-CCR2 antibody, 1D9, or nonspecific murine IgG2a. The same dilutions of antibody were mixed with chemokine and 30 μl of the mixture was added to each of the bottom wells of the chemotaxis plate. The bottom wells are covered with the membrane, and 25 μl of the cell and antibody mixture are added to the top of the filter. The plates are incubated at 37° C. in 5% CO$_2$ incubator for approximately 80 min. At the completion of the migration, the membrane is removed and the plate with the bottom wells is incubated −80C for 30 minutes to freeze the contents. The plates are thawed at 37° C. for 10 minutes. 6 μl of a 1:400 dilution of CyQuant reagent (Molecular Probes, Eugene, Oreg.) in a lysis buffer provided by the supplier is added to each well, and the cell migration is quantified as indicated by fluorescence intensity determined using a CytoFlour fluorescence plate reader at 485ex/535em. mAb 1D9 inhibits MCP-1-induced chemotaxis, but not RANTES-induced chemotaxis, of fresh PBMC (FIGS. 6A and 6B). Inhibition of MCP-1-induced chemotaxis of fresh PBMC has been demonstrated with 10 μg/ml (≈40 nM).

Example 2

Humanisation of Monoclonal Antibody 1D9

The 1D9 monoclonal antibody is likely to be immunogenic in humans, potentially eliciting a human anti-mouse antibody (HAMA) response. This HAMA response usually results in rapid clearance of the mouse monoclonal antibody from the body, thus limiting any therapeutic effect the 1D9 monoclonal antibody might have. Therefore, in an effort to reduce the immunogenicity of this antibody in humans and to maximize its therapeutic potential, the humanisation of the 1D9 mouse monoclonal antibody was undertaken. The following examples provide a detailed analysis of the 1D9 amino acid sequence data, the building of a molecular model of the murine 1D9 F$_V$ domain, and the design strategy for the successful humanization of the mouse antibody. This design strategy resulted in the design of a number of humanized versions of both the kappa light chain variable (V$_K$) region and the heavy chain variable (V$_H$) region. In total, the humanized V$_H$ region included up to 16 amino acid changes in the FRs of the selected human V$_H$ region. These changes were subdivided between four versions of the humanized V$_H$ region. In addition, twelve amino acid changes in the FRs of the selected human V$_K$ region were included in the four versions of the humanized V$_K$ region which were also designed.

Sequence Analysis of the Mouse 1D9 Kappa Light Chain Variable Region

The amino acid sequence of the 1D9 V$_K$ region (FIG. 7) was compared with other mouse kappa light chain variable regions and also the consensus sequences of the subgroups that the variable regions were subdivided into in the Kabat database (Kabat et al., *Sequences of proteins of immunological interest*, Fifth edition, U.S. Department of Health and Human Services, U.S. Government Printing Office (1991)). From this analysis the 1D9 V$_K$ region was found to most closely match the mouse consensus sequence of mouse kappa subgroup II (Identity=79.46%, Similarity=82.14%). When only the FRs of the 1D9 kappa light chain variable region were compared in the mouse subgroup II, percentage identity increased to 87.5%, while percentage similarity increased to 88.75%. In addition, the mouse 1D9 V$_K$ region showed good homology to a translation of the 70/3 murine V$_K$ germline gene (FIG. 13). Taken together, the above evidence clearly proved that the 1D9 sequence was typical of a mouse V$_K$ region.

Sequence Analysis of the Mouse 1D9 Heavy Chain Variable Region

A similar analysis of the 1D9 V$_H$ region (FIG. 8) found that it matched closest to the consensus sequence of the mouse heavy chain subgroup IIIc in the Kabat database (Kabat et al., *Sequences of proteins of immunological interest*, Fifth edition, U.S. Department of Health and Human Services, U.S. Government Printing Office (1991)). Identity between the mouse heavy chain variable region amino acid sequence of 1D9 and the consensus sequence of mouse subgroup IIIc was measured at 70.94%, while the similarity was calculated to be 76.07%. When only the FRs of the 1D9 V$_H$ region was compared to mouse subgroup IIIc, percentage identity increased to 75.86%, while the similarity increased to 80.46%. The mouse 1D9 V$_H$ region also showed good homology to a translation of the MLR-RF24BG murine V$_H$ germline gene, among others (FIG. 14). Thus, the above evidence confirmed that the 1D9 sequence was typical of a mouse V$_H$ region.

Molecular Modelling of the 1D9 Domain.

To assist in the design of the humanized variable regions of the 1D9 antibody, a series of molecular models were constructed of the murine 1D9 F$_V$ region and the eight CDR grafted variants. This was done using the AbM molecular modeling package supplied and utilized by Oxford Molecular Limited (OML). Antibody α-ray crystallographic structures available from the Brookhaven database were formatted to allow them to be used for modeling with AbM.

The FRs of the 1D9 variable regions were modeled on FRs from similar, structurally-solved immunoglobulin variable regions. While identical amino acid side chains were kept in their original orientation, mismatched side chains were substituted as in the original 1D9 F$_V$. The backbone atoms of the FRs of the Fab Bv04-01 V$_K$ region were used for the model of the Fv framework region of 1D9 for both the V$_K$ and V$_H$ chains (Brookhaven PDB code 1 nbv, solved to 2.0 Å). The sequence of Fab Bv04-01 was a good match for the variable region sequences of murine 1D9 and their humanized variants. The identities between Fab Bv04-01 and the murine 1D9 and humanized sequences ranged from 76% to 78% for V$_K$ sequences and from 74% to 84% for V$_H$ sequences. Testing of AbM with known structures has shown that FR backbone homology is an important factor in the quality of any model, since the use of FR structures that poorly match a sequence being modeled can significantly and adversely affect the position and orientation of the CDR loops.

For the backbone structures of CDRs L1, L2, L3, H1 and H2, conformations for all of the models were taken from canonical classes used by AbM without modification, using the classes shown in FIGS. 9 and 10.

For the backbone structure of the L1 loop, the loop conformations of the murine 1D9 $V_K$ region was taken from canonical Class 4 from AbM. This canonical class is based on those described by Chothia and his colleagues (Chothia and Lesk, *J. Mol. Biol.* 197:901 (1987); Chothia et al., *Nature* 34:877 (1989); Tramontano et al., *J. Mol. Biol.* 215:175 (1990); and Chothia et al., *J. Mol. Biol.* 227:799 (1992)), but they have been modified to take into consideration structures that have become available since the original articles were published. Testing of the performance of AbM predictions for known loop structures has shown that CDR loops which are created in this way are usually modeled very accurately, i.e. to within 1–1.5 Å RMS deviation.

The H3 loop in the 1D9 $V_H$ region is comparatively short at six residues long. It was modeled using a search for backbone conformations from X-ray structures in the Brookhaven databank. For short loops like this, there are sufficient loop conformations from known X-ray structures to saturate the conformational space available to the loop. Testing of the predictions made by AbM with the structures of new antibodies, where the structure is not included in the databases used by the program, shows that for CDR H3 loops of this size, the accuracy is likely to be at least 2.0 Å.

After adjusting the whole of the model for obvious steric clashes it was subjected to energy minimisation, as implemented in MACROMODEL, both to relieve unfavorable atomic contacts and to optimize van der Waals and electrostatic interactions.

Design of the Humanised 1D9 $V_K$ Antibody Variants.

The first step in the design of the humanised variable regions of the 1D9 antibody was the selection of the human kappa light chain variable region that would serve as the basis for the humanized 1D9 $V_K$, region. As an aid to this process the 1D9 $V_K$ region was initially compared to the consensus sequence of the four human kappa light chain variable region subgroups as defined by Kabat (Kabat et al., *Sequences of proteins of immunological interest*, Fifth edition, U.S. Department of Health and Human Services, U.S. Government Printing Office (1991)). The mouse 1D9 light chain variable region was most similar to the consensus sequence of human kappa light chain subgroup II, with which it displayed a 76.2% identity over the whole variable region and a 82.5% identity within the FRs alone. When measured with respect to similarity, these values increased to 79.7% overall and 85.0% within the FRs alone. Consequently it generally appeared to match well to human kappa light chain variable region sequences from kappa subgroup II.

The mouse 1D9 $V_K$ was then compared to all the recorded examples of individual sequences of human variable regions publicly available. FIG. 15 shows the best seventeen matches to the mouse 1D9 $V_K$ region which were identified through this analysis. Overall, the search algorithm selected the human $V_K$ region antibody 036521 (Rheinnecker et al., *Journal of Immnunology.* 157(7):2989–97 (1996)) as the best match to the mouse 1D9 $V_K$ region (FIG. 16). However, a review of the source paper for this antibody revealed that murine oligonucleotide primers had been used to rescue the genes from the hybridoma. This meant that this antibody was in fact a murine antibody and not human, as suggested by the Kabat database. Thus,the next best match to thé murine 1D9 $V_K$ region that was selected by the database search was the human $V_K$ region from antibody HF-21/28 (Kabat database ID number 005056; Chastagner et al., Gene. 101(2):305–6 (1991)). The human sequence had an overall identity to the 1D9 $V_K$ region of 79.3% and 85.0% within the FRs alone. When measured with respect to similarity, these values increase to 83.99% overall and 87.5% within the FRs alone. In addition, key FR amino acids were more conservatively preserved in HF-21/28 $V_K$ region than in the other candidate human kappa light chain variable regions. Consequently, the HF-21/28 kappa light chain variable region FR was selected as the human acceptor sequence for the humanization of the 1D9 antibody kappa light chain variable region.

Unfortunately, the very last residue in FR4 (at position 107, according to the Kabat numbering system) of the human HF-21/28 $V_K$ region was not defined by the Kabat database or the authors who originally isolated this variable region sequence. Therefore, it was decided to insert the most commonly found amino acid at this position in the variable region sequences described by Kabat human kappa light chain subgroup κ-II (Kabat et al., *Sequences ofproteins of immunological interest*, Fifth edition, U.S. Department of Health and Human Services, U.S. Government Printing Office (1991)). Accordingly, lysine was added at position 107 in FR4 based upon an analysis of the Kabat database which found that 85.7% of the sequences in Kabat human kappa light chain subgroup $_κ$-II had a lysine at this position. This then became the basis of the first humanized version of the 1D9 kappa light chain(1D9RK$_A$), which essentially comprised the CDR's of the 1D9 $V_K$ region and the FRs of HF-21/28 $V_K$ region. FIGS. 19A–19C define the amino acid sequence of this first CDR-grafted version of the humanised 1D9 $V_K$ region.

The next step in the design process was to study the amino acid sequences of the human acceptor HF-21/28 $V_K$ region FRs to determine if any of these amino acid residues were likely to adversely influence binding to antigen. This could be caused directly through interactions with antigen, or indirectly by altering the confirmation or orientation of the CDR loops. This was a difficult process which was only made possible through the availability of a model of the 1D9 variable regions, i.e., both the $V_K$ and the $V_H$ regions. Nevertheless, any amino acids in the mouse 1D9 FRs that did appear to affect antigen binding were then considered for conversion in the humanized 1D9 antibody. In deciding which murine residues to conserve the following points were addressed:

It was of great importance that the canonical structures of the hypervariable loops (Chothia and Lesk, *J. Mol. Biol.* 197:901 (1987); Chothia et al., *Nature* 34:877 (1989); Tramontano et al.,*J. Mol. Biol.* 215:175. (1990); and Chothia et al., *J. Mol. Biol.* 227:799 (1992)) were conserved. Consequently, it was crucial to conserve in the humanized 1D9 variable regions all the mouse FR residues that were part of these canonical structures (FIGS. 9 and 10).

The sequences of the 1D9 antibody variable regions were compared to similar sequences from other mouse antibodies to identify unusual or rare residues which may have indicated an important role in antigen binding. This was then investigated using the mouse model of the 1D9 variable region genes.

A direct analysis of the model was also made to try and predict whether any of the other mouse FR residues not present in the humanized FRs could influence antigen binding in some way.

Comparisons of the individual human acceptor sequences for the kappa light chain and heavy chain variable regions to the consensus sequence of human variable regions subgroups to which the acceptor sequences belonged were also made. The identification of any idiosyncratic amino acids in the human donor sequences was important as these could have adversely affected antigen binding.

Since the human light and heavy chain variable regions selected would be derived from two different human antibodies, a careful analysis of the interdomain packing residues of both the donor and the acceptor kappa light chain variable regions should be carried out (Chothia et al., *J. Mol. Biol.* 186:651 (1985)). This was because any mispacking in this region could have had a dramatic affect upon antigen binding, irrespective of the conformation of the CDR loop structures of the humanized 1D9 antibody.

Although there were 12 amino acid differences between the FRs of the donor mouse 1D9 $V_K$ region and the acceptor human HF-21/28 $V_K$ region, only two mouse residues were considered sufficiently important for binding affinity to preserve them in the humanised FRs. The first of the FR changes that were introduced into 1D9RK$_B$ was located at position 36. This residue is a Vernier residue (Foote and Winter, *J. Mol. Biol.* 224:487 (1992)) and is predicted to be a key structure determining residue for L1 loop structure as defined by Chothia and his coworkers (Chothia and Lesk, *J. Mol. Biol.* 197:901 (1987); Chothia et al., *Nature* 34:877 (1989); Tramontano et al., *J. Mol. Biol.* 215:175 (1990); and Chothia et al., *J. Mol. Biol.* 227:799 (1992)). Although both residues are hydrophobic, the human Phe is bulkier at this position, and X-ray structures with Leu and Phe at this position show that if Phe is present steric hindrance causes the side chain at 34Asn to point in the opposite direction. Thus, it was considered critical for the successful humanization of the 1D9 kappa light chain. The second change incorporated into the ID$^9$RK$_B$ humanized version was at residue 37, i.e., Gln37Leu. Although this was a conservative change it occurred in a highly conserved region at the base of CDR1. It was thought that by preserving this murine Leu residue in this version, alongside the murine Leu residue at position 36, the affinity of the humanised antibody could be preserved.

Two other versions of the humanised $V_K$ region were also considered for construction to explore the structural and binding affinity consequences of manipulating the FRs of the humanised 1D9 antibody. 1D9RK$_C$ was essentially identical to 1D9RK$_B$, except for the mutation Gln100Gly. There is a dramatic difference in molecule bulk between these two residues, and thus this version was made to explore the consequences of this change to the FRs of the reshaped human kappa light chain on antibody structure and overall antibody affinity. 1D9RK$_D$ contained the modifications described in 1D9RK$_C$ and, in addition, contained the FR change Gln17His. Although Gln and His are similar in size and both are weakly polar, the mouse residue (His) at this position is extremely rare amongst all mouse $V_K$ sequences (0.07% overall, but has not been seen in mouse Kabat subgroup II sequences) and has never been seen in any human $V_K$ sequences. Conversely, the Gln residue is more commonly seen at this position in both mouse (16.16% overall and 6.12% in mouse Kabat subgroup II sequences) and human (5.00% overall and 39.7% in human Kabat subgroup II sequences) sequences. Thus, the simple rarity of the His at this position suggests that it may be important for binding, although there is no clear evidence to support this from the molecular modeling data. A description of the amino acid sequences of all the humanised 1D9 antibody $V_K$ region variants proposed above are given in FIG. 11.

Design of Humanised 1D9 $V_H$ Antibody Variants

Once again, the first step in the design of the humanised $V_H$ region of the mouse 1D9 antibody was the selection of the acceptor human heavy chain variable region that would serve as the basis of the humanised 1D9 $V_H$ region. When the 1D9 $V_H$ region was initially compared to the consensus sequences of the three human heavy chain variable region subgroups it was found to be most similar to the consensus sequence for the human heavy chain subgroup III, with a 69.231% identity overall and a 78.161% identity between the FRs alone. When measured with respect to similarity, these values increased to 74.359% overall and to 82.759% within the FRs alone.

Figure 17A:
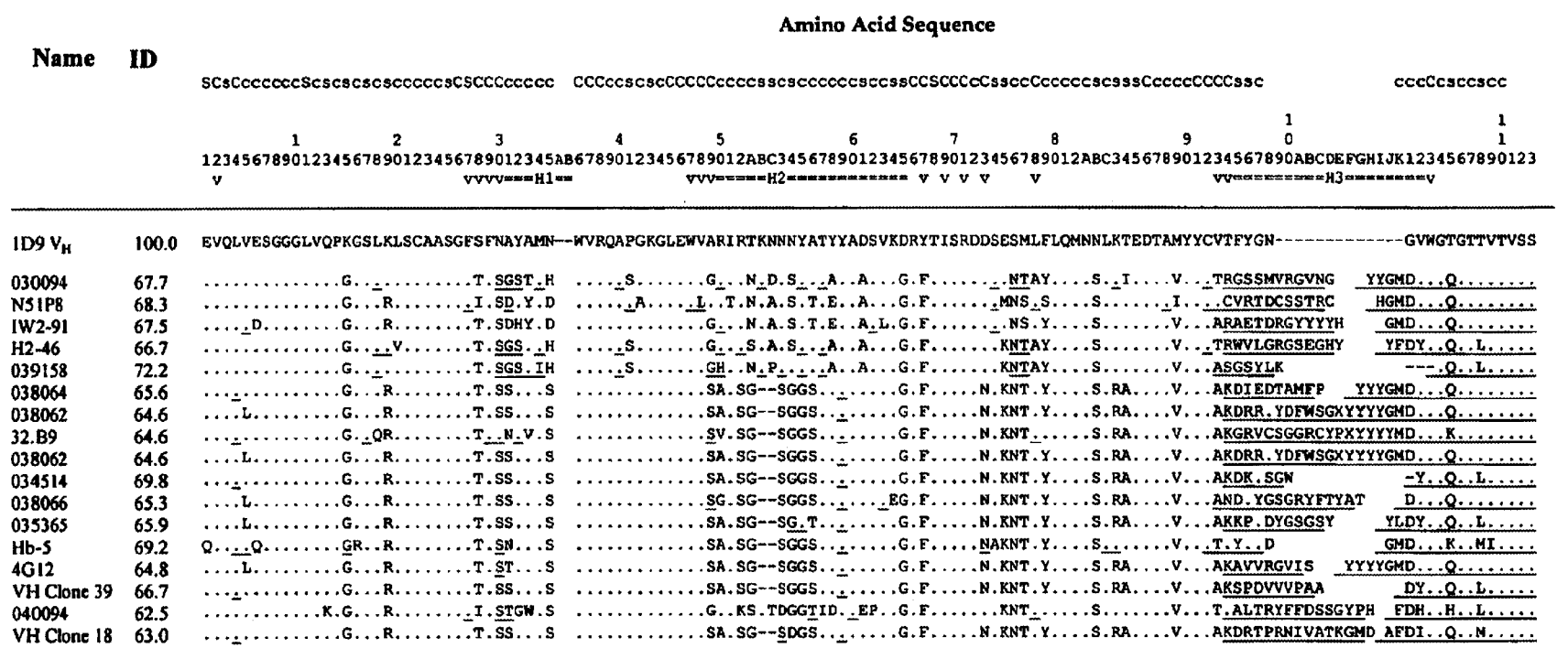
Figure 17B:
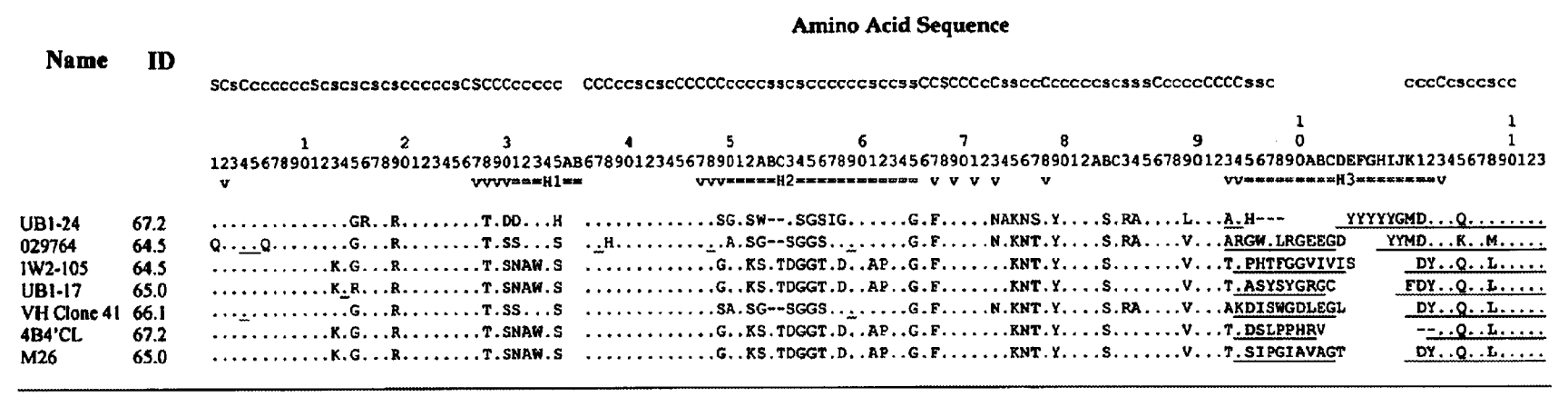

The mouse 1D9 $V_H$ region was then compared to all the recorded examples of individual sequences of human variable regions publicly available. FIGS. 17A–B show the best 24 matches to the mouse 1D9 $V_H$ region which were identified through this analysis. Overall the search algorithm selected the human $V_H$ region from antibody 4B4'CL (Kabat data base ID number 000490; Sanz et al., *Journal of Immunology*. 142:883 (1989)) as the best match to the mouse 1D9 $V_H$ region. The $V_H$ region of this clone had an overall identity to the 1D9 $V_H$ region of 67.2%, a value which increased to 80.95% when the FRs alone were compared (FIGS. 18A–B). When measured with respect to similarity, these values increased to 69.66% overall and to 84.52% within the FRs alone. Thus, although once again not the most homologous of the potential human acceptor $V_H$ sequences, this human FR became the basis of the humanised version of the 1D9 heavy chain.

The next step in the design process was to study the amino acid sequences of the human acceptor 4B4'CL $V_H$ region FRs to determine if any of these amino acid residues were likely to adversely affect binding to antigen. Once again the molecular models built by OML were important in this design process, from which a number of amino acids in the murine 1D9 $V_H$ region FRs were identified for conversion in the first (1D9RH$_A$) and subsequent versions of the humanised 1D9 antibody (FIG. 12 and FIGS. 20A–C). There were 16 amino acid differences between the FRs of the donor mouse 1D9 and the acceptor human 4B4'CL $V_H$ regions, and up to 5 murine residues were considered for conservation in the humanised FRs (FIG. 12).

1D9RHA consisted of the CDRs of the murine 1D9 antibody $V_H$ region genetically inserted into the FRs of the human 4B4'CL antibody $V_H$ region. 1D9RH$_B$ was identical to version 1D$^9$RH$_A$ apart from two FR1 mutations, Thr28Ser and Asn30Ser. These changes were made because they represented Vernier amino acids as defined by Foote and Winter (*J. Mol. Biol.* 224:487 (1992)), which were thought to be critical for H1 loop conformation. Residues 27–30 are considered part of the H1 loop itself and so are even more critical to the correct conformation and orientation of this loop, justifying their conservation even more strongly. Thus, these two residues represented the sum of the changes made to the FRs of the human 4B4'CL $V_H$ sequence in 1D$^9$RH$_B$. 1D9RH$_C$ was identical to version 1D9RH$_B$ except that it contained two further changes at positions Gly49Al a and Phe67Tyr. The Gly49Ala was a conservative change. However, residue position 49 has been identified as a Vernier residue (Foote and Winter, *J. Mol. Biol.* 224:487 (1992)), important for H2 hypervariable loop structure, so it was decided to conserve the murine Ala residue in this version. Residue position 67 was also a Vernier residue position, identifying it as important for maintaining CDR loop conformation. Tyr is very rarely seen in human $V_H$ sequences (0.08% overall) and has not previously been found in murine $V_H$ regions at this position. Consequently, it must have arisen through somatic mutation. Thus, given its location close to CDR2 according to the molecular model and its Vernier residue status, it was decided to conserve the murine Tyr residue at this position. 1D9RH$_D$ was identical to 1D9RH$_C$ except for a Thr93Val mutation. This residue had been identified as important as both a $V_H/V_K$ packing residue (Chothia et al., *J. Mol. Biol.* 186:651 (1985)). Moreover, its buried position between CDR loops H1 and H3, according to the molecular model, supported the decision to conserve the murine Val residue at this position. A description of the amino acid sequences of all the humanised $V_H$ region variants described above are given in FIG. 12.

While this invention has been particularly shown and described with references to preferred embodiments thereof, it will be understood by those skilled in the art that various changes in form and details may be made therein without departing from the scope of the invention encompassed by the appended claims.

What is claimed is:

1. A humanized immunoglobulin having binding specificity for CC-chemokine receptor 2 (CCR2), said immunoglobulin comprising an antigen binding region from monoclonal antibody 1D9 and a light chain framework region derived from the light chain of the HF-21/28 antibody.

2. The humanized immunoglobulin of claim 1 further comprising a constant region derived from a human constant region.

3. The humanuoglobulin of claim 2 wherein the human constant region is of the gamma type.

4. The humanized immunoglobulin of claim 1 wherein the antigen binding region comprises the three complementarity determining regions of the light chain variable region of monoclonal antibody 1D9 and the three complementarity determining regions of the heavy chain variable region of monoclonal antibody 1D9.

5. A humanized immunoglobulin having binding specificity for CC-chemokine receptor 2 (CCR2) comprising a heavy chain and a light chain, wherein said light chain comprises three complementarity determining regions from the light chain of monoclonal antibody 1D9 and a framework region derived from the light chain of the HF-21/28 antibody, and wherein said heavy chain comprises three complementarity determining regions from the heavy chain of monoclonal antibody 1D9 and a framework region derived from a heavy chain of human origin.

6. The humanized immunoglobulin of claim 5 wherein said immunoglobulin can compete with murine monoclonal antibody 1D9 for binding to CCR2.

7. The humanized immunoglobulin of claim 5 wherein the heavy chain of human origin is the heavy chain of the human 4B4'CL antibody.

8. A pharmaceutical composition comprising a humanized immunoglobulin having binding specificity for CC-chemokine receptor 2 (CCR2), said immunoglobulin comprising an antigen binding region from monoclonal antibody 1D9 and a framework region derived from the light chain of the HF-21/28 antibody, and a suitable carrier.

9. A pharmaceutical composition comprising a humanized immunoglobulin having binding specificity for CC-chemokine receptor 2 (CCR2) comprising a heavy chain and a light chain, wherein said light chain comprises three complementarity determining regions from the light chain of monoclonal antibody 1D9 and a framework region derived from the light chain of the HF-21/28 antibody, and wherein said heavy chain comprises three complementarity determining regions from the heavy chain of monoclonal antibody 1D9 and a framework region derived from a heavy chain of human origin, and a suitable carrier.

10. A humanized immunoglobulin having binding specificity for CC-chemokine receptor 2 (CCR2), said immunoglobulin comprising an antigen binding region from monoclonal antibody 1D9 and a heavy chain framework region derived from the heavy chain of the 4B4'CL antibody.

11. The humanized immunoglobulin of claim 10 further comprising a constant region derived from a human constant region.

12. The humanized immunoglobulin of claim 11 wherein the human constant region is of the gamma type.

13. The humanized immunoglobulin of claim 10 wherein the antigen binding region comprises the three complementarity determining regions of the light chain variable region of monoclonal antibody 1D9 and the three complementarity determining regions of the heavy chain variable region of monoclonal antibody 1D9.

14. A humanized immunoglobulin having binding specificity for CC-chemokine receptor 2 (CCR2) comprising a heavy chain and a light chain, wherein said light chain comprises three complementarity determining regions from the light chain of monoclonal antibody 1D9 and a framework region derived from a light chain of human origin, and wherein said heavy chain comprises three complementarity determining regions from the heavy chain of monoclonal antibody 1D9 and a framework region derived from the heavy chain of the 4B4'CL antibody.

15. The humanized immunoglobulin of claim 14 wherein said immunoglobulin can compete with murine monoclonal antibody 1D9 for binding to CCR2.

16. The humanized immunoglobulin of claim 14 wherein the light chain of human origin is the light chain of the human HF-21/28 antibody.

17. A pharmaceutical composition comprising a humanized immunoglobulin having binding specificity for CC-chemokine receptor 2 (CCR2), said immunoglobulin comprising an antigen binding region from monoclonal antibody 1D9 and a framework region derived from the heavy chain of the 4B4'CL antibody, and a suitable carrier.

18. A pharmaceutical composition comprising a humanized immunoglobulin having binding specificity for CC-chemokine receptor 2 (CCR2) comprising a heavy chain and a light chain, wherein said light chain comprises three complementarity determining regions from the light chain of monoclonal antibody 1D9 and a framework region derived from a light chain of human origin, and wherein said heavy chain comprises three complementarity determining regions from the heavy chain of monoclonal antibody 1D9 and a framework region derived from the heavy chain of the 4B4'CL antibody, and a suitable carrier.

19. A humanized immunoglobulin light chain comprising CDR1, CDR2 and CDR3 of the light chain of monoclonal antibody 1D9 and a light chain framework region derived from a human light chain.

20. The humanized immunoglobulin light chain of claim 19 wherein the human light chain is the light chain of the HF-21/28 antibody.

21. The humanized immunoglobulin light chain of claim 19 comprising the variable region of SEQ ID NO: 9.

22. A humanized immunoglobulin heavy chain comprising CDR1, CDR2 and CDR3 of the heavy chain of monoclonal antibody 1D9 and a heavy chain framework region derived from a human heavy chain.

23. The humanized immunoglobulin heavy chain of claim 22 wherein the human heavy chain is the heavy chain of the human 4B4'CL antibody.

24. The humanized immunoglobulin heavy chain of claim 22 comprising the variable region of SEQ ID NO: 10.

25. A humanized immunoglobulin light chain comprising an amino acid sequence selected from the group consisting of:

a) SEQ ID NO: 12;
b) SEQ ID NO: 13;
c) SEQ ID NO: 14; and
d) SEQ ID NO: 15.

26. A humanized immunoglobulin heavy chain comprising an amino acid sequence selected from the group consisting of:

a) SEQ ID NO: 17;
b) SEQ ID NO: 18;
c) SEQ ID NO: 19; and
d) SEQ ID NO: 20.

27. A humanized immunoglobulin having binding specificity for CC-chemokine receptor 2 (CCR2), said immunoglobulin comprising a heavy chain and a light chain, wherein said light chain comprises a variable region selected from the group consisting of SEQ ID NO: 12, SEQ ID NO: 13, SEQ ID NO: 14 and SEQ ID NO: 15, and wherein said heavy chain comprises three complementarity determining regions from the heavy chain of monoclonal antibody 1D9 and a framework region derived from a heavy chain of human origin.

28. A humanized immunoglobulin having binding specificity for CC-chemokine receptor 2 (CCR2), said immunoglobulin comprising a heavy chain and a light chain, wherein said light chain comprises three complementarity determining regions from the light chain of monoclonal antibody 1D9, and wherein said heavy chain comprises a variable region selected from the group consisting of SEQ ID NO: 17, SEQ ID NO: 18, SEQ ID NO: 19 and SEQ ID NO:20.

29. A humanized immunoglobulin having binding specificity for CC-chemokine receptor 2 (CCR2), said immunoglobulin or fragment comprising a heavy chain and a light chain, wherein said light chain comprises a variable region selected from the group consisting of SEQ ID NO: 12, SEQ ID NO: 13, SEQ ID NO: 14 and SEQ ID NO: 15, and wherein said heavy chain comprises a variable region selected from the group consisting of SEQ ID NO: 17, SEQ ID NO: 18, SEQ ID NO: 19 and SEQ ID NO:20.

30. A pharmaceutical composition comprising a humanized immunoglobulin having binding specificity for CC-chemokine receptor 2 (CCR2) comprising CDR1, CDR2 and CDR3 of the light chain of monoclonal 1D9 antibody and a framework region derived from a human light chain framework region, and a suitable carrier.

31. A pharmaceutical composition according to claim 30 wherein the human light chain framework region is the light chain framework region of the HF-21/28 antibody.

32. A pharmaceutical composition comprising a humanized immunoglobulin having binding specificity for CC-chemokine receptor 2 (CCR2) comprising CDR1, CDR2 and CDR3 of the heavy chain of monoclonal 1D9 antibody and a framework region derived from a human heavy chain framework region, and a suitable carrier.

33. A pharmaceutical composition according to 32 wherein the human heavy chain framework region is the heavy chain framework region of the 4B4'CL antibody.

34. A humanized immunoglobulin light chain comprising the amino acid sequence of SEQ ID NO: 12.

35. A humanized immunoglobulin heavy chain comprising the amino acid sequence of SEQ ID NO: 17.

36. A humanized immunoglobulin having binding specificity for CC-chemokine receptor 2 (CCR2) comprising a light chain comprising the amino acid sequence of SEQ ID NO: 12 and a heavy chain comprising the amino acid sequence of SEQ ID NO: 17.

37. A pharmaceutical composition comprising a humanized immunoglobulin having binding specificity for CC-chemokine receptor 2 (CCR2) comprising a light chain comprising the amino acid sequence of SEQ ID NO: 12 and a heavy chain comprising the amino acid sequence of SEQ ID NO: 17, and a suitable carrier.

38. A humanized immunoglobulin having binding specificity for CC-chemokine receptor 2 (CCR2), said immunoglobulin comprising an antigen binding region from monoclonal antibody 1D9, a light chain framework region derived from the light chain of the HF-21/28 antibody, and a heavy chain framework region derived from the heavy chain of the 4B4'CL antibody.

39. A humanized immunoglobulin having binding specificity for CC-chemokine receptor 2 (CCR2) comprising a heavy chain and a light chain, wherein said light chain comprises three complementarity determining regions from the light chain of monoclonal antibody 1D9 and a framework region derived from the light chain of the HF-21/28 antibody, and wherein said heavy chain comprises three complementarity determining regions from the heavy chain of monoclonal antibody 1D9 and a framework region derived from the heavy chain of the 4B4'CL antibody.

40. A pharmaceutical composition comprising a humanized immunoglobulin having binding specificity for CC-chemokine receptor 2 (CCR2), said immunoglobulin comprising an antigen binding region from monoclonal antibody 1D9, a light chain framework region derived from the light chain of the HF-21/28 antibody, and a heavy chain framework region derived from the heavy chain of the 4B4'CL antibody, and a suitable carrier.

41. A pharmaceutical composition comprising a humanized immunoglobulin having binding specificity for CC-chemokine receptor 2 (CCR2) comprising a heavy chain and a light chain, wherein said light chain comprises three complementarity determining regions from the light chain of monoclonal antibody 1D9 and a framework region derived from the light chain of the HF-21/28 antibody, and wherein said heavy chain comprises three complementarity determining regions from the heavy chain of monoclonal antibody 1D9 and a framework region derived from the heavy chain of the 4B4'CL antibody, and a suitable carrier.

42. An antigen binding fragment of a humanized immunoglobulin having binding specificity for CC-chemokine receptor 2 (CCR2), said immunoglobulin comprising an antigen binding region from monoclonal antibody 1D9 and a light chain framework region derived from the light chain of the HF-21/28 antibody.

43. An antigen binding fragment of a humanized immunoglobulin having binding specificity for CC-chemokine receptor 2 (CCR2), said immunoglobulin comprising a heavy chain and a light chain, wherein said light chain comprises three complementarity determining regions from the light chain of monoclonal antibody 1D9 and a framework region derived from the light chain of the HF-21/28 antibody, and wherein said heavy chain comprises three complementarity determining regions from the heavy chain of monoclonal antibody 1D9 and a framework region derived from a heavy chain of human origin.

44. A pharmaceutical composition comprising an antigen binding fragment of a humanized immunoglobulin having binding specificity for CC-chemokine receptor 2 (CCR2), said immunoglobulin comprising an antigen binding region from monoclonal antibody 1D9 and a framework region derived from the light chain of the HF-21/28 antibody, and a suitable carrier.

45. A pharmaceutical composition comprising an antigen binding fragment of a humanized immunoglobulin having binding specificity for CC-chemokine receptor 2 (CCR2), said immunoglobulin comprising a heavy chain and a light chain, wherein said light chain comprises three complementarity determining regions from the light chain of monoclonal antibody 1D9 and a framework region derived from the light chain of the HF-21/28 antibody, and wherein said heavy chain comprises three complementarity determining regions from the heavy chain of monoclonal antibody 1D9 and a framework region derived from a heavy chain of human origin, and a suitable carrier.

46. An antigen binding fragment of a humanized immunoglobulin having binding specificity for CC-chemokine receptor 2 (CCR2), said immunoglobulin comprising an antigen binding region from monoclonal antibody 1D9 and a heavy chain framework region derived from the heavy chain of the 4B4'CL antibody.

47. An antigen binding fragment of a humanized immunoglobulin having binding specificity for CC-chemokine receptor 2 (CCR2), said immunoglobulin comprising a heavy chain and a light chain, wherein said light chain comprises three complementarity determining regions from the light chain of monoclonal antibody 1D9 and a framework region derived from a light chain of human origin, and wherein said heavy chain comprises three complementarity determining regions from the heavy chain of monoclonal antibody 1D9 and a framework region derived from the heavy chain of the 4B4'CL antibody.

48. A pharmaceutical composition comprising an antigen binding fragment of a humanized immunoglobulin having binding specificity for CC-chemokine receptor 2 (CCR2), said immunoglobulin comprising an antigen binding region from monoclonal antibody 1D9 and a framework region derived from the heavy chain of the 4B4'CL antibody, and a suitable carrier.

49. A pharmaceutical composition comprising an antigen binding fragment of a humanized immunoglobulin having binding specificity for CC-chemokine receptor 2 (CCR2), said immunoglobulin comprising a heavy chain and a light chain, wherein said light chain comprises three complementarity determining regions from the light chain of monoclonal antibody 1D9 and a framework region derived from a light chain of human origin, and wherein said heavy chain comprises three complementarity determining regions from the heavy chain of monoclonal antibody 1D9 and a framework region derived from the heavy chain of the 4B4'CL antibody, and a suitable carrier.

50. An antigen binding fragment of a humanized immunoglobulin having binding specificity for CC-chemokine receptor 2 (CCR2), said immunoglobulin comprising a heavy chain and a light chain, wherein said light chain comprises a variable region selected from the group consisting of SEQ ID NO: 12, SEQ ID NO: 13, SEQ ID NO: 14 and SEQ ID NO: 15, and wherein said heavy chain comprises three complementarity determining regions from the heavy chain of monoclonal antibody 1D9 and a framework region derived from a heavy chain of human origin.

51. An antigen binding fragment of a humanized immunoglobulin having binding specificity for CC-chemokine receptor 2 (CCR2), said immunoglobulin comprising a heavy chain and a light chain, wherein said light chain comprises three complementarity determining regions from the light chain of monoclonal antibody 1D9, and wherein said heavy chain comprises a variable region selected from the group consisting of SEQ ID NO: 17, SEQ ID NO: 18, SEQ ID NO: 19 and SEQ ID NO:20.

52. An antigen binding fragment of a humanized immunoglobulin having binding specificity for CC-chemokine receptor 2 (CCR2), said immunoglobulin comprising a heavy chain and a light chain, wherein said light chain comprises a variable region selected from the group consisting of SEQ ID NO: 12, SEQ ID NO: 13, SEQ ID NO: 14 and SEQ ID NO: 15, and wherein said heavy chain comprises a variable region selected from the group consisting of SEQ ID NO: 17, SEQ ID NO: 18, SEQ ID NO: 19 and SEQ ID NO:20.

53. A pharmaceutical composition comprising an antigen binding fragment of a humanized immunoglobulin having binding specificity for CC-chemokine receptor 2 (CCR2), said immunoglobulin comprising CDR1, CDR2 and CDR3 of the light chain of monoclonal 1D9 antibody and a framework region derived from a human light chain framework region, and a suitable carrier.

54. A pharmaceutical composition according to claim 53 wherein the human light chain framework region is the light chain framework region of the HF-21/28 antibody.

55. A pharmaceutical composition comprising an antigen binding fragment of a humanized immunoglobulin having binding specificity for CC-chemokine receptor 2 (CCR2), said immunoglobulin comprising CDR1, CDR2 and CDR3 of the heavy chain of monoclonal 1D9 antibody and a framework region derived from a human heavy chain framework region, and a suitable carrier.

56. A pharmaceutical composition according to claim 55 wherein the human heavy chain framework region is the heavy chain framework region of the 4B4'CL antibody.

57. An antigen binding fragment of a humanized immunoglobulin having binding specificity for CC-chemokine receptor 2 (CCR2), said immunoglobulin comprising a light chain comprising the amino acid sequence of SEQ ID NO: 12 and a heavy chain comprising the amino acid sequence of SEQ ID NO: 17.

58. A pharmaceutical composition comprising an antigen binding fragment of a humanized immunoglobulin having binding specificity for CC-chemokine receptor 2 (CCR2), said immunoglobulin comprising a light chain comprising the amino acid sequence of SEQ ID NO: 12 and a heavy chain comprising the amino acid sequence of SEQ ID NO: 17, and a suitable carrier.

59. An antigen binding fragment of a humanized immunoglobulin having binding specificity for CC-chemokine receptor 2 (CCR2), said immunoglobulin comprising an antigen binding region from monoclonal antibody 1D9, a light chain framework region derived from the light chain of the HF-21/28 antibody, and a heavy chain framework region derived from the heavy chain of the 4B4'CL antibody.

60. An antigen binding fragment of a humanized immunoglobulin having binding specificity for CC-chemokine receptor 2 (CCR2), said immunoglobulin comprising a heavy chain and a light chain, wherein said light chain comprises three complementarity determining regions from the light chain of monoclonal antibody 1D9 and a framework region derived from the light chain of the HF-21/28 antibody, and wherein said heavy chain comprises three complementarity determining regions from the heavy chain of monoclonal antibody 1D9 and a framework region derived from the heavy chain of the 4B4'CL antibody.

61. A pharmaceutical composition comprising an antigen binding fragment of a humanized immunoglobulin having binding specificity for CC-chemokine receptor 2 (CCR2), said immunoglobulin comprising an antigen binding region from monoclonal antibody 1D9, a light chain framework region derived from the light chain of the HF-21/28 antibody, and a heavy chain framework region derived from the heavy chain of the 4B4'CL antibody, and a suitable carrier.

62. A pharmaceutical composition comprising an antigen binding fragment of a humanized immunoglobulin having binding specificity for CC-chemokine receptor 2 (CCR2), said immunoglobulin comprising a heavy chain and a light chain, wherein said light chain comprises three complementarity determining regions from the light chain of monoclonal antibody 1D9 and a framework region derived from the light chain of the HF-21/28 antibody, and wherein said heavy chain comprises three complementarity determining regions from the heavy chain of monoclonal antibody 1D9 and a framework region derived from the heavy chain of the 4B4'CL antibody, and a suitable carrier.

* * * * *

SEQUENCE LISTING

<160> NUMBER OF SEQ ID NOS: 106

<210> SEQ ID NO 1
<211> LENGTH: 22
<212> TYPE: DNA
<213> ORGANISM: Artificial Sequence
<220> FEATURE:
<223> OTHER INFORMATION: Primer sequence

<400> SEQUENCE: 1
tgagacaagc cacaagctga ac                                22

<210> SEQ ID NO 2
<211> LENGTH: 22
<212> TYPE: DNA
<213> ORGANISM: Artificial Sequence
<220> FEATURE:
<223> OTHER INFORMATION: Primer sequence

<400> SEQUENCE: 2
tctgtattag tacacacagc cc                                22

<210> SEQ ID NO 3
<211> LENGTH: 24
<212> TYPE: DNA
<213> ORGANISM: Artificial Sequence
<220> FEATURE:
<223> OTHER INFORMATION: Primer sequence

<400> SEQUENCE: 3
atgctgtcca catctcgttc tcgg                              24

<210> SEQ ID NO 4
<211> LENGTH: 27
<212> TYPE: DNA
<213> ORGANISM: Artificial Sequence
<220> FEATURE:
<223> OTHER INFORMATION: Primer sequence

<400> SEQUENCE: 4
ttataaacca gccgagactt cctgctc                           27

<210> SEQ ID NO 5
<211> LENGTH: 24
<212> TYPE: PRT
<213> ORGANISM: Artificial Sequence
<220> FEATURE:
<223> OTHER INFORMATION: CD5 signal peptide leader sequence

<400> SEQUENCE: 5

Met Pro Met Gly Ser Leu Gln Pro Leu Ala Thr Leu Tyr Leu Leu Gly
 1               5                  10                  15

Met Leu Val Ala Ser Val Leu Ala
            20

<210> SEQ ID NO 6
<211> LENGTH: 60
<212> TYPE: DNA
<213> ORGANISM: Artificial Sequence
<220> FEATURE:
<223> OTHER INFORMATION: Primer

<400> SEQUENCE: 6 gggatccag aaaccatgcc catggggtct ctgcaaccgc tggccacctt gtacctgctg    60

<210> SEQ ID NO 7
<211> LENGTH: 65
<212> TYPE: DNA
<213> ORGANISM: Artificial Sequence
<220> FEATURE:
<223> OTHER INFORMATION: Primer

<400> SEQUENCE: 7
gccaccttgt acctgctggg gatgctggtc gcttccgtgc tagcgatgct gtccacatct    60
cgttc                                                                65

<210> SEQ ID NO 8
<211> LENGTH: 18
<212> TYPE: DNA
<213> ORGANISM: Artificial Sequence
<220> FEATURE:
<223> OTHER INFORMATION: Primer

<400> SEQUENCE: 8
gacgaccagc atgttgcc                                                  18

<210> SEQ ID NO 9
<211> LENGTH: 112
<212> TYPE: PRT
<213> ORGANISM: Mus musculus

<400> SEQUENCE: 9

Asp Val Val Met Thr Gln Thr Pro Leu Thr Leu Ser Val Thr Val Gly
 1               5                  10                  15

His Pro Ala Ser Ile Ser Cys Lys Ser Ser Gln Ser Leu Leu Asp Ser
                20                  25                  30

Asp Gly Lys Thr Phe Leu Asn Trp Leu Leu Gln Arg Pro Gly Gln Ser
            35                  40                  45

Pro Lys Arg Leu Ile Tyr Leu Val Ser Lys Leu Asp Ser Gly Val Pro
        50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Trp Gln Gly
                85                  90                  95

Thr His Phe Pro Tyr Thr Phe Gly Gly Gly Thr Lys Leu Glu Ile Lys
                100                 105                 110

<210> SEQ ID NO 10
<211> LENGTH: 117
<212> TYPE: PRT
<213> ORGANISM: Mus musculus

<400> SEQUENCE: 10

Glu Val Gln Leu Val Glu Ser Gly Gly Gly Leu Val Gln Pro Lys Gly

-continued

```
                1               5                  10                    15
Ser Leu Lys Leu Ser Cys Ala Ala Ser Gly Phe Ser Phe Asn Ala Tyr
            20                  25                  30

Ala Met Asn Trp Val Arg Gln Ala Pro Gly Lys Gly Leu Glu Trp Val
        35                  40                  45

Ala Arg Ile Arg Thr Lys Asn Asn Tyr Ala Thr Tyr Tyr Ala Asp
    50                  55                  60

Ser Val Lys Asp Arg Tyr Thr Ile Ser Arg Asp Asp Ser Glu Ser Met
65                  70                  75                  80

Leu Phe Leu Gln Met Asn Asn Leu Lys Thr Glu Asp Thr Ala Met Tyr
                85                  90                  95

Tyr Cys Val Thr Phe Tyr Gly Asn Gly Val Trp Gly Thr Gly Thr Thr
            100                 105                 110

Val Thr Val Ser Ser
            115
```

<210> SEQ ID NO 11
<211> LENGTH: 111
<212> TYPE: PRT
<213> ORGANISM: Homo sapiens

<400> SEQUENCE: 11

```
Asp Val Val Met Thr Gln Ser Pro Leu Ser Leu Pro Val Thr Leu Gly
1               5                  10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Phe Thr Phe Gly Gln Gly Thr Arg Leu Glu Ile
            100                 105                 110
```

<210> SEQ ID NO 12
<211> LENGTH: 112
<212> TYPE: PRT
<213> ORGANISM: Artificial Sequence
<220> FEATURE:
<223> OTHER INFORMATION: Humanized sequence

<400> SEQUENCE: 12

```
Asp Val Val Met Thr Gln Ser Pro Leu Ser Leu Pro Val Thr Leu Gly
1               5                  10                  15

Gln Pro Ala Ser Ile Ser Cys Lys Ser Ser Gln Ser Leu Leu Asp Ser
            20                  25                  30

Asp Gly Lys Thr Phe Leu Asn Trp Phe Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95
```

Thr His Phe Pro Tyr Thr Phe Gly Gln Gly Thr Arg Leu Glu Ile Lys
            100                 105                 110

<210> SEQ ID NO 13
<211> LENGTH: 112
<212> TYPE: PRT
<213> ORGANISM: Artificial Sequence
<220> FEATURE:
<223> OTHER INFORMATION: Humanized sequence

<400> SEQUENCE: 13

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Phe Leu Asn Trp Leu Leu Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gln Gly Thr Arg Leu Glu Ile Lys
            100                 105                 110

<210> SEQ ID NO 14
<211> LENGTH: 112
<212> TYPE: PRT
<213> ORGANISM: Artificial Sequence
<220> FEATURE:
<223> OTHER INFORMATION: Humanized sequence

<400> SEQUENCE: 14

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Phe Leu Asn Trp Leu Leu Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gly Gly Thr Arg Leu Glu Ile Lys
            100                 105                 110

<210> SEQ ID NO 15
<211> LENGTH: 112
<212> TYPE: PRT
<213> ORGANISM: Artificial Sequence
<220> FEATURE:
<223> OTHER INFORMATION: Humanized sequence

<400> SEQUENCE: 15

Asp Val Val Met Thr Gln Ser Pro Leu Ser Leu Pro Val Thr Leu Gly
1               5                   10                  15

```
His Pro Ala Ser Ile Ser Cys Lys Ser Ser Gln Ser Leu Leu Asp Ser
            20                  25                  30

Asp Gly Lys Thr Phe Leu Asn Trp Leu Leu Gln Arg Pro Gly Gln Ser
        35                  40                  45

Pro Arg Arg Leu Ile Tyr Leu Val Ser Lys Leu Asp Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gly Gly Thr Arg Leu Glu Ile Lys
                100                 105                 110
```

<210> SEQ ID NO 16
<211> LENGTH: 119
<212> TYPE: PRT
<213> ORGANISM: Homo sapiens

<400> SEQUENCE: 16

```
Glu Val Gln Leu Val Glu Ser Gly Gly Gly Leu Val Lys Pro Gly Gly
 1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
 50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Ser Leu Pro Pro His Arg Val Trp Gly Gln Gly
                100                 105                 110

Thr Leu Val Thr Val Ser Ser
        115
```

<210> SEQ ID NO 17
<211> LENGTH: 117
<212> TYPE: PRT
<213> ORGANISM: Artificial Sequence
<220> FEATURE:
<223> OTHER INFORMATION: Humanized sequence

<400> SEQUENCE: 17

```
Glu Val Gln Leu Val Glu Ser Gly Gly Gly Leu Val Lys Pro Gly Gly
 1               5                   10                  15

Ser Leu Arg Leu Ser Cys Ala Ala Ser Gly Phe Thr Phe Ser Ala Tyr
            20                  25                  30

Ala Met Asn Trp Val Arg Gln Ala Pro Gly Lys Gly Leu Glu Trp Val
        35                  40                  45

Gly Arg Ile Arg Thr Lys Asn Asn Tyr Ala Thr Tyr Tyr Ala Asp
 50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Phe Tyr Gly Asn Gly Val Trp Gly Gln Gly Thr Leu
```

```
                    100                 105                 110

Val Thr Val Ser Ser
        115

<210> SEQ ID NO 18
<211> LENGTH: 117
<212> TYPE: PRT
<213> ORGANISM: Artificial Sequence
<220> FEATURE:
<223> OTHER INFORMATION: Humanized sequence

<400> SEQUENCE: 18

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Ser Phe Asn Ala Tyr
             20                  25                  30

Ala Met Asn Trp Val Arg Gln Ala Pro Gly Lys Gly Leu Glu Trp Val
         35                  40                  45

Gly Arg Ile Arg Thr Lys Asn Asn Asn Tyr Ala Thr Tyr Tyr Ala Asp
     50                  55                  60

Ser Val Lys Asp Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Phe Tyr Gly Asn Gly Val Trp Gly Gln Gly Thr Leu
            100                 105                 110

Val Thr Val Ser Ser
        115

<210> SEQ ID NO 19
<211> LENGTH: 117
<212> TYPE: PRT
<213> ORGANISM: Artificial Sequence
<220> FEATURE:
<223> OTHER INFORMATION: Humanized sequence

<400> SEQUENCE: 19

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Ser Phe Asn Ala Tyr
             20                  25                  30

Ala Met Asn Trp Val Arg Gln Ala Pro Gly Lys Gly Leu Glu Trp Val
         35                  40                  45

Ala Arg Ile Arg Thr Lys Asn Asn Asn Tyr Ala Thr Tyr Tyr Ala Asp
     50                  55                  60

Ser Val Lys Asp Arg Tyr Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Phe Tyr Gly Asn Gly Val Trp Gly Gln Gly Thr Leu
            100                 105                 110

Val Thr Val Ser Ser
        115

<210> SEQ ID NO 20
<211> LENGTH: 117
<212> TYPE: PRT
<213> ORGANISM: Artificial Sequence
<220> FEATURE:
```

```
<223> OTHER INFORMATION: Humanized sequence

<400> SEQUENCE: 20

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Ser Phe Asn Ala Tyr
             20                  25                  30

Ala Met Asn Trp Val Arg Gln Ala Pro Gly Lys Gly Leu Glu Trp Val
         35                  40                  45

Ala Arg Ile Arg Thr Lys Asn Asn Tyr Ala Thr Tyr Tyr Ala Asp
     50                  55                  60

Ser Val Lys Asp Arg Tyr Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                 85                  90                  95

Tyr Cys Val Thr Phe Tyr Gly Asn Gly Val Trp Gly Gln Gly Thr Leu
            100                 105                 110

Val Thr Val Ser Ser
            115

<210> SEQ ID NO 21
<211> LENGTH: 100
<212> TYPE: PRT
<213> ORGANISM: Mus musculus

<400> SEQUENCE: 21

Asp Val Val Met Thr Gln Thr Pro Leu Thr Leu Ser Val Thr Val Gly
 1               5                  10                  15

His Pro Ala Ser Ile Ser Cys Lys Ser Gln Ser Leu Leu Asp Ser
             20                  25                  30

Asp Gly Lys Thr Phe Leu Asn Trp Leu Leu Gln Arg Pro Gly Gln Ser
         35                  40                  45

Pro Lys Arg Leu Ile Tyr Leu Val Ser Lys Leu Asp Ser Gly Val Pro
     50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                 85                  90                  95

Thr His Phe Pro
            100

<210> SEQ ID NO 22
<211> LENGTH: 100
<212> TYPE: PRT
<213> ORGANISM: Mus musculus

<400> SEQUENCE: 22

Asp Val Val Met Thr Gln Thr Pro Leu Thr Leu Ser Val Thr Ile Gly
 1               5                  10                  15

Gln Pro Ala Ser Ile Ser Cys Lys Ser Gln Ser Leu Leu Asp Ser
             20                  25                  30

Asp Gly Lys Thr Tyr Leu Asn Trp Leu Leu Gln Arg Pro Gly Gln Ser
         35                  40                  45

Pro Lys Arg Leu Ile Tyr Leu Val Ser Lys Leu Asp Ser Gly Val Pro
     50                  55                  60

Asp Arg Phe Thr Gly Ser Gly Ser Gly Thr Asp Phe Thr Leu Lys Ile
65                  70                  75                  80
```

Ser Arg Val Glu Ala Glu Asp Leu Gly Val Tyr Tyr Cys Trp Gln Gly
                85                  90                  95

Thr His Phe Pro
            100

<210> SEQ ID NO 23
<211> LENGTH: 100
<212> TYPE: PRT
<213> ORGANISM: Mus musculus

<400> SEQUENCE: 23

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
                20                  25                  30

Asn Gly Lys Thr Tyr Leu Asn Trp Leu Leu Gln Arg Pro Gly Gln Ser
            35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Thr His Phe Pro
            100

<210> SEQ ID NO 24
<211> LENGTH: 100
<212> TYPE: PRT
<213> ORGANISM: Mus musculus
<220> FEATURE:
<221> NAME/KEY: VARIANT
<222> LOCATION: (1)...(100)
<223> OTHER INFORMATION: Xaa = Any Amino Acid

<400> SEQUENCE: 24

Asp Val Val Met Thr Gln Xaa Leu His Ser Leu Ser Val Thr Ile Gly
1               5                   10                  15

Gln Pro Ala Ser Ile Ser Cys Lys Ser Ser Gln Ser Leu Leu Tyr Ser
                20                  25                  30

Asn Gly Lys Thr Tyr Leu Asn Trp Leu Leu Gln Arg Pro Val Gln Pro
            35                  40                  45

Pro Lys Arg Leu Ile Tyr Leu Val Ser Lys Leu Tyr Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Xaa Pro Glu Asp Leu Gly Val Tyr Xaa Cys Met Gln Asp
                85                  90                  95

Thr His Phe Pro
            100

<210> SEQ ID NO 25
<211> LENGTH: 100
<212> TYPE: PRT
<213> ORGANISM: Mus musculus

<400> SEQUENCE: 25

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Tyr Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Thr His Val Pro
            100

<210> SEQ ID NO 26
<211> LENGTH: 100
<212> TYPE: PRT
<213> ORGANISM: Mus musculus

<400> SEQUENCE: 26

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro
            100

<210> SEQ ID NO 27
<211> LENGTH: 100
<212> TYPE: PRT
<213> ORGANISM: Mus musculus

<400> SEQUENCE: 27

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro
            100

<210> SEQ ID NO 28

```
<211> LENGTH: 100
<212> TYPE: PRT
<213> ORGANISM: Mus musculus

<400> SEQUENCE: 28

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro
            100

<210> SEQ ID NO 29
<211> LENGTH: 100
<212> TYPE: PRT
<213> ORGANISM: Mus musculus

<400> SEQUENCE: 29

Asp Ala Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Glu Asn Ser
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Asn Arg Phe Ser Gly Val Leu
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Leu Gln Val
                85                  90                  95

Thr His Val Pro
            100

<210> SEQ ID NO 30
<211> LENGTH: 100
<212> TYPE: PRT
<213> ORGANISM: Mus musculus

<400> SEQUENCE: 30

Asp Val Leu Leu Thr Gln Thr Pro Leu Phe Leu Pro Val Ser Leu Gly
1               5                   10                  15

Asp Gln Ala Ser Ile Ser Cys Ser Ser Ser Gln Ser Leu Val His Ser
            20                  25                  30

Asn Gly Asn Tyr Tyr Leu Glu Trp His Leu Gln Lys Ser Gly Gln Ser
        35                  40                  45

Leu Gln Leu Leu Ile Tyr Glu Val Ser Lys Arg His Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Pro Glu Asp Leu Gly Val Tyr Tyr Cys Phe Gln Gly
                85                  90                  95

Thr His Leu Pro
            100

<210> SEQ ID NO 31
<211> LENGTH: 100
<212> TYPE: PRT
<213> ORGANISM: Mus musculus

<400> SEQUENCE: 31

Asp Ile Val Met Thr Gln Ala Ala Phe Ser Asn Pro Val Thr Leu Gly
 1               5                  10                  15

Thr Ser Ala Ser Ile Ser Cys Arg Ser Ser Lys Ser Leu Leu His Ser
            20                  25                  30

Ser Gly Asn Thr Tyr Leu Tyr Trp Phe Leu Gln Lys Pro Gly Gln Ser
        35                  40                  45

Pro Gln Leu Leu Ile Tyr Tyr Ile Ser Asn Leu Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Met Gln Gly
                85                  90                  95

Leu Glu Tyr Pro
            100

<210> SEQ ID NO 32
<211> LENGTH: 100
<212> TYPE: PRT
<213> ORGANISM: Mus musculus

<400> SEQUENCE: 32

Asp Ile Val Ile Thr Gln Asp Glu Leu Ser Asn Pro Val Thr Ser Gly
 1               5                  10                  15

Glu Ser Val Ser Ile Ser Cys Arg Ser Ser Lys Ser Leu Leu Tyr Lys
            20                  25                  30

Asp Gly Lys Thr Tyr Leu Asn Trp Phe Leu Gln Arg Pro Gly Gln Ser
        35                  40                  45

Pro Gln Leu Leu Ile Tyr Leu Met Ser Thr Arg Ala Ser Gly Val Ser
    50                  55                  60

Asp Arg Phe Ser Gly Ser Gly Ser Gly Thr Asp Phe Thr Leu Glu Ile
65                  70                  75                  80

Ser Arg Val Lys Ala Glu Asp Val Gly Val Tyr Tyr Cys Gln Gln Leu
                85                  90                  95

Val Glu Tyr Pro
            100

<210> SEQ ID NO 33
<211> LENGTH: 100
<212> TYPE: PRT
<213> ORGANISM: Mus musculus

<400> SEQUENCE: 33

Asp Ile Val Met Thr Gln Ala Ala Phe Ser Asn Pro Val Thr Leu Gly
 1               5                  10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
```

-continued

```
                 35                  40                  45
Pro Gln Leu Leu Ile Tyr Gln Met Ser Asn Leu Ala Ser Gly Val Pro
         50                  55                  60

Asp Arg Phe Ser Ser Gly Ser Gly Thr Asp Phe Thr Leu Arg Ile
 65                  70                  75                  80

Ser Arg Val Glu Ala Glu Asp Val Gly Val Tyr Tyr Cys Ala Gln Asn
                 85                  90                  95

Leu Glu Leu Pro
            100
```

<210> SEQ ID NO 34
<211> LENGTH: 101
<212> TYPE: PRT
<213> ORGANISM: Mus musculus

<400> SEQUENCE: 34

```
Glu Val Gln Leu Val Glu Ser Gly Gly Gly Leu Val Gln Pro Lys Gly
  1               5                  10                  15

Ser Leu Lys Leu Ser Cys Ala Ala Ser Gly Phe Ser Phe Asn Ala Tyr
                 20                  25                  30

Ala Met Asn Trp Val Arg Gln Ala Pro Gly Lys Gly Leu Glu Trp Val
             35                  40                  45

Ala Arg Ile Arg Thr Lys Asn Asn Tyr Ala Thr Tyr Tyr Ala Asp
         50                  55                  60

Ser Val Lys Asp Arg Tyr Thr Ile Ser Arg Asp Asp Ser Glu Ser Met
 65                  70                  75                  80

Leu Phe Leu Gln Met Asn Asn Leu Lys Thr Glu Asp Thr Ala Met Tyr
                 85                  90                  95

Tyr Cys Val Thr Phe
            100
```

<210> SEQ ID NO 35
<211> LENGTH: 100
<212> TYPE: PRT
<213> ORGANISM: Mus musculus

<400> SEQUENCE: 35

```
Glu Val Gln Leu Val Glu Val Trp Trp Arg Met Val Gln Pro Lys Gly
  1               5                  10                  15

Ser Leu Lys Leu Ser Cys Ala Ala Ser Gly Phe Thr Phe Asn Thr Tyr
                 20                  25                  30

Ala Met Asn Trp Val Arg Gln Ala Pro Gly Lys Gly Leu Glu Trp Val
             35                  40                  45

Ala Arg Ile Arg Ser Lys Ser Ser Asn Tyr Ala Thr Tyr Tyr Ala Asp
         50                  55                  60

Ser Val Lys Asp Arg Phe Thr Ile Ser Arg Asp Asp Ser Gln Ser Met
 65                  70                  75                  80

Leu Tyr Leu Gln Met Asn Asn Leu Lys Thr Glu Asp Thr Ala Met Tyr
                 85                  90                  95

Tyr Cys Val Ile
            100
```

<210> SEQ ID NO 36
<211> LENGTH: 100
<212> TYPE: PRT
<213> ORGANISM: Mus musculus

<400> SEQUENCE: 36

```
Glu Val Lys Leu Glu Glu Ser Gly Gly Gly Leu Val Gln Pro Gly Gly
 1               5                  10                  15

Ser Met Lys Leu Ser Cys Val Ala Ser Gly Phe Thr Phe Ser Asn Tyr
            20                  25                  30

Trp Met Ser Trp Val Arg Gln Ser Pro Glu Lys Gly Leu Glu Trp Val
            35                  40                  45

Ala Gln Ile Arg Leu Lys Ser Asp Asn Tyr Ala Thr His Tyr Ala Glu
        50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Gly
            100
```

<210> SEQ ID NO 37
<211> LENGTH: 100
<212> TYPE: PRT
<213> ORGANISM: Mus musculus

<400> SEQUENCE: 37

```
Glu Val Lys Leu Val Glu Ser Gly Gly Gly Leu Val Gln Pro Gly Gly
 1               5                  10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
            35                  40                  45

Gly Phe Ile Arg Asn Lys Ala Asn Gly Tyr Thr Thr Glu Tyr Ser Ala
        50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Ala Arg
            100
```

<210> SEQ ID NO 38
<211> LENGTH: 98
<212> TYPE: PRT
<213> ORGANISM: Mus musculus

<400> SEQUENCE: 38

```
Glu Val Lys Leu Val Glu Ser Gly Gly Gly Leu Val Lys Pro Gly Gly
 1               5                  10                  15

Ser Leu Lys Leu Ser Cys Ala Ala Ser Gly Phe Thr Phe Ser Ser Tyr
            20                  25                  30

Thr Met Ser Trp Val Arg Gln Ser Pro Glu Lys Arg Leu Glu Trp Val
            35                  40                  45

Ala Thr Ile Ser Ser Gly Gly Ser Tyr Thr Tyr Tyr Pro Asp Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Thr Arg
```

```
<210> SEQ ID NO 39
<211> LENGTH: 98
<212> TYPE: PRT
<213> ORGANISM: Mus musculus

<400> SEQUENCE: 39

Asp Val Lys Leu Val Glu Ser Gly Gly Gly Leu Val Lys Pro Gly Gly
 1               5                  10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Thr Arg

<210> SEQ ID NO 40
<211> LENGTH: 98
<212> TYPE: PRT
<213> ORGANISM: Mus musculus
<220> FEATURE:
<221> NAME/KEY: VARIANT
<222> LOCATION: (1)...(98)
<223> OTHER INFORMATION: Xaa = Any Amino Acid

<400> SEQUENCE: 40

Glu Leu Gln Leu Val Glu Ser Gly Gly Gly Leu Val Gln Pro Gly Gly
 1               5                  10                  15

Ser Arg Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Ala Ile Ser Thr Asp Gly Ser Phe Ile Tyr Xaa Pro Asp Thr Val
    50                  55                  60

Lys Gly Arg Phe Thr Ile Ser Arg Asp Asn Ala Lys Asn Thr Leu Phe
65                  70                  75                  80

Leu Gln Met Ser Ser Leu Arg Tyr Glu Asp Thr Ala Met Tyr Tyr Cys
                85                  90                  95

Leu Arg

<210> SEQ ID NO 41
<211> LENGTH: 98
<212> TYPE: PRT
<213> ORGANISM: Mus musculus

<400> SEQUENCE: 41

Glu Val Lys Leu Val Glu Ser Gly Gly Gly Leu Val Gln Pro Gly Gly
 1               5                  10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Ser Asn Gly Gly Ser Thr Tyr Tyr Pro Asp Thr Val
    50                  55                  60
```

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Arg

<210> SEQ ID NO 42
<211> LENGTH: 101
<212> TYPE: PRT
<213> ORGANISM: Mus musculus

<400> SEQUENCE: 42

Glu Val Lys Leu Val Glu Ser Gly Gly Gly Leu Val Gln Pro Gly Ala
1               5                   10                  15

Ser Leu Arg Leu Ser Cys Ala Ser Ser Gly Phe Thr Phe Thr Asp Tyr
                20                  25                  30

Tyr Met Asn Trp Val His Arg Pro Pro Gly Lys Pro Leu Glu Trp Leu
            35                  40                  45

Ala Leu Ile Arg Asn Lys Ala Asn Gly Tyr Ile Thr Glu Tyr Ser Ala
        50                  55                  60

Ser Met Lys Gly Arg Phe Thr Ile Ser Arg Asp Asn Ser Gln Ser Ile
65                  70                  75                  80

Leu Tyr Leu Gln Met Asn Thr Leu Ser Thr Glu Asp Ser Ala Thr Tyr
                85                  90                  95

Tyr Cys Ala Arg Asp
            100

<210> SEQ ID NO 43
<211> LENGTH: 100
<212> TYPE: PRT
<213> ORGANISM: Mus musculus

<400> SEQUENCE: 43

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Asp Phe
                20                  25                  30

Tyr Met Glu Trp Val Arg Gln Pro Pro Gly Lys Arg Leu Glu Trp Ile
            35                  40                  45

Ala Ala Ser Arg Asn Lys Ala Asn Asp Tyr Thr Thr Glu Tyr Ser Ala
        50                  55                  60

Ser Val Lys Gly Arg Phe Ile Val Ser Arg Asp Thr Ser Gln Ser Ile
65                  70                  75                  80

Leu Tyr Leu Gln Met Asn Ala Leu Arg Ala Glu Asp Thr Ala Ile Tyr
                85                  90                  95

Tyr Cys Ala Arg
            100

<210> SEQ ID NO 44
<211> LENGTH: 98
<212> TYPE: PRT
<213> ORGANISM: Mus musculus

<400> SEQUENCE: 44

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr

```
                    20                  25                  30

Thr Met Ser Trp Val Arg Gln Thr Pro Glu Lys Arg Leu Glu Trp Val
            35                  40                  45

Ala Thr Ile Ser Ser Gly Gly Asn Thr Tyr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Arg Ser Glu Asp Thr Ala Leu Tyr Tyr Cys
                85                  90                  95

Ala Arg

<210> SEQ ID NO 45
<211> LENGTH: 98
<212> TYPE: PRT
<213> ORGANISM: Mus musculus

<400> SEQUENCE: 45

Glu Val Lys Leu Val Glu Ser Gly Gly Leu Val Lys Pro Gly Gly
1               5                   10                  15

Ser Leu Lys Leu Ser Cys Ala Thr Ser Gly Phe Thr Phe Ser Ser Tyr
                20                  25                  30

Gly Met Ser Trp Val Arg Gln Thr Pro Glu Lys Arg Leu Glu Trp Val
            35                  40                  45

Ala Thr Ile Ser Gly Gly Ser Tyr Thr Tyr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Arg Ser Glu Asp Thr Ala Leu Tyr Tyr Cys
                85                  90                  95

Ala Arg

<210> SEQ ID NO 46
<211> LENGTH: 101
<212> TYPE: PRT
<213> ORGANISM: Mus musculus

<400> SEQUENCE: 46

Glu Val Lys Leu Met Glu Ser Gly Gly Gly Leu Val Gln Pro Gly Ala
1               5                   10                  15

Ser Leu Arg Leu Ser Cys Glu Ala Ser Gly Phe Thr Phe Thr Asp Tyr
                20                  25                  30

Tyr Met Ser Trp Val Arg Gln Leu Pro Arg Lys Ser Pro Glu Trp Leu
            35                  40                  45

Ala Leu Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Asn Ile
65                  70                  75                  80

Leu Tyr Leu Gln Met Asn Thr Leu Arg Ala Glu Ala Ser Ala Thr Tyr
                85                  90                  95

Tyr Cys Ala Lys Asp
                100

<210> SEQ ID NO 47
<211> LENGTH: 98
<212> TYPE: PRT
<213> ORGANISM: Mus musculus
```

-continued

```
<400> SEQUENCE: 47

Glu Val Lys Leu Leu Glu Ser Gly Gly Leu Val Gln Pro Gly Gly
 1               5                  10                  15

Ser Leu Lys Leu Ser Cys Ala Ala Ser Gly Phe Asp Phe Ser Arg Tyr
                20                  25                  30

Trp Met Ser Trp Val Arg Gln Ala Pro Gly Lys Gly Leu Glu Trp Ile
         35                  40                  45

Gly Glu Ile Asn Pro Asp Ser Ser Thr Ile Asn Tyr Thr Pro Ser Leu
     50                  55                  60

Lys Asp Lys Phe Ile Ile Ser Arg Asp Asn Ala Lys Asn Thr Leu Tyr
 65                  70                  75                  80

Leu Gln Met Ser Lys Val Arg Ser Glu Asp Thr Ala Leu Tyr Tyr Cys
                 85                  90                  95

Ala Arg

<210> SEQ ID NO 48
<211> LENGTH: 89
<212> TYPE: PRT
<213> ORGANISM: Mus musculus

<400> SEQUENCE: 48

Gly Leu Val Gln Pro Gly Gly Ser Leu Lys Leu Ser Cys Ala Ala Ser
 1               5                  10                  15

Gly Phe Thr Phe Ser Ser Tyr Gly Met Ser Trp Val Arg Gln Thr Pro
                20                  25                  30

Asp Lys Arg Leu Glu Leu Val Ala Thr Ile Asn Ser Asn Gly Gly Ser
             35                  40                  45

Thr Tyr Tyr Pro Asp Ser Val Lys Gly Arg Phe Thr Ile Ser Arg Asp
     50                  55                  60

Asn Ala Lys Asn Thr Leu Tyr Leu Gln Met Ser Ser Leu Lys Ser Glu
 65                  70                  75                  80

Asp Thr Ala Met Tyr Tyr Cys Ala Arg
                 85

<210> SEQ ID NO 49
<211> LENGTH: 89
<212> TYPE: PRT
<213> ORGANISM: Mus musculus

<400> SEQUENCE: 49

Gly Leu Val Lys Pro Gly Gly Ser Leu Lys Leu Ser Cys Ala Ala Ser
 1               5                  10                  15

Gly Phe Thr Phe Ser Ser Tyr Ala Met Ser Trp Val Arg Gln Thr Pro
                20                  25                  30

Glu Lys Arg Leu Glu Trp Val Ala Thr Ile Ser Ser Gly Gly Ser Tyr
             35                  40                  45

Thr Tyr Tyr Pro Asp Ser Val Lys Gly Arg Phe Thr Ile Ser Arg Asp
     50                  55                  60

Asn Ala Lys Asn Thr Leu Tyr Leu Gln Met Ser Ser Leu Arg Ser Glu
 65                  70                  75                  80

Asp Thr Ala Met Tyr Tyr Cys Ala Arg
                 85

<210> SEQ ID NO 50
<211> LENGTH: 89
<212> TYPE: PRT
<213> ORGANISM: Mus musculus
```

<400> SEQUENCE: 50

Gly Leu Val Gln Pro Gly Gly Ser Arg Lys Leu Ser Cys Ala Ala Ser
1               5                   10                  15

Gly Phe Thr Phe Ser Ser Phe Gly Met His Trp Val Arg Gln Ala Pro
            20                  25                  30

Glu Lys Gly Leu Glu Trp Val Ala Tyr Ile Ser Ser Gly Ser Ser Thr
        35                  40                  45

Ile Tyr Tyr Ala Asp Thr Val Lys Gly Arg Phe Thr Ile Ser Arg Asp
    50                  55                  60

Asn Pro Lys Asn Thr Leu Phe Leu Gln Met Thr Ser Leu Arg Ser Glu
65                  70                  75                  80

Asp Thr Ala Met Tyr Tyr Cys Ala Arg
                85

<210> SEQ ID NO 51
<211> LENGTH: 88
<212> TYPE: PRT
<213> ORGANISM: Mus musculus

<400> SEQUENCE: 51

Gly Leu Val Lys Pro Gly Gly Ser Leu Lys Leu Ser Cys Ala Ala Ser
1               5                   10                  15

Gly Phe Thr Phe Ser Ser Tyr Ala Met Ser Trp Val Arg Gln Thr Pro
            20                  25                  30

Glu Lys Arg Leu Glu Trp Val Ala Ser Ile Ser Ser Gly Gly Ser Thr
        35                  40                  45

Tyr Tyr Pro Asp Ser Val Lys Gly Arg Phe Thr Ile Ser Arg Asp Asn
    50                  55                  60

Ala Arg Asn Ile Leu Tyr Leu Gln Met Ser Ser Leu Arg Ser Glu Asp
65                  70                  75                  80

Thr Ala Met Tyr Tyr Cys Ala Arg
                85

<210> SEQ ID NO 52
<211> LENGTH: 98
<212> TYPE: PRT
<213> ORGANISM: Mus musculus

<400> SEQUENCE: 52

Glu Val Lys Leu Leu Glu Ser Gly Gly Gly Leu Val Gln Pro Gly Gly
1               5                   10                  15

Ser Leu Asn Leu Ser Cys Ala Ala Ser Gly Phe Asp Phe Ser Arg Tyr
            20                  25                  30

Trp Met Ser Trp Ala Arg Gln Ala Pro Gly Lys Gly Gln Glu Trp Ile
        35                  40                  45

Gly Glu Ile Asn Pro Gly Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Arg

<210> SEQ ID NO 53
<211> LENGTH: 87
<212> TYPE: PRT

```
<213> ORGANISM: Mus musculus

<400> SEQUENCE: 53

Val Lys Pro Gly Gly Ser Leu Lys Leu Ser Cys Ala Ala Ser Gly Phe
 1               5                  10                  15

Thr Phe Ser Ser Tyr Thr Met Ser Trp Val Arg Gln Thr Pro Glu Lys
            20                  25                  30

Arg Leu Glu Trp Val Ala Tyr Ile Ser Asn Gly Gly Gly Ser Thr Tyr
        35                  40                  45

Tyr Pro Asp Thr Val Lys Gly Arg Phe Thr Ile Ser Arg Asp Asn Ala
    50                  55                  60

Lys Asn Thr Leu Tyr Leu Gln Met Ser Ser Leu Lys Ser Glu Asp Thr
65                  70                  75                  80

Ala Met Tyr Tyr Cys Ala Arg
                85

<210> SEQ ID NO 54
<211> LENGTH: 112
<212> TYPE: PRT
<213> ORGANISM: Homo sapiens

<400> SEQUENCE: 54

Asp Ile Gln Leu Thr Gln Ser Pro Leu Thr Leu Ser Val Thr Ile Gly
 1               5                  10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Asp Asp Leu Gly Val Tyr Tyr Cys Trp Gln Gly
                85                  90                  95

Thr His Phe Pro Gln Thr Phe Gly Gly Gly Thr Lys Leu Glu Ile Lys
                100                 105                 110

<210> SEQ ID NO 55
<211> LENGTH: 112
<212> TYPE: PRT
<213> ORGANISM: Homo sapiens

<400> SEQUENCE: 55

Asp Val Val Leu Thr Gln Ser Pro Leu Ser Leu Pro Val Thr Leu Gly
 1               5                  10                  15

Gln Pro Ala Ser Ile Ser Cys Arg Ser Asp Gln Ser Leu Val Tyr Ser
            20                  25                  30

Asp Gly Lys Thr Tyr Leu Asn Trp Tyr Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Thr Gly Ser Gly Ser Gly Thr Asp Phe Thr Leu Glu Ile
65                  70                  75                  80

Ser Arg Val Glu Ala Glu Asp Val Gly Val Tyr Tyr Cys Met Gln Gly
                85                  90                  95

Thr His Trp Pro Gly Thr Phe Gly Gln Gly Thr Lys Val Glu Ile Lys
                100                 105                 110
```

<210> SEQ ID NO 56
<211> LENGTH: 112
<212> TYPE: PRT
<213> ORGANISM: Homo sapiens

<400> SEQUENCE: 56

```
Asp Val Val Met Thr Gln Ser Pro Leu Ser Leu Pro Val Thr Leu Gly
  1               5                  10                  15

Gln Pro Ala Ser Ile Ser Cys Arg Ser Ser Gln Ser Leu Val Tyr Ser
             20                  25                  30

Asp Gly Asn Thr Tyr Leu Asn Trp Phe Gln Gln Arg Pro Gly Gln Ser
         35                  40                  45

Pro Arg Arg Leu Ile Tyr Lys Val Ser Asn Arg Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Ser Trp Thr Phe Gly Gln Gly Thr Lys Val Glu Ile Lys
            100                 105                 110
```

<210> SEQ ID NO 57
<211> LENGTH: 112
<212> TYPE: PRT
<213> ORGANISM: Homo sapiens

<400> SEQUENCE: 57

```
Asp Val Val Val Thr Gln Ser Pro Leu Ser Leu Pro Val Thr Leu Gly
  1               5                  10                  15

Gln Pro Ala Ser Ile Ser Cys Arg Ser Ser Leu Ser Leu Val Asp Ser
             20                  25                  30

Asp Gly Asn Thr Tyr Leu Asn Trp Phe Leu Gln Arg Pro Gly Gln Ser
         35                  40                  45

Pro Arg Arg Leu Ile Tyr Gln Leu Ser Ser Arg Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro Ile Thr Phe Gly Gln Gly Thr Arg Leu Glu Ile Lys
            100                 105                 110
```

<210> SEQ ID NO 58
<211> LENGTH: 112
<212> TYPE: PRT
<213> ORGANISM: Homo sapiens

<400> SEQUENCE: 58

```
Asp Ile Val Met Thr Gln Ser Pro Leu Ser Leu Pro Val Thr Leu Gly
  1               5                  10                  15

Gln Pro Ala Ser Ile Ser Cys Arg Ser Ser Gln Gly Leu Val Tyr Ser
             20                  25                  30

Asp Gly Asp Thr Tyr Leu Asn Trp Phe Gln Gln Arg Pro Gly Gln Ser
         35                  40                  45

Pro Arg Arg Leu Ile Tyr Lys Val Ser Asn Arg Asp Ser Gly Val Pro
     50                  55                  60
```

-continued

Asp Arg Phe Ser Gly Gly Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110

<210> SEQ ID NO 59
<211> LENGTH: 111
<212> TYPE: PRT
<213> ORGANISM: Homo sapiens

<400> SEQUENCE: 59

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Phe Thr Phe Gly Gly Gly Thr Arg Leu Glu Ile
            100                 105                 110

<210> SEQ ID NO 60
<211> LENGTH: 112
<212> TYPE: PRT
<213> ORGANISM: Homo sapiens

<400> SEQUENCE: 60

Ala Glu Glu Leu Thr Gln Ser Pro Leu Ser Leu Pro Val Thr Leu Gly
1               5                   10                  15

Gln Pro Ala Ser Ile Ser Cys Arg Ser Ser Gln Ser Leu Leu Leu Ser
            20                  25                  30

Asp Gly Asp Thr Tyr Leu Asn Trp Tyr Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ala His Trp Pro Tyr Thr Phe Gly Gln Gly Thr Lys Leu Glu Ile Lys
            100                 105                 110

<210> SEQ ID NO 61
<211> LENGTH: 112
<212> TYPE: PRT
<213> ORGANISM: Homo sapiens

<400> SEQUENCE: 61

Asp Val Val Leu Thr Gln Ser Pro Leu Ser Leu Ser Val Thr Leu Gly
1               5                   10                  15

Gln Pro Ala Ser Ile Ser Cys Arg Ser Thr Gln Ile Leu Val Phe Ser

```
                20                  25                  30

Asp Gly Asn Thr Tyr Leu Asn Trp Phe Gln Gln Thr Pro Gly His Ser
            35                  40                  45

Pro Arg Arg Leu Ile Tyr Arg Val Ser Asn Arg Asp Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110

<210> SEQ ID NO 62
<211> LENGTH: 112
<212> TYPE: PRT
<213> ORGANISM: Homo sapiens

<400> SEQUENCE: 62

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Phe Ser
            20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Val Ser Asn Arg Asp Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Ile Tyr Tyr Cys Met Gln Gly
                85                  90                  95

Ala His Trp Pro Leu Thr Phe Gly Gly Gly Thr Lys Val Glu Ile Thr
            100                 105                 110

<210> SEQ ID NO 63
<211> LENGTH: 113
<212> TYPE: PRT
<213> ORGANISM: Homo sapiens

<400> SEQUENCE: 63

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
            35                  40                  45

Pro Arg Arg Leu Ile Tyr Arg Val Ser Asn Arg Asp Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Leu Tyr Tyr Cys Met Gln His
                85                  90                  95

Thr His Trp Ser Pro Ile Thr Phe Gly Gln Gly Thr Arg Leu Glu Ile
            100                 105                 110

Lys

<210> SEQ ID NO 64
```

-continued

```
<211> LENGTH: 113
<212> TYPE: PRT
<213> ORGANISM: Homo sapiens

<400> SEQUENCE: 64

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Val Gln Leu Pro Arg Phe Thr Phe Gly Pro Gly Thr Lys Val Asp Ile
            100                 105                 110

Lys

<210> SEQ ID NO 65
<211> LENGTH: 113
<212> TYPE: PRT
<213> ORGANISM: Homo sapiens

<400> SEQUENCE: 65

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro Arg Phe Thr Phe Gly Pro Gly Thr Lys Val Asp Ile
            100                 105                 110

Lys

<210> SEQ ID NO 66
<211> LENGTH: 112
<212> TYPE: PRT
<213> ORGANISM: Homo sapiens

<400> SEQUENCE: 66

Ala Glu Glu Leu Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60
```

-continued

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Lys Thr Phe Gly Gln Gly Thr Lys Val Glu Ile Lys
            100                 105                 110

<210> SEQ ID NO 67
<211> LENGTH: 112
<212> TYPE: PRT
<213> ORGANISM: Homo sapiens

<400> SEQUENCE: 67

Asp Val Val Met Thr Gln Ser Pro Leu Ser Leu Pro Val Thr Leu Gly
1               5                   10                  15

Gln Ser Ala Ser Ile Ser Cys Thr Ser Ser Gln Ser Leu Val Tyr Thr
            20                  25                  30

Asp Gly Lys Ile Tyr Leu Asn Trp Phe Gln Gln Arg Pro Gly Gln Ser
        35                  40                  45

Pro Arg Arg Leu Ile Phe Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Ala Ile Tyr Tyr Cys Met Gln Gly
                85                  90                  95

Thr His Trp Pro Gly Thr Phe Gly Gln Gly Thr Lys Val Glu Ile Lys
            100                 105                 110

<210> SEQ ID NO 68
<211> LENGTH: 113
<212> TYPE: PRT
<213> ORGANISM: Homo sapiens

<400> SEQUENCE: 68

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Gly Asp Gly Asn Thr Tyr Leu Asn Trp Tyr Leu Gln Lys Ala Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Gln Ala Glu Asp Val Gly Val Tyr Tyr Cys Met Gln
                85                  90                  95

Arg Leu Glu Ile Pro Tyr Thr Phe Gly Gln Gly Thr Lys Leu Glu Ile
            100                 105                 110

Arg

<210> SEQ ID NO 69
<211> LENGTH: 112
<212> TYPE: PRT
<213> ORGANISM: Homo sapiens

<400> SEQUENCE: 69

Asp Ile Val Met Thr Gln Thr Pro Leu Ser Leu Pro Val Thr Leu Gly

```
            1               5                  10                 15
Gln Pro Ala Ser Ile Ser Cys Arg Ser Ser Arg Gly Leu Val His Ser
                    20                  25                 30

Asp Gly Asn Thr Tyr Leu Asn Trp Phe Gln Gln Arg Pro Gly Gln Ser
                35                  40                  45

Pro Arg Arg Leu Ile Tyr Lys Val Ser Asn Arg Asp Ser Gly Val Pro
            50                  55                  60

Asp Arg Phe Ser Gly Ser Gly Ser Gly Ala Asp Phe Thr Leu Lys Ile
65                  70                  75                  80

Ser Arg Val Glu Ala Glu Asp Val Gly Val Tyr Tyr Cys Met Gln Ser
                    85                  90                  95

Ile His Trp Pro Trp Thr Phe Gly Gln Gly Thr Lys Val Glu Ile Lys
                100                 105                 110
```

<210> SEQ ID NO 70
<211> LENGTH: 112
<212> TYPE: PRT
<213> ORGANISM: Homo sapiens

<400> SEQUENCE: 70

```
            1               5                  10                 15
Asp Ile Val Leu Thr Gln Ser Pro Leu Ser Leu Pro Val Thr Leu Gly
1                   5                   10                  15

Gln Pro Ala Ser Ile Ser Cys Arg Ser Ser Gln Asn Leu Val Tyr Ser
                    20                  25                  30

Asp Gly Asn Thr Tyr Leu Asn Trp Phe Gln Gln Arg Pro Gly Gln Ser
                35                  40                  45

Pro Arg Arg Leu Ile Tyr Lys Val Ser Asn Arg Asp Ser Gly Val Pro
            50                  55                  60

Asp Ser Phe Ser Gly Ser Gly Ser Gly Thr Asp Phe Thr Leu Thr Ile
65                  70                  75                  80

Ser Arg Val Glu Ala Glu Asp Val Gly Ile Tyr Tyr Cys Met Gln Gly
                    85                  90                  95

Thr Arg Trp Pro Tyr Thr Phe Gly Glu Gly Thr Lys Leu Glu Ile Lys
                100                 105                 110
```

<210> SEQ ID NO 71
<211> LENGTH: 127
<212> TYPE: PRT
<213> ORGANISM: Homo sapiens

<400> SEQUENCE: 71

```
Glu Val Gln Leu Val Glu Ser Gly Gly Gly Leu Val Gln Pro Gly Gly
1                   5                   10                  15

Ser Leu Lys Leu Ser Cys Ala Ala Ser Gly Phe Thr Phe Ser Gly Ser
                    20                  25                  30

Thr Met His Trp Val Arg Gln Ala Ser Gly Lys Gly Leu Glu Trp Val
                35                  40                  45

Gly Arg Ile Arg Asn Lys Asp Asn Ser Tyr Ala Thr Ala Tyr Ala Ala
            50                  55                  60

Ser Val Lys Gly Arg Phe Thr Ile Ser Arg Asp Asp Ser Glu Asn Thr
65                  70                  75                  80

Ala Tyr Leu Gln Met Asn Ser Leu Lys Ile Glu Asp Thr Ala Val Tyr
                    85                  90                  95

Tyr Cys Thr Arg Gly Ser Ser Met Val Arg Gly Val Asn Gly Tyr Tyr
                100                 105                 110

Gly Met Asp Val Trp Gly Gln Gly Thr Thr Val Thr Val Ser Ser
```

115             120             125

<210> SEQ ID NO 72
<211> LENGTH: 126
<212> TYPE: PRT
<213> ORGANISM: Homo sapiens

<400> SEQUENCE: 72

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ile Phe Ser Asp Tyr
            20                  25                  30

Tyr Met Asp Trp Val Arg Gln Ala Pro Ala Lys Gly Leu Glu Trp Leu
        35                  40                  45

Ala Arg Thr Arg Asn Lys Ala Asn Ser Tyr Thr Thr Glu Tyr Ala Ala
    50                  55                  60

Ser Val Lys Gly Arg Phe Thr Ile Ser Arg Asp Asp Ser Met Asn Ser
65                  70                  75                  80

Leu Ser Leu Gln Met Asn Ser Leu Lys Thr Glu Asp Thr Ala Ile Tyr
                85                  90                  95

Tyr Cys Val Cys Val Arg Thr Asp Cys Ser Ser Thr Arg Cys His Gly
            100                 105                 110

Met Asp Val Trp Gly Gln Gly Thr Thr Val Thr Val Ser Ser
        115                 120                 125

<210> SEQ ID NO 73
<211> LENGTH: 126
<212> TYPE: PRT
<213> ORGANISM: Homo sapiens

<400> SEQUENCE: 73

Glu Val Gln Leu Val Asp Ser Gly Gly Gly Leu Val Gln Pro Gly Gly
 1               5                  10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Ile Arg Asn Lys Ala Asn Ser Tyr Thr Thr Glu Tyr Ala Ala
    50                  55                  60

Ser Leu Lys Gly Arg Phe Thr Ile Ser Arg Asp Asp Ser Glu Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Ala Glu Thr Asp Arg Gly Tyr Tyr Tyr His Gly
            100                 105                 110

Met Asp Val Trp Gly Gln Gly Thr Thr Val Thr Val Ser Ser
        115                 120                 125

<210> SEQ ID NO 74
<211> LENGTH: 126
<212> TYPE: PRT
<213> ORGANISM: Homo sapiens

<400> SEQUENCE: 74

Glu Val Gln Leu Val Glu Ser Gly Gly Gly Leu Val Gln Pro Gly Gly
 1               5                  10                  15

Ser Leu Lys Val Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
         35                  40                  45

Gly Arg Ile Arg Ser Lys Ala Asn Ser Tyr Ala Thr Ala Tyr Ala Ala
     50                  55                  60

Ser Val Lys Gly Arg Phe Thr Ile Ser Arg Asp Asp Ser Lys Asn Thr
 65                  70                  75                  80

Ala Tyr Leu Gln Met Asn Ser Leu Lys Thr Glu Asp Thr Ala Val Tyr
                 85                  90                  95

Tyr Cys Thr Arg Trp Val Leu Gly Arg Gly Ser Glu Gly His Tyr Tyr
             100                 105                 110

Phe Asp Tyr Trp Gly Gln Gly Thr Leu Val Thr Val Ser Ser
         115                 120                 125

<210> SEQ ID NO 75
<211> LENGTH: 115
<212> TYPE: PRT
<213> ORGANISM: Homo sapiens

<400> SEQUENCE: 75

Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Thr Phe Ser Gly Ser
             20                  25                  30

Ala Ile His Trp Val Arg Gln Ala Ser Gly Lys Gly Leu Glu Trp Val
         35                  40                  45

Gly His Ile Arg Asn Lys Pro Asn Asn Tyr Ala Thr Ala Tyr Ala Ala
     50                  55                  60

Ser Val Lys Gly Arg Phe Thr Ile Ser Arg Asp Asp Ser Lys Asn Thr
 65                  70                  75                  80

Ala Tyr Leu Gln Met Asn Ser Leu Lys Thr Glu Asp Thr Ala Val Tyr
                 85                  90                  95

Tyr Cys Ala Ser Gly Ser Tyr Leu Lys Gly Gln Gly Thr Leu Val Thr
             100                 105                 110

Val Ser Ser
         115

<210> SEQ ID NO 76
<211> LENGTH: 125
<212> TYPE: PRT
<213> ORGANISM: Homo sapiens

<400> SEQUENCE: 76

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ile Glu Asp Thr Ala Met Phe Pro Tyr Tyr Tyr Gly Met
             100                 105                 110

```
Asp Val Trp Gly Gln Gly Thr Thr Val Thr Val Ser Ser
        115                 120                 125

<210> SEQ ID NO 77
<211> LENGTH: 128
<212> TYPE: PRT
<213> ORGANISM: Homo sapiens
<220> FEATURE:
<221> NAME/KEY: VARIANT
<222> LOCATION: (1)...(128)
<223> OTHER INFORMATION: Xaa = Any Amino Acid

<400> SEQUENCE: 77

Glu Val Gln Leu Leu Glu Ser Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Arg Asn Tyr Asp Phe Trp Ser Gly Xaa Tyr Tyr Tyr
            100                 105                 110

Tyr Gly Met Asp Val Trp Gly Gln Gly Thr Thr Val Thr Val Ser Ser
        115                 120                 125

<210> SEQ ID NO 78
<211> LENGTH: 128
<212> TYPE: PRT
<213> ORGANISM: Homo sapiens
<220> FEATURE:
<221> NAME/KEY: VARIANT
<222> LOCATION: (1)...(128)
<223> OTHER INFORMATION: Xaa = Any Amino Acid

<400> SEQUENCE: 78

Glu Val Gln Leu Val Glu Ser Gly Gly Gly Leu Val Gln Pro Gly Gly
  1               5                  10                  15

Ser Gln Arg Leu Ser Cys Ala Ala Ser Gly Phe Thr Phe Asn Asn Tyr
             20                  25                  30

Val Met Ser Trp Val Arg Gln Ala Pro Gly Lys Gly Leu Glu Trp Val
         35                  40                  45

Ser Val Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Lys Gly Arg Val Cys Ser Gly Gly Arg Cys Tyr Pro Xaa Tyr Tyr
            100                 105                 110

Tyr Tyr Met Asp Val Trp Gly Lys Gly Thr Thr Val Thr Val Ser Ser
        115                 120                 125

<210> SEQ ID NO 79
<211> LENGTH: 128
```

```
<212> TYPE: PRT
<213> ORGANISM: Homo sapiens
<220> FEATURE:
<221> NAME/KEY: VARIANT
<222> LOCATION: (1)...(128)
<223> OTHER INFORMATION: Xaa = Any Amino Acid

<400> SEQUENCE: 79
```

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Arg Asn Tyr Asp Phe Trp Ser Gly Xaa Tyr Tyr Tyr
            100                 105                 110

Tyr Gly Met Asp Val Trp Gly Gln Gly Thr Thr Val Thr Val Ser Ser
        115                 120                 125

```
<210> SEQ ID NO 80
<211> LENGTH: 116
<212> TYPE: PRT
<213> ORGANISM: Homo sapiens

<400> SEQUENCE: 80
```

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Lys Gly Ser Gly Trp Tyr Trp Gly Gln Gly Thr Leu Val
            100                 105                 110

Thr Val Ser Ser
        115

```
<210> SEQ ID NO 81
<211> LENGTH: 124
<212> TYPE: PRT
<213> ORGANISM: Homo sapiens

<400> SEQUENCE: 81
```

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

-continued

Ala Met Ser Trp Val Arg Gln Ala Pro Gly Lys Gly Leu Glu Trp Val
            35                  40                  45

Ser Gly Ile Ser Gly Ser Gly Gly Ser Thr Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Asp Tyr Tyr Gly Ser Gly Arg Tyr Phe Thr Tyr Ala Thr Asp
                100                 105                 110

Val Trp Gly Gln Gly Thr Thr Val Thr Val Ser Ser
                115                 120

<210> SEQ ID NO 82
<211> LENGTH: 123
<212> TYPE: PRT
<213> ORGANISM: Homo sapiens

<400> SEQUENCE: 82

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Tyr Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Lys Pro Gly Asp Tyr Gly Ser Gly Ser Tyr Tyr Leu Asp Tyr
                100                 105                 110

Trp Gly Gln Gly Thr Leu Val Thr Val Ser Ser
                115                 120

<210> SEQ ID NO 83
<211> LENGTH: 117
<212> TYPE: PRT
<213> ORGANISM: Homo sapiens

<400> SEQUENCE: 83

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Thr Glu Asp Thr Ala Val Tyr Tyr Cys
                85                  90                  95

Thr Thr Tyr Tyr Gly Asp Gly Met Asp Val Trp Gly Lys Gly Thr Met
                100                 105                 110

-continued

Ile Thr Val Ser Ser
        115

<210> SEQ ID NO 84
<211> LENGTH: 125
<212> TYPE: PRT
<213> ORGANISM: Homo sapiens

<400> SEQUENCE: 84

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Val Val Arg Gly Val Ile Ser Tyr Tyr Tyr Gly Met
            100                 105                 110

Asp Val Trp Gly Gln Gly Thr Thr Val Thr Val Ser Ser
        115                 120                 125

<210> SEQ ID NO 85
<211> LENGTH: 120
<212> TYPE: PRT
<213> ORGANISM: Homo sapiens

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Asp Val Val Pro Ala Ala Asp Tyr Trp Gly Gln
            100                 105                 110

Gly Thr Leu Val Thr Val Ser Ser
        115                 120

<210> SEQ ID NO 86
<211> LENGTH: 128
<212> TYPE: PRT
<213> ORGANISM: Homo sapiens

<400> SEQUENCE: 86

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Ser Thr Gly

```
                20                  25                  30
Trp Met Ser Trp Val Arg Gln Ala Pro Gly Lys Gly Leu Glu Trp Val
            35                  40                  45
Gly Arg Ile Lys Ser Lys Thr Asp Gly Thr Ile Asp Tyr Ala Glu
 50                  55                  60
Pro Val Lys Gly Arg Phe Thr Ile Ser Arg Asp Asp Ser Lys Asn Thr
 65                  70                  75                  80
Leu Phe Leu Gln Met Asn Ser Leu Lys Thr Glu Asp Thr Ala Val Tyr
                85                  90                  95
Tyr Cys Thr Thr Ala Leu Thr Arg Tyr Phe Phe Asp Ser Ser Gly Tyr
            100                 105                 110
Pro His Phe Asp His Trp Gly His Gly Thr Leu Val Thr Val Ser Ser
            115                 120                 125
```

<210> SEQ ID NO 87
<211> LENGTH: 127
<212> TYPE: PRT
<213> ORGANISM: Homo sapiens

<400> SEQUENCE: 87

```
Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Ser Ser Tyr
                20                  25                  30
Ala Met Ser Trp Val Arg Gln Ala Pro Gly Lys Gly Leu Glu Trp Val
            35                  40                  45
Ser Ala Ile Ser Gly Ser Asp Gly Ser Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                85                  90                  95
Ala Lys Asp Arg Thr Pro Arg Asn Ile Val Ala Thr Lys Gly Met Asp
            100                 105                 110
Ala Phe Asp Ile Trp Gly Gln Gly Thr Met Val Thr Val Ser Ser
            115                 120                 125
```

<210> SEQ ID NO 88
<211> LENGTH: 119
<212> TYPE: PRT
<213> ORGANISM: Homo sapiens

<400> SEQUENCE: 88

```
Glu Val Gln Leu Val Glu Ser Gly Gly Gly Leu Val Gln Pro Gly Arg
 1               5                  10                  15
Ser Leu Arg Leu Ser Cys Ala Ala Ser Gly Phe Thr Phe Asp Asp Tyr
                20                  25                  30
Ala Met His Trp Val Arg Gln Ala Pro Gly Lys Gly Leu Glu Trp Val
            35                  40                  45
Ser Gly Ile Ser Trp Asn Ser Gly Ser Ile Gly Tyr Ala Asp Ser Val
 50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Leu Tyr Tyr Cys
                85                  90                  95
Ala Thr His Tyr Tyr Tyr Tyr Gly Met Asp Val Trp Gly Gln Gly
```

-continued

```
                    100                 105                 110

Thr Thr Val Thr Val Ser Ser
            115

<210> SEQ ID NO 89
<211> LENGTH: 124
<212> TYPE: PRT
<213> ORGANISM: Homo sapiens

<400> SEQUENCE: 89

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val His Gln Ala Pro Gly Lys Gly Leu Glu Trp Val
        35                  40                  45

Ala Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Trp Gly Leu Arg Gly Glu Gly Asp Tyr Tyr Met Asp
            100                 105                 110

Val Trp Gly Lys Gly Thr Met Val Thr Val Ser Ser
        115                 120

<210> SEQ ID NO 90
<211> LENGTH: 124
<212> TYPE: PRT
<213> ORGANISM: Homo sapiens

<400> SEQUENCE: 90

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro His Thr Phe Gly Gly Val Ile Val Ile Ser Asp
            100                 105                 110

Tyr Trp Gly Gln Gly Thr Leu Val Thr Val Ser Ser
        115                 120

<210> SEQ ID NO 91
<211> LENGTH: 123
<212> TYPE: PRT
<213> ORGANISM: Homo sapiens

<400> SEQUENCE: 91

Glu Val Gln Leu Val Glu Ser Gly Gly Gly Leu Val Lys Pro Arg Gly
1               5                   10                  15
```

```
Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Ala Ser Tyr Ser Tyr Gly Arg Gly Cys Phe Asp Tyr
            100                 105                 110

Trp Gly Gln Gly Thr Leu Val Thr Val Ser Ser
            115                 120

<210> SEQ ID NO 92
<211> LENGTH: 121
<212> TYPE: PRT
<213> ORGANISM: Homo sapiens

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Ser Trp Gly Asp Leu Glu Gly Leu Asp Tyr Trp Gly
            100                 105                 110

Gln Gly Thr Leu Val Thr Val Ser Ser
            115                 120

<210> SEQ ID NO 93
<211> LENGTH: 119
<212> TYPE: PRT
<213> ORGANISM: Homo sapiens

<400> SEQUENCE: 93

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95
```

Tyr Cys Thr Thr Asp Ser Leu Pro Pro His Arg Val Trp Gly Gln Gly
            100                 105                 110

Thr Leu Val Thr Val Ser Ser
        115

<210> SEQ ID NO 94
<211> LENGTH: 123
<212> TYPE: PRT
<213> ORGANISM: Homo sapiens

<400> SEQUENCE: 94

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Ser Ile Pro Gly Ile Ala Val Ala Gly Thr Asp Tyr
            100                 105                 110

Trp Gly Gln Gly Thr Leu Val Thr Val Ser Ser
        115                 120

<210> SEQ ID NO 95
<211> LENGTH: 426
<212> TYPE: DNA
<213> ORGANISM: Mus musculus

<400> SEQUENCE: 95
atgaagttgc ctgttaggct gttggtgctc tggattcggg agacaatcgg cgatgttgtg    60
atgacccaga ctccactcac tttgtcggtt accgttggac acccagcctc catctcttgc   120
aagtcaagtc agagcctctt agatagtgat ggaaagacat ttttgaattg gttgttacag   180
aggccaggcc agtctccaaa gcgcctaatc tatctggtgt ctaaactgga ctctggagtc   240
cctgacaggt tcactggcag tggatcaggg acagatttca cactgaaaat cagcagagtg   300
gaggctgagg attgggagt ttattattgc tggcaagta cacattttcc gtacacgttc   360 ggaggggga ccaagctgga aataaaacgg gctgatgctg caccaactgt atccatcttc   420
ccacca                                                              426

<210> SEQ ID NO 96
<211> LENGTH: 443
<212> TYPE: DNA
<213> ORGANISM: Mus musculus

<400> SEQUENCE: 96
atggacttcg ggttaaactt ggttttcttt gttgttttt atcaaggtgt gcattgtgag    60
gtgcagcttg ttgagtctgg aggaggattg gtgcagccta agggtcatt gaaactctca   120 tgtgcagcct ctggattcag cttcaatgcc tacgccatga actgggtccg ccaggctcca   180
ggaaagggtt tggaatgggt tgctcgcata agaactaaaa ataataatta tgcaacatat   240

-continued

```
tatgccgatt cagtgaaaga cagatacacc atctccagag atgattcaga aagtatgctc      300
tttctgcaaa tgaacaactt gaaaactgag gacacagcca tgtattactg tgtgacctttt     360 tacggtaacg gtgtctgggg cacagggacc acggtcaccg tctcctcagc caaaacaaca     420
gccccatccg tctatcccct ggt                                              443
```

<210> SEQ ID NO 97
<211> LENGTH: 357
<212> TYPE: DNA
<213> ORGANISM: Artificial Sequence
<220> FEATURE:
<223> OTHER INFORMATION: Humanized heavy chain

<400> SEQUENCE: 97

```
gaggtgcaat tggttgagtc tggaggagga ttggtgaagc ctggggggtc attgagactc      60
tcatgtgcag cctctggatt cactttcagt gcctacgcca tgaactgggt ccgccaggct    120
ccaggaaagg gtttggaatg ggttggccgc ataagaacta aaataataa ttatgcaaca     180 tattatgccg attcagtgaa agacagattc accatctcca gagatgattc aaaaaacacg   240
ctctatctgc aaatgaacag cttgaaaact gaggacacag ccgtgtatta ctgtaccacc    300
ttttacggta acggtgtctg gggccagggg accctggtca ccgtcagctc agccaaa       357
```

<210> SEQ ID NO 98
<211> LENGTH: 344
<212> TYPE: DNA
<213> ORGANISM: Artificial Sequence
<220> FEATURE:
<223> OTHER INFORMATION: Humanized light chain

<400> SEQUENCE: 98

```
ctacgtagtg atgacccagt ctccactctc cttgcccgtt acccttggac agccagcctc     60
catctcttgc aagtcaagtc agagcctctt agatagtgat ggaaagacat ttttgaattg   120
gtttcagcag aggccaggcc agtctccaag gcgcctaatc tatctggtgt ctaaactgga   180
ctctggagtc cctgacaggt tcagcggcag tggatcaggg acagatttca cactgaaaat   240
cagcagagtg gaggctgagg atgttggagt ttattattgc tggcaaggta cacattttcc   300
gtacacgttc ggacaaggga cccgactgga ataaaaacgt acgg                     344
```

<210> SEQ ID NO 99
<211> LENGTH: 443
<212> TYPE: DNA
<213> ORGANISM: Mus musculus

<400> SEQUENCE: 99

```
accagggat agacggatgg ggctgttgtt ttggctgagg agacggtgac cgtggtccct       60
gtgccccaga caccgttacc gtaaaaggtc acacagtaat acatggctgt gtcctcagtt    120
ttcaagttgt tcatttgcag aaagagcata ctttctgaat catctctgga gatggtgtat    180
ctgtctttca ctgaatcggc ataatatgtt gcataattat tatttttagt tcttatgcga   240
gcaacccatt ccaaaccctt tcctggagcc tggcggaccc agttcatggc gtaggcattg   300
aagctgaatc cagaggctgc acatgagagt ttcaatgacc ctttaggctg caccaatcct    360
cctccagact caacaagctg cacctcacaa tgcacaccttt gataaaaaac aacaaagaaa  420
accaagttta acccgaagtc cat                                             443
```

<210> SEQ ID NO 100
<211> LENGTH: 148

```
<212> TYPE: PRT
<213> ORGANISM: Mus musculus

<400> SEQUENCE: 100

Met Asp Phe Gly Leu Asn Leu Val Phe Val Phe Tyr Gln Gly
1               5                   10                  15

Val His Cys Glu Val Gln Leu Val Glu Ser Gly Gly Leu Val Gln
            20                  25                  30

Pro Lys Gly Ser Leu Lys Leu Ser Cys Ala Ala Ser Gly Phe Ser Phe
            35                  40                  45

Asn Ala Tyr Ala Met Asn Trp Val Arg Gln Ala Pro Gly Lys Gly Leu
    50                  55                  60

Glu Trp Val Ala Arg Ile Arg Thr Lys Asn Asn Asn Tyr Ala Thr Tyr
65                  70                  75                  80

Tyr Ala Asp Ser Val Lys Asp Arg Tyr Thr Ile Ser Arg Asp Asp Ser
                85                  90                  95

Glu Ser Met Leu Phe Leu Gln Met Asn Asn Leu Lys Thr Glu Asp Thr
                100                 105                 110

Ala Met Tyr Tyr Cys Val Thr Phe Tyr Gly Asn Gly Val Trp Gly Thr
            115                 120                 125

Gly Thr Thr Val Thr Val Ser Ser Ala Lys Thr Ala Pro Ser Val
        130                 135                 140

Tyr Pro Leu Val
145

<210> SEQ ID NO 101
<211> LENGTH: 426
<212> TYPE: DNA
<213> ORGANISM: Mus musculus

<400> SEQUENCE: 101
tggtgggaag atggatacag ttggtgcagc atcagcccgt tttatttcca gcttggtccc    60
ccctccgaac gtgtacggaa aatgtgtacc ttgccagcaa taataaactc ccaaatcctc   120
agcctccact ctgctgattt tcagtgtgaa atctgtccct gatccactgc cagtgaacct   180
gtcagggact ccagagtcca gtttagacac cagatagatt aggcgctttg agactggcc    240 tggcctctgt aacaaccaat tcaaaaatgt cttttccatca ctatctaaga ggctctgact   300
tgacttgcaa gagatggagg ctgggtgtcc aacggtaacc gacaaagtga gtggagtctg   360
ggtcatcaca acatcgccga ttgtctcccg aatccagagc accaacagcc taacaggcaa   420
cttcat                                                              426

<210> SEQ ID NO 102
<211> LENGTH: 142
<212> TYPE: PRT
<213> ORGANISM: Mus musculus

<400> SEQUENCE: 102

Met Lys Leu Pro Val Arg Leu Leu Val Leu Trp Ile Arg Glu Thr Ile
1               5                   10                  15

Gly Asp Val Val Met Thr Gln Thr Pro Leu Thr Leu Ser Val Thr Val
            20                  25                  30

Gly His Pro Ala Ser Ile Ser Cys Lys Ser Ser Gln Ser Leu Leu Asp
        35                  40                  45

Ser Asp Gly Lys Thr Phe Leu Asn Trp Leu Leu Gln Arg Pro Gly Gln
    50                  55                  60
```

```
Ser Pro Lys Arg Leu Ile Tyr Leu Val Ser Lys Leu Asp Ser Gly Val
 65                  70                  75                  80

Pro Asp Arg Phe Thr Gly Ser Gly Ser Gly Thr Asp Phe Thr Leu Lys
                 85                  90                  95

Ile Ser Arg Val Glu Ala Glu Asp Leu Gly Val Tyr Tyr Cys Trp Gln
                100                 105                 110

Gly Thr His Phe Pro Tyr Thr Phe Gly Gly Thr Lys Leu Glu Ile
            115                 120                 125

Lys Arg Ala Asp Ala Ala Pro Thr Val Ser Ile Phe Pro Pro
130                 135                 140

<210> SEQ ID NO 103
<211> LENGTH: 357
<212> TYPE: DNA
<213> ORGANISM: Artificial Sequence
<220> FEATURE:
<223> OTHER INFORMATION: Humanized heavy chain

<400> SEQUENCE: 103
tttggctgag ctgacggtga ccagggtccc ctggccccag acaccgttac cgtaaaaggt      60
ggtacagtaa tacacggctg tgtcctcagt tttcaagctg ttcatttgca gatagagcgt     120
gttttttgaa tcatctctgg agatggtgaa tctgtctttc actgaatcgg cataatatgt     180
tgcataatta ttatttttag ttcttatgcg gccaacccat tccaaaccct ttcctggagc     240
ctggcggacc cagttcatgg cgtaggcact gaaagtgaat ccagaggctg cacatgagag     300
tctcaatgac cccccaggct tcaccaatcc tcctccagac tcaaccaatt gcacctc        357

<210> SEQ ID NO 104
<211> LENGTH: 119
<212> TYPE: PRT
<213> ORGANISM: Artificial Sequence
<220> FEATURE:
<223> OTHER INFORMATION: Humanized heavy chain

<400> SEQUENCE: 104

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Ala Tyr
                 20                  25                  30

Ala Met Asn Trp Val Arg Gln Ala Pro Gly Lys Gly Leu Glu Trp Val
             35                  40                  45

Gly Arg Ile Arg Thr Lys Asn Asn Tyr Ala Thr Tyr Tyr Ala Asp
     50                  55                  60

Ser Val Lys Asp Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Phe Tyr Gly Asn Gly Val Trp Gly Gln Gly Thr Leu
                100                 105                 110

Val Thr Val Ser Ser Ala Lys
            115

<210> SEQ ID NO 105
<211> LENGTH: 344
<212> TYPE: DNA
<213> ORGANISM: Artificial Sequence
<220> FEATURE:
<223> OTHER INFORMATION: Humanized light chain
```

```
<400> SEQUENCE: 105
ccgtacgttt tatttccagt cgggtccctt gtccgaacgt gtacggaaaa tgtgtacctt      60
gccagcaata ataaactcca acatcctcag cctccactct gctgattttc agtgtgaaat     120
ctgtccctga tccactgccg ctgaacctgt cagggactcc agagtccagt ttagacacca    180
gatagattag gcgccttgga gactggcctg gcctctgctg aaaccaattc aaaaatgtct    240
ttccatcact atctaagagg ctctgacttg acttgcaaga gatggaggct ggctgtccaa    300
gggtaacggg caaggagagt ggagactggg tcatcactac gtag                      344

<210> SEQ ID NO 106
<211> LENGTH: 114
<212> TYPE: PRT
<213> ORGANISM: Artificial Sequence
<220> FEATURE:
<223> OTHER INFORMATION: Humanized light chain

<400> SEQUENCE: 106
```

Tyr Val Val Met Thr Gln Ser Pro Leu Ser Leu Pro Val Thr Leu Gly
 1               5                  10                  15

Gln Pro Ala Ser Ile Ser Cys Lys Ser Ser Gln Ser Leu Leu Asp Ser
            20                  25                  30

Asp Gly Lys Thr Phe Leu Asn Trp Phe Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gln Gly Thr Arg Leu Glu Ile Lys
            100                 105                 110

Arg Thr